US008030300B2

(12) United States Patent
Kozikowski et al.

(10) Patent No.: US 8,030,300 B2
(45) Date of Patent: Oct. 4, 2011

(54) LIGANDS FOR NICOTINIC ACETYLCHOLINE RECEPTORS, AND METHODS OF MAKING AND USING THEM

(75) Inventors: Alan P. Kozikowski, Chicago, IL (US); John L. Musachio, Baltimore, MD (US); Kenneth J. Kellar, Bethesda, MD (US); Yingxian Xiao, Potomac, MD (US); Zhi-Liang Wei, Chicago, IL (US); Hong Fan, Timonium, MD (US)

(73) Assignees: Georgetown University, Washington, DC (US); The John Hopkins University, Baltimore, MD (US)

( * ) Notice: Subject to any disclaimer, the term of this patent is extended or adjusted under 35 U.S.C. 154(b) by 1074 days.

(21) Appl. No.: 10/558,607

(22) PCT Filed: Jun. 9, 2004

(86) PCT No.: PCT/US2004/018340
§ 371 (c)(1),
(2), (4) Date: Mar. 30, 2007

(87) PCT Pub. No.: WO2005/000806
PCT Pub. Date: Jan. 6, 2005

(65) Prior Publication Data
US 2008/0132486 A1 Jun. 5, 2008

Related U.S. Application Data

(60) Provisional application No. 60/477,468, filed on Jun. 10, 2003.

(51) Int. Cl.
*A61K 31/4427* (2006.01)
*C07D 401/12* (2006.01)
(52) U.S. Cl. .................... 514/210.2; 546/268.1
(58) Field of Classification Search ............... 546/268.1; 514/210.2
See application file for complete search history.

(56) References Cited

U.S. PATENT DOCUMENTS

| | | | |
|---|---|---|---|
| 5,629,325 A | 5/1997 | Lin et al. | |
| 5,948,793 A * | 9/1999 | Abreo et al. | 514/318 |
| 6,127,386 A | 10/2000 | Lin et al. | |
| 6,437,138 B1 | 8/2002 | Lin et al. | |
| 2001/0036949 A1 | 11/2001 | Coe et al. | |
| 2003/0008892 A1 | 1/2003 | Coe et al. | |
| 2005/0043406 A1 | 2/2005 | Coe et al. | |
| 2005/0043407 A1 | 2/2005 | Coe et al. | |

FOREIGN PATENT DOCUMENTS

| | | |
|---|---|---|
| EP | 1078637 A2 | 8/2001 |
| EP | 1177798 A2 | 2/2002 |
| EP | 1078637 A3 | 3/2003 |
| EP | 1159970 A3 | 3/2003 |
| EP | 1177798 A3 | 3/2003 |
| WO | WO 98/18798 | 5/1998 |
| WO | WO-98/27144 A1 | 6/1998 |
| WO | WO 01/76576 A3 | 10/2001 |
| WO | WO 02/069948 A1 | 9/2002 |

OTHER PUBLICATIONS

Abreo et al, J. Med. Chem., vol. 39, p. 817-825 (1996).*
Holladay, M.W. et al., "Structure-Activity Studies Related to ABT-594, a Potent Nonopioid Analgesic Agent: Effect of Pyridine and Azetidine Ring Substitutions on Nicotinic Acetylcholine Receptor Binding Affinity and Analgesic Activity in Mice," Bioorganic & Medicinal Chemistry Letters, 8:2797-2802 (1998).
Mamede, M. et al., "Quantification of Human Nicotinic Acetylcholine Receptors with $^{123}$I-5IA SPECT," The J. of Nuclear Medicine, 45(9):1458-1470 (2004).
Staley, J.K., et al., "$^{123}$I-5-IA-85380 SPECT Measurement of Nicotine Acetylcholine Receptors in Human Brain by the Constant Infusion Paradigm: Feasibility and Reproducibility," The J. of Nuclear Medicine, 46(9):1466-1472 (2005).
Fujita, M. et al., "Measurement of $\alpha_4\beta_2$ Nicotinic Acetylcholine Receptor with [$^{123}$I]5-I-A-85380 SPECT," The J. of Nuclear Medicine, 41(9):1552-1560 (2000).

* cited by examiner

*Primary Examiner* — Bernard Dentz
(74) *Attorney, Agent, or Firm* — Foley Hoag LLP

(57) ABSTRACT

One aspect of the present invention relates to heterocyclic compounds that are ligands for nicotinic acetylcholine receptors. A second aspect of the invention relates to the use of a compound of the invention for modulation of a mammalian nicotinic acetylcholine receptor. The present invention also relates to the use of a compound of the invention for treating a mammal suffering from Alzheimer's disease, Parkinson's disease, dyskinesias, Tourette's syndrome, schizophrenia, attention deficit disorder, anxiety, pain, depression, obsessive compulsive disorder, chemical substance abuse, alcoholism, memory deficit, pseudodementia, Ganser's syndrome, migraine pain, bulimia, obesity, premenstrual syndrome or late luteal phase syndrome, tobacco abuse, post-traumatic syndrome, social phobia, chronic fatigue syndrome, premature ejaculation, erectile difficulty, anorexia nervosa, disorders of sleep, autism, mutism or trichtillomania.

13 Claims, 5 Drawing Sheets

(-)-Nicotine

Cytisine (-)-Epibatidine

A-84543

LIGANDS FOR NICOTINIC ACETYLCHOLINE RECEPTORS, AND METHODS OF MAKING AND USING THEM

RELATED APPLICATIONS

This application claims the benefit of the filing date of Patent Cooperation Treaty Application number PCT/US2004/018340, filed Jun. 9, 2004; which claims the benefit of priority to United States Provisional Patent Application Ser. No. 60/477,468, filed Jun. 10, 2003.

Government Support

Work described herein was funded, in whole or in part, by the National Institutes of Health (R01 Grant Number DA017980). The United States government has certain rights in the invention.

BACKGROUND OF THE INVENTION

The endogenous cholinergic neurotransmitter, acetylcholine, exert its biological effect via two types of cholinergic receptors; the muscarinic ACh receptors and the nicotinic ACh receptors. As it is well established that muscarinic ACh receptors dominate quantitatively over nicotinic ACh receptors in the brain area important to memory and cognition, much research aimed at the development of agents for the treatment of memory related disorders have focused on the synthesis of muscarinic ACh receptor modulators. Recently, however, an interest in the development of nicotinic ACh receptor modulators has emerged. Several diseases are associated with degeneration of the cholinergic system i.e. senile dementia of the Alzheimer type, vascular dementia and cognitive impairment due to the organic brain damage disease related directly to alcoholism. Indeed several CNS disorders can be attributed to a cholinergic deficiency, a dopaminergic deficiency, an adrenergic deficiency or a serotonergic deficiency. Alzheimer's disease is characterised by a profound loss of memory and cognitive functions caused by a severe depletion of cholinergic neurons, i.e. neurons that release acetylcholine. A reduction in the number of nicotinic ACh receptors are also observed with the progression of Alzheimer's disease. It is believed that the neurons in the cortex that die with the progression of Alzheimer's disease do so because of lack of stimulation of the nicotinic ACh receptors. It is predicted that treatment of Alzheimer patients with nicotinic ACh receptor modulators will not only improve the memory of patients but in addition act to keep these neurons alive. Smoking actually seems to protect individuals against neurodegeneration and compounds behaving on these receptor may very likely have a generally neuroprotective effect.

However degeneration of the cholinergic system is not limited to individuals suffering from i.e. Alzheimers disease but is also seen in healthy aged adults and rats. Therefore it is suggested that the cholinergic system is involved and partly responsible for the memory disturbances seen in aged animals and humans. Nicotine receptor modulator may therefore be useful in the treatment of Alzheimer's disease, memory loss, memory dysfunction, AIDS-dementia, senile dementia or neurodegenerative disorders.

Parkinsons disease appears to involve degeneration of dopaminergic neurons. One symptom of the disease has been observed to be loss of nicotinic receptors associated with the dopaminergic neurons and possibly interfering with the process of release of dopamine. As sustained nicotine administration increases the number of receptors present, administration of nicotine receptor modulators may ameliorate the symptoms of Parkinson's disease. Other condition or disorders or disease ascribed to deficiencies in the dopaminergic system is: drug addiction, depression, obesity and narcolepsy.

Tourette's syndrome is a neuropsychiatric disorder involving a range of neurological and behavioral symptoms. It is believed that neurotransmitter dysfunction is involved though the pathophysiology is still unknown and that nicotine will be beneficial in the treatment of the disease (Devor et. al. The Lancet, vol. 8670 p. 1046, 1989).

Schizophrenia is a severe psychiatric illness. Neuroleptic compounds has been used in the treatment of the disease, the effect of the compounds is believed to be interaction in the dopaminergic system. Nicotine is proposed to be effective in the treatment of schizophrenia (Merriam et. al. Psychiatr. annals, Vol. 23, p. 171-178, 1993 and Adler et. al. Biol. Psychiatry, Vol. 32, p. 607-616, 1992.)

Nicotine has been reported to have en effect on neurotransmitter release in several systems. Release of acetylcholine and dopamine by neurons upon administration of nicotine has been reported (J. Neurochem. vol. 43, 1593-1598, 1984) and release of norepinephrine by Hall et. al. (Biochem. Pharmacol. vol. 21, 1829-1838, 1972) Release of serotonin by Hery et. al. (Arch. Int. Pharmacodyn. Ther. vol. 296. p. 91-97, 1977). Release of glutamate by Toth et. al (Neurochem. Res. vol. 17, p. 265-271, 1992).

The serotonin system and dysfunction's of the serotonergic system is believed to be involved in diseases or conditions or disorders like: anxiety, depression, eating disorders, obsessive compulsive disorder, panic disorders, chemical substance abuse, alcoholism, pain, memory deficits and anxiety, pseudodementia, Ganser's syndrome, migraine pain, bulimia, obesity, premenstrual syndrome or late luteal phase syndrome, tobacco abuse, post-traumatic syndrome, social phobia, chronic fatigue syndrome, premature ejaculation, erectile difficulty, anorexia nervosa, disorders of sleep, autism, mutism or trichotillomania.

Nicotine improves concentration and task performance. Therefore compounds exhibiting nicotine receptor modulating properties will be likely to be useful compounds in the treatment of leaning deficit, cognition deficit, attention deficit, attention deficit hyperactivity disorder and dyslexia.

Tobacco use and especially cigarette smoking is recognised as a serious health problem. However nicotine withdrawal symptoms associated with smoking cessation makes it difficult to break this habit. Withdrawal symptoms include anger, anxiety, difficulties in concentrating, restlessness, decreased heart rate and increased appetite and weight gain. Nicotine itself has shown to ease the withdrawal symptoms.

Withdrawal from addictive substances, i.e. opiates, benzodiazepines, ethanol, tobacco or nicotine, is in general a traumatic experience characterized by anxiety and frustration. Nicotine has been found to be effective in reducing anger, irritability, frustration and feelings of tension without causing general response depression, drowsiness or sedation and compounds having same characteristics as nicotine is likely to have same effects.

Mild to moderate pain is normally treatable with NSAID's (non-steroidal anti-inflammatory drugs) while opiates are used preferentially for moderate to severe pain. The opiates have some well-known side-effects, including chemical dependence and abuse potential as well as a depressive effect on the respiratory and gastrointestinal system. There exists therefore a strong need for analgesic compounds that do not exhibit these side effects and which can relieve mild, moderate and severe pain of acute, chronic or recurrent character as well as migraine pain and postoperative pain, phantom limb pain.

Epibatidine, a compound isolated from the skin of a poison frog, is a very potent analgesic with an approximate potency of 500 times that of morphine. The analgesic effect is not affected by naloxone, which is an indication of a negligible affinity for the opiate receptors. Epibatidine is an nicotinic cholinergic receptor agonist and it is therefore very likely, that compounds possessing this receptor modulating character will also show a strong analgesic response. It is well known that nicotine has an effect on appetite and it is predicted that modulators at the nicotine ACh receptor may be useful as appetite suppressants in the treatment of obesity and eating disorders.

In addition to epibatidine, various heterocyclic 2-pyrrolidinyloxy-substituted compounds with analgesic and hypotensive activities have been disclosed by Scheffler et al. (U.S. Pat. No. 4,643,995) and Tomioka et al. (Chem. Pharm. Bull, 38:2133-5, 1990).

Certain other 2-pyridyloxy-substituted compounds are disclosed inter alia by Engel et al. in U.S. Pat. No. 4,946,836 as having analgesic activity.

Various other compounds having a pyrrolidine or azetidine moiety substituted at the 3-position with a heterocycloxy group have also been disclosed (cf. U.S. Pat. No. 4,592,866 to A. D. Cale; U.S. Pat. No. 4,705,853 to A. D. Cale; U.S. Pat. No. 4,956,359 to Taylor et al.; and U.S. Pat. No. 5,037,841 to Schoehe et al. and European patent application EP296560A2, to Sugimoto et al.).

The cholinergic receptors play an important role in the functioning of muscles, organs and generally in the central nervous system. There are also complex interactions between cholinergic receptors and the function of receptors of other neurotransmitters such as dopamine, serotonin and noradrenaline.

It is likely that nicotine receptor modulator compounds can be effective in preventing or treating conditions or disorders or diseases like: inflammation, inflammatory skin conditions, Chron's disease, inflammatory bowel disease, ulcerative collitis, diarrhoea, neurodegeneration, perpherical neuropathy, amyotrophic lateral sclerosis, nociception, endocrine disorders, thyrotoxicosis, pheochromocytoma, hypertension, arrhytmias, mania, manic depression, Huntington's disease, jetlag.

The compounds of the present invention are nicotine receptor modulators and have the potential to exhibit nicotinic pharmacology, preferentially without the side effects associated with nicotine itself. Additionally, the compounds are expected to have the potential as enhancers of neurotransmitter secretion and suppress symptoms associated with a low activity of neurotransmitters.

SUMMARY OF THE INVENTION

In part, the present invention relates to a compound of formula I:

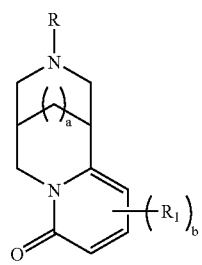

wherein, independently for each occurrence,
a is 1 or 2;
b is 1, 2, or 3;

R is $C_1$-$C_6$ alkyl, $C_2$-$C_8$ alkenyl, $C_2$-$C_8$ alkenyl, aryl, heteroaryl, or aralkyl, optionally substituted with one or more halide, hydroxy, alkoxy, amino, nitro, or —$OR_2$ group, wherein $R_2$ is $C_1$-$C_6$ alkyl, $C_2$-$C_8$ alkenyl, $C_2$-$C_8$ alkenyl, aryl, heteroaryl, or aralkyl;

$R_1$ is H, halide, hydroxy, alkoxy, amino, nitro, $C_1$-$C_6$ alkyl, $C_2$-$C_8$ alkenyl, $C_2$-$C_8$ alkenyl, aryl, heteroaryl, aralkyl, or any two $R_1$ can form a fused ring; or $R_1$ is of formula Ia:

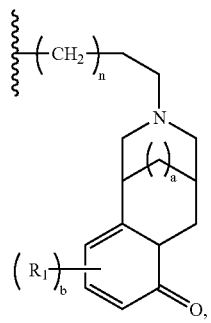

wherein, independently for each occurrence,
n is an integer from 1 to 6 inclusively;
a is 1 or 2;
b is 1, 2, or 3; and $R_1$ is H, halide, hydroxy, alkoxy, amino, nitro, $C_1$-$C_6$ alkyl, $C_2$-$C_8$ alkenyl, $C_2$-$C_8$ alkenyl, aryl, heteroaryl, aralkyl, or any two $R_1$ can form a fused ring.

In a further embodiment, the present invention relates to a compound of formula I and the attendant definitions, wherein a is 1.

In a further embodiment, the present invention relates to a compound of formula I and the attendant definitions, wherein $R_1$ is H and b is 3.

In a further embodiment, the present invention relates to a compound of formula I and the attendant definitions, wherein R is Ia and the attendant definitions.

In a further embodiment, the present invention relates to a compound of formula I and the attendant definitions, wherein a is 1, $R_1$ is H, b is 3, and R is —$C_2H_6Cl$.

In a further embodiment, the present invention relates to a compound of formula I and the attendant definitions, wherein a is 1, $R_1$ is H, b is 3, and R is —$CH_3H_6O$-3-pyridinyl.

In a further embodiment, the present invention relates to a compound of formula I and the attendant definitions, wherein a is 1, $R_1$ is H, b is 3, and R is Ia, wherein a is 1, $R_1$ is H, b is 3, and n is 2.

In a further embodiment, the present invention relates to a compound of formula I and the attendant definitions, wherein a is 1, $R_1$ is H, b is 3, and R is Ia, wherein a is 1, $R_1$ is H, b is 3, and n is 4.

In a further embodiment, the present invention relates to a compound of formula I and the attendant definitions, wherein a is 1, $R_1$ is H, b is 3, and R is Ia, wherein a is 1, $R_1$ is H, b is 3, and n is 5.

In another embodiment the present invention relates to a compound of formula II:

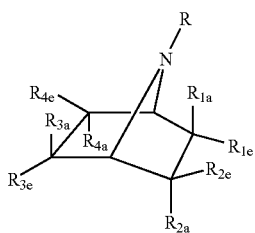

wherein, independently for each occurrence,

R is H, $C_1$-$C_6$ alkyl, $C_2$-$C_8$ alkenyl, $C_2$-$C_8$ alkenyl, aryl, heteroaryl, or aralkyl, optionally substituted with one or more halide, hydroxy, alkoxy, amino, or nitro groups;

$R_{1a}$, $R_{1e}$, $R_{2a}$, $R_{2e}$, $R_{3a}$, $R_{3e}$, $R_{4a}$ and $R_{4e}$ are selected from the group consisting of H, hydroxy, amino, halide, aryl, alkoxy, and heteroaryl groups, wherein the aryl and heteroaryl groups are optionally substituted with one or more halide, alkyl, alkenyl, or alkynyl groups; or any germinal $R_{1a}$, $R_{1e}$, $R_{2a}$, $R_{2e}$, $R_{3a}$, $R_{3e}$, $R_{4a}$ and $R_{4e}$ groups may form a monocyclic or bicyclic ring, or =O; or any adjacent $R_{1a}$, $R_{1e}$, $R_{2a}$, $R_{2e}$, $R_{3a}$, $R_{3e}$, $R_{4a}$ and $R_{4e}$ groups may form a monocyclic or bicyclic ring; and providing that at least one of $R_{1a}$ or $R_{1e}$ is hydroxy or heteroaryl, and if $R_{1a}$ or $R_{1e}$ is hydroxy then $R_{2a}$ or $R_{2e}$ is heteroaryl, and if $R_{1a}$ or $R_{1e}$ is heteroaryl then at least one $R_{2a}$, $R_{2e}$, $R_{3a}$, $R_{3e}$, $R_{4a}$ or $R_{4e}$ is not H;

or

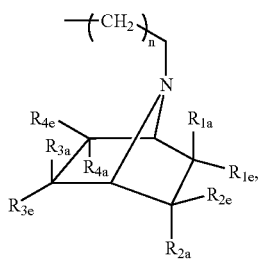

R is of formula IIa:

wherein, independently for each occurrence, $R_{1a}$, $R_{1e}$, $R_{2a}$, $R_{2e}$, $R_{3a}$, $R_{3e}$, $R_{4a}$ and $R_{4e}$ are selected from the group consisting of H, hydroxy, amino, halide, aryl, alkoxy, and heteroaryl groups, wherein the aryl and heteroaryl groups are optionally substituted with one or more halide, alkyl, alkenyl, or alkynyl groups; and n is an integer from 1 to 9 inclusively.

In a further embodiment, the present invention relates to a compound of formula II and the attendant definitions, wherein R is H.

In a further embodiment, the present invention relates to a compound of formula II and the attendant definitions, wherein $R_{1a}$ is OH.

In a further embodiment, the present invention relates to a compound of formula II and the attendant definitions, wherein $R_{1e}$ is OH.

In a further embodiment, the present invention relates to a compound of formula II and the attendant definitions, wherein $R_{1a}$ is 2-chloro-5-pyridinyl.

In a further embodiment, the present invention relates to a compound of formula II and the attendant definitions, wherein $R_{1e}$ is 2-chloro-5-pyridinyl.

In a further embodiment, the present invention relates to a compound of formula II and the attendant definitions, wherein $R_{2a}$ is OH.

In a further embodiment, the present invention relates to a compound of formula II and the attendant definitions, wherein $R_{2e}$ is OH.

In a further embodiment, the present invention relates to a compound of formula II and the attendant definitions, wherein $R_{2a}$ is 2-chloro-5-pyridinyl.

In a further embodiment, the present invention relates to a compound of formula II and the attendant definitions, wherein $R_{2b}$ is 2-chloro-5-pyridinyl.

In a further embodiment, the present invention relates to a compound of formula II and the attendant definitions, wherein $R_{1e}$ is F.

In a further embodiment, the present invention relates to a compound of formula II and the attendant definitions, wherein $R_{1a}$ is F.

In a further embodiment, the present invention relates to a compound of formula II and the attendant definitions, wherein $R_{2a}$ is F.

In a further embodiment, the present invention relates to a compound of formula II and the attendant definitions, wherein $R_{2e}$ is F.

In a further embodiment, the present invention relates to a compound of formula II and the attendant definitions, wherein R is H, $R_{1a}$ is OH, and $R_{2a}$ is 2-chloro-5-pyridinyl.

In a further embodiment, the present invention relates to a compound of formula II and the attendant definitions, wherein R is H, $R_{1e}$ is OH, and $R_{2a}$ is 2-chloro-5-pyridinyl.

In a further embodiment, the present invention relates to a compound of formula II and the attendant definitions, wherein R is H, $R_{1e}$ is 2-chloro-5-pyridinyl, and $R_{2e}$ is OH.

In a further embodiment, the present invention relates to a compound of formula II and the attendant definitions, wherein R is H, $R_{1e}$ is 2-chloro-5-pyridinyl, and $R_{2a}$ is OH.

In a further embodiment, the present invention relates to a compound of formula II and the attendant definitions, wherein R is H, $R_{1e}$ is 2-chloro-5-pyridinyl, and $R_{3a}$ is OH.

In a further embodiment, the present invention relates to a compound of formula II and the attendant definitions, wherein R is H, $R_{1e}$ is 2-chloro-5-pyridinyl, and $R_{4a}$ is OH.

In a further embodiment, the present invention relates to a compound of formula II and the attendant definitions, wherein R is H, $R_{1e}$ is 2-chloro-5-pyridinyl, and $R_{3e}$ is OH.

In a further embodiment, the present invention relates to a compound of formula II and the attendant definitions, wherein R is H, $R_{1e}$ is 2-chloro-5-pyridinyl, and $R_{4e}$ is OH.

In a further embodiment, the present invention relates to a compound of formula II and the attendant definitions, wherein R is H, $R_{1e}$ is 2-chloro-5-pyridinyl, and $R_{3e}$ is F.

In a further embodiment, the present invention relates to a compound of formula II and the attendant definitions, wherein R is H, $R_{1e}$ is 2-chloro-5-pyridinyl, and $R_{4e}$ is F.

In a further embodiment, the present invention relates to a compound of formula II and the attendant definitions, wherein R is H, and $R_{1a}$ and $R_{1e}$ form

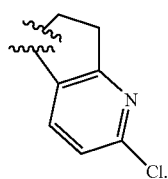

In a further embodiment, the present invention relates to a compound of formula II and the attendant definitions, wherein R is H, and $R_{1e}$ and $R_{2e}$ form

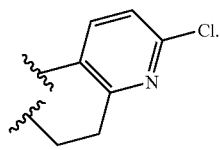

In a further embodiment, the present invention relates to a compound of formula II and the attendant definitions, wherein R is H, and $R_{1a}$ and $R_{1e}$ form

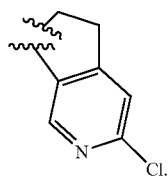

In a further embodiment, the present invention relates to a compound of formula II and the attendant definitions, wherein R is H, and $R_{1e}$ and $R_{2e}$ form

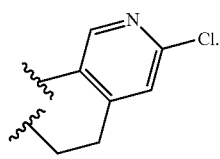

In a further embodiment, the present invention relates to a compound of formula II and the attendant definitions, wherein R is H and $R_{1e}$ is 2-(6-hydroxy-1-hexynyl)-5-pyridinyl.

In a further embodiment, the present invention relates to a compound of formula II and the attendant definitions, wherein R is H, $R_{1e}$ is 2-chloro-5-pyridinyl, and $R_{3a}$ and $R_{3e}$ form =O.

In a further embodiment, the present invention relates to a compound of formula II and the attendant definitions, wherein R is H, $R_{1e}$ is 2-chloro-5-pyridinyl, and $R_{4a}$ and $R_{4e}$ form =O.

In a further embodiment, the present invention relates to a compound of formula II and the attendant definitions, wherein R is H, $R_{1e}$ is 2-chloro-5-pyridinyl, and $R_{4a}$ and $R_{4e}$ form

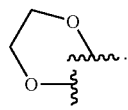

In a further embodiment, the present invention relates to a compound of formula II and the attendant definitions, wherein $R_{1e}$ is 2-chloro-5-pyridinyl and R is IIa and the attendant definitions, wherein n is 5, and $R_{1e}$ is 2-chloro-5-pyridinyl.

In a further embodiment, the present invention relates to a compound of formula II and the attendant definitions, wherein $R_{1e}$ is 2-chloro-5-pyridinyl and R is IIa and the attendant definitions, wherein n is 2, and $R_{1e}$ is 2-chloro-5-pyridinyl.

In a further embodiment, the present invention relates to a compound of formula II and the attendant definitions, wherein $R_{1e}$ is 2-chloropyridin-5-yl and R is IIa and the attendant definitions, wherein n is 9, and $R_{1e}$ is 2-chloro-5-pyridinyl.

In a further embodiment, the present invention relates to a compound of formula II and the attendant definitions, wherein $R_{1e}$ is 2-chloro-5-pyridinyl and R is IIa and the attendant definitions, wherein n is 1, and $R_{1e}$ is 2-chloro-5-pyridinyl.

In a further embodiment, the present invention relates to a compound of formula II and the attendant definitions, wherein $R_{2e}$ is 2-chloro-5-pyridinyl and R is IIa and the attendant definitions, wherein n is 1, and $R_{1e}$ is 2-chloro-5-pyridinyl.

In another embodiment, the present invention relates to compound of formula III:

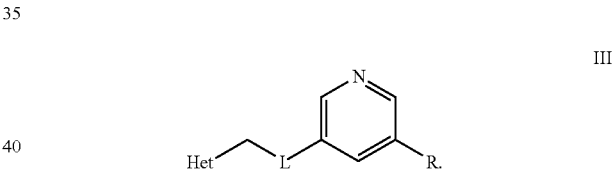

wherein, independently for each occurrence,
L is O, S, or NR;
Het is a heterocyclic; and
R is H, halide, amino, nitro, hydroxy, alkoxy, or an optionally substituted $C_1$-$C_6$ alkyl, $C_2$-$C_6$ alkenyl, or $C_2$-$C_{10}$ alkynyl, where the substituents are selected from the group consisting of hydroxy, halide, amino, nitro, and alkoxy.

In a further embodiment, the present invention relates to a compound of formula III and the attendant definitions, wherein L is O.

In a further embodiment, the present invention relates to a compound of formula III and the attendant definitions, wherein Het is 1-methyl-2-pyrrolidinyl.

In a further embodiment, the present invention relates to a compound of formula III and the attendant definitions, wherein Het is 2-azetidinyl.

In a further embodiment, the present invention relates to a compound of formula III and the attendant definitions, wherein R is H.

In a further embodiment, the present invention relates to a compound of formula III and the attendant definitions, wherein R is Br.

In a further embodiment, the present invention relates to a compound of formula III and the attendant definitions, wherein R is an alkynyl group.

In a further embodiment, the present invention relates to a compound of formula III and the attendant definitions, wherein R is an hydroxy substituted alkynyl group.

In a further embodiment, the present invention relates to a compound of formula III and the attendant definitions, wherein L is O, Het is 1-methyl-2-pyrrolidinyl, and R is H.

In a further embodiment, the present invention relates to a compound of formula III and the attendant definitions, wherein L is O, Het is 1-methyl-2-pyrrolidinyl, and R is Br.

In a further embodiment, the present invention relates to a compound of formula III and the attendant definitions, wherein L is O, Het is 1-methyl-2-pyrrolidinyl, and R is —CCH.

In a further embodiment, the present invention relates to a compound of formula III and the attendant definitions, wherein L is O, Het is 1-methyl-2-pyrrolidinyl, and R is —CCCH$_2$OH.

In a further embodiment, the present invention relates to a compound of formula III and the attendant definitions, wherein L is O, Het is 1-methyl-2-pyrrolidinyl, and R is —CC(CH$_2$)$_4$OH.

In a further embodiment, the present invention relates to a compound of formula III and the attendant definitions, wherein L is O, Het is 1-methyl-2-pyrrolidinyl, and R is —(CH$_2$)$_6$OH.

In a further embodiment, the present invention relates to a compound of formula III and the attendant definitions, wherein L is O, Het is 1-methyl-2-pyrrolidinyl, and R is —CC(CH$_2$)$_8$OH.

In a further embodiment, the present invention relates to a compound of formula III and the attendant definitions, wherein L is O, Het is 2-azetidinyl, and R is H.

In a further embodiment, the present invention relates to a compound of formula III and the attendant definitions, wherein L is O, Het is 2-azetidinyl, and R is —CC(CH$_2$)$_4$OH.

In another embodiment, the present invention relates to a pharmaceutical composition comprising a compound of formula I, II, or III and a pharmaceutically acceptable excipient.

In cases in which the compounds of formula I, II, or III have unsaturated carbon-carbon double bonds, both the cis (Z) and trans (E) isomers are within the scope of this invention. In cases wherein the compounds may exist in tautomeric forms, such as keto-enol tautomers, such as

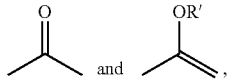

each tautomeric form is contemplated as being included within this invention, whether existing in equilibrium or locked in one form by appropriate substitution with R'. The meaning of any substituent at any one occurrence is independent of its meaning, or any other substituent's meaning, at any other occurrence.

Also included in the nicotine AChR ligand compounds of the present invention are prodrugs of the compounds of formula I, II, or III. Prodrugs are considered to be any covalently bonded carriers which release the active parent drug in vivo.

The compounds of this invention may exist in unsolvated as well as in solvated forms with pharmaceutically acceptable solvents such as water, ethanol and the like. In general, the solvated forms are considered equivalent to the unsolvated forms for the purposes of this invention.

It will be appreciated by those skilled in the art that the compounds of the present invention contain several chiral centers and that such compounds exist in the form of isomers (i.e. enantiomers). The invention includes all such isomers and any mixtures thereof including racemic mixtures.

Racemic forms can be resolved into the optical antipodes by known methods, for example, by separation of diastereomeric salts thereof with an optically active acid, and liberating the optically active amine compound by treatment with a base. Another method for resolving racemates into the optical antipodes is based upon chromatography on an optically active matrix. Racemic compounds of the present invention can thus be resolved into their optical antipodes, e.g., by fractional crystallization of d- or l-(tartrates, mandelates, or camphorsulphonate) salts for example. The compounds of the present invention may also be resolved by the formation of diastereomeric amides by reaction of the compounds of the present invention with an optically active activated carboxylic acid such as that derived from (+) or (−) phenylalanine, (+) or (−) phenylglycine, (+) or (−) camphanic acid or by the formation of diastereomeric carbamates by reaction of the compounds of the present invention with an optically active chloroformate or the like.

Additional methods for the resolution of optical isomers, known to those skilled in the art may be used, and will be apparent to the average worker skilled in the art. Such methods include those discussed by J. Jaques, A. Collet, and S. Wilen in "Enantiomers, Racemates, and Resolutions", John Wiley and Sons, New York (1981).

Optical active compounds can also be prepared from optical active starting materials.

In another embodiment, the present invention relates to a compound of formula I, II, or III, wherein the compound has an IC$_{50}$ less than 1 µM in an assay based on a mammalian nicotine ACh receptor. In a further embodiment, the compound of formula I, II, or III has an IC$_{50}$ less than 100 nM in an assay based on a mammalian nicotine ACh receptor. In a further embodiment, the compound of formula I, II, or III has an IC$_{50}$ less than 10 nM in an assay based on a mammalian nicotine ACh receptor. In a further embodiment, the compound of formula I, II, or III has an IC$_{50}$ less than 1 nM in an assay based on a mammalian nicotine ACh receptor.

In another embodiment, the present invention relates to a compound of formula I, II, or III, wherein the compound has an EC$_{50}$ less than 1 µM. In a further embodiment the compound has an EC$_{50}$ less than 100 nM in an assay based on a mammalian nicotine ACh receptor. In a further embodiment, the compound of formula I, II, or III, wherein the compound has an EC$_{50}$ less than 10 nM in an assay based on a mammalian nicotine ACh receptor.

In another embodiment, the present invention relates to a compound of formula I, II, or III, wherein the compound is a single stereoisomer.

In accordance with the present invention, a compound of the present invention may be prepared as pharmaceutical compositions that are particularly useful for the treatment of neurodegenerative diseases or addictive disorders. Such compositions comprise a compound of the present invention with pharmaceutically acceptable carriers and/or excipients.

For example, these compositions may be prepared as medicines to be administered orally, parenterally, rectally, transdermally, bucally, or nasally. Suitable forms for oral administration include tablets, compressed or coated pills, dragees, sachets of powder for reconstitution, hard or gelatin capsules, sub-lingual tablets, syrups and suspensions. Suitable forms for parenteral administration include an aqueous or non-aqueous solution or emulsion, while for rectal administration suitable forms include suppositories with hydrophilic or hydrophobic vehicles. For topical application the invention provides ointments or aerosol formulations known in the art; for transdermal delivery there are provided suitable delivery systems as known in the art. For nasal delivery there are provided suitable aerosol delivery systems known in the art.

In another aspect of the present invention, the pharmaceutical compositions of the present invention may be used in the manufacture of a medicament to treat neurodegenerative or addictive disorders. In certain embodiments, the present invention is directed to a method for formulating compositions of the present invention in a pharmaceutically acceptable carrier.

In certain embodiments, the pharmaceutical compositions are formulated as a tablet, pill capsule or other appropriate ingestible formulation, to provide a therapeutic dose in 10 tablets or fewer. In another example, a therapeutic dose is provided in 50, 40, 30, 20, 15, 10, 5 or 3 tablets.

In another aspect, the present invention also provides for kits containing at least one dose of a subject composition, and often many doses, and other materials for a treatment regimen. For example, in one embodiment, a kit of the present invention contains sufficient subject composition for from five to thirty days and optionally equipment and supplies necessary to measure one or more indices relevant to the treatment regiment. In another embodiment, kits of the present invention contain all the materials and supplies, including subject compositions, for carrying out any methods of the present invention. In still another embodiment, kits of the present invention, as described above, additionally include instructions for the use and administration of the subject compositions.

The dosage may be selected to assuage the disorder in a subject in such a way as to provide at least partial relief if not complete relief. The skilled artisan may identify this amount as provided herein as well as by using other methods known in the art.

In another embodiment, the present invention relates to a method of modulating a nicotine ACh receptor in a mammal comprising administering to the mammal a compound of formula I, II, or III. In a further embodiment, the mammal is a primate, equine, canine, or feline. In a further embodiment, the mammal is a human.

In another embodiment, the present invention relates to a method of modulating a nicotine ACh receptor in a mammal comprising administering to the mammal a compound of formula I, II, or III, wherein the compound is administered orally. In a further embodiment, the compound is administered intravenously, sublingually, ocularly, transdermally, rectally, vaginally, topically, intramuscularly, subcutaneously, buccally, or nasally.

In another embodiment, the present invention relates to a method of treating a mammal suffering from Alzheimer's disease, Parkinson's disease, dyskinesias, Tourette's syndrome, schizophrenia, attention deficit disorder, anxiety, pain, depression, obsessive compulsive disorder, chemical substance abuse, alcoholism, memory deficit, pseudodementia, Ganser's syndrome, migraine pain, bulimia, obesity, premenstrual syndrome or late luteal phase syndrome, tobacco abuse, post-traumatic syndrome, social phobia, chronic fatigue syndrome, premature ejaculation, erectile difficulty, anorexia nervosa, disorders of sleep, autism, mutism or trichtillomania comprising administering a therapeutically effective amount of a compound of formula I, II, or III. In a further embodiment, the mammal is a primate, equine, canine, or feline. In a further embodiment, the mammal is a human. In a further embodiment, the compound is administered orally, intravenously, sublingually, ocularly, transdermally, rectally, vaginally, topically, intramuscularly, subcutaneously, buccally, or nasally.

As explained herein in greater detail, the invention will readily enable the design and implementation of trials in warm-blooded animals, including humans and mammals, necessary for easily determining or tailoring the form and dose for any composition of the present invention.

These embodiments of the present invention, other embodiments, and their features and characteristics, will be apparent from the description, drawings and claims that follow.

DETAILED DESCRIPTION OF THE INVENTION

Definitions

Figure 1:
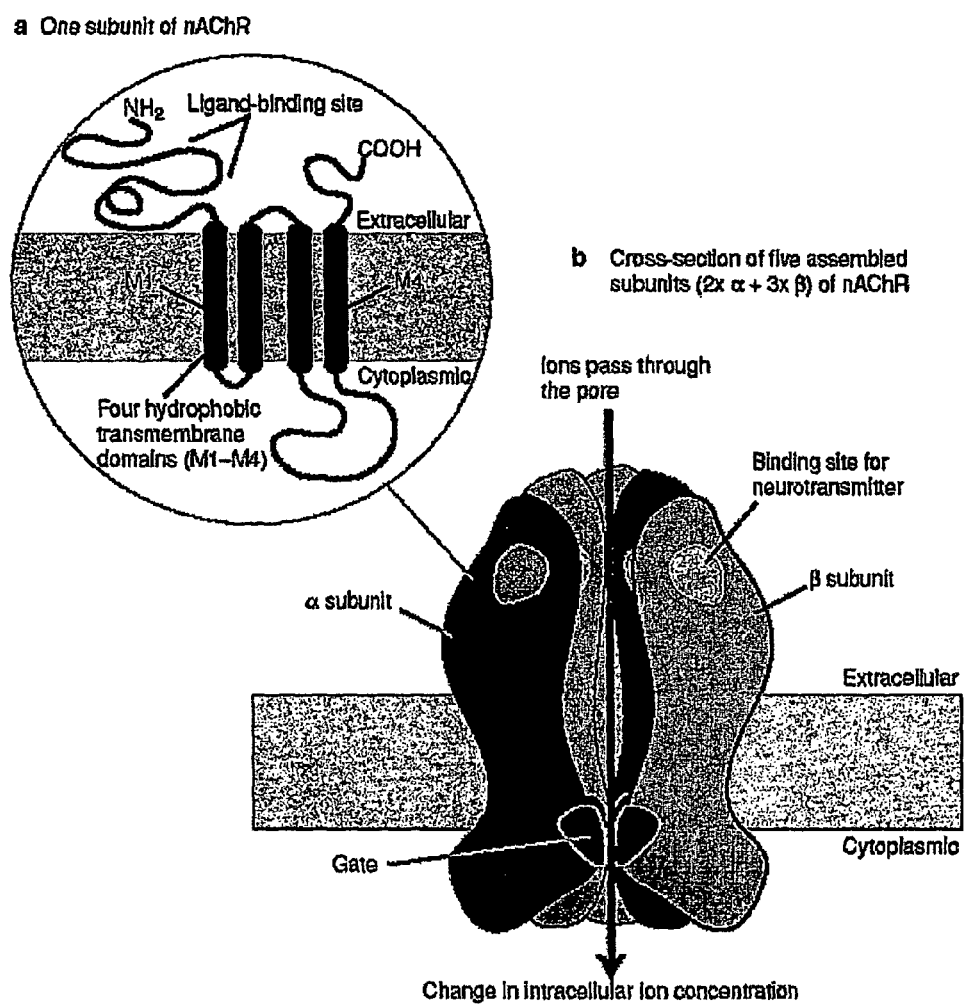
FIG. 1 depicts the structure of a neuronal nicotinic acetylcholine receptor (nAChR).
Figure 2:
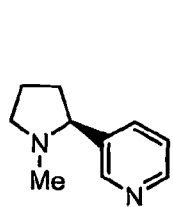
FIG. 2 depicts the chemical structures of (−)-nicotine, cytisine, (−)-epibatidine, and compound A-84543.
Figure 2:
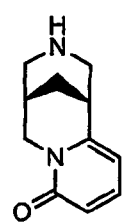
Figure 2:
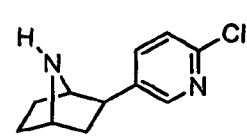
Figure 2:
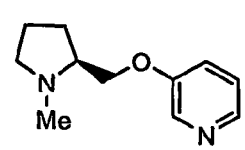
Figure 3:
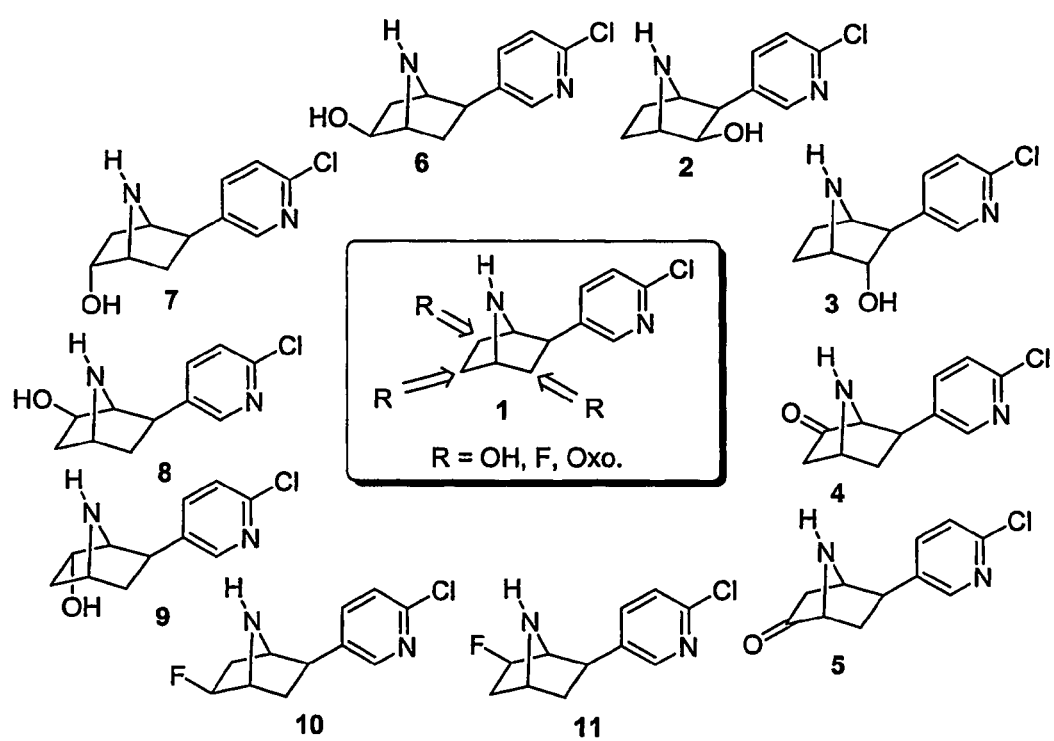
FIG. 3 depicts the functionalization of the alicyclic skeleton of epibatidine.
Figure 4:
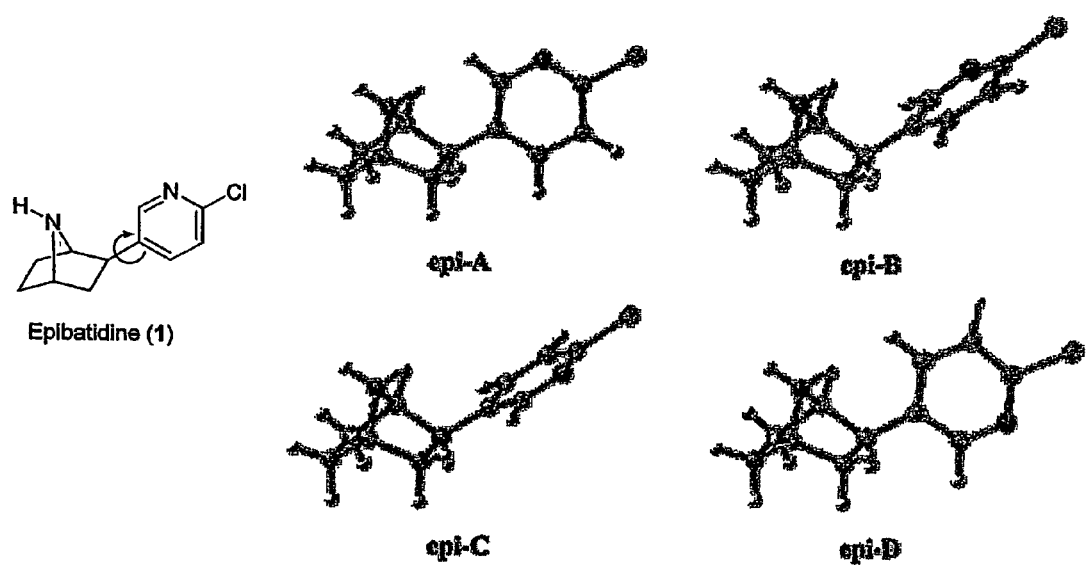
FIG. 4 depicts the synthesis of conformationally constrained epibatidine analogs.
Figure 5:
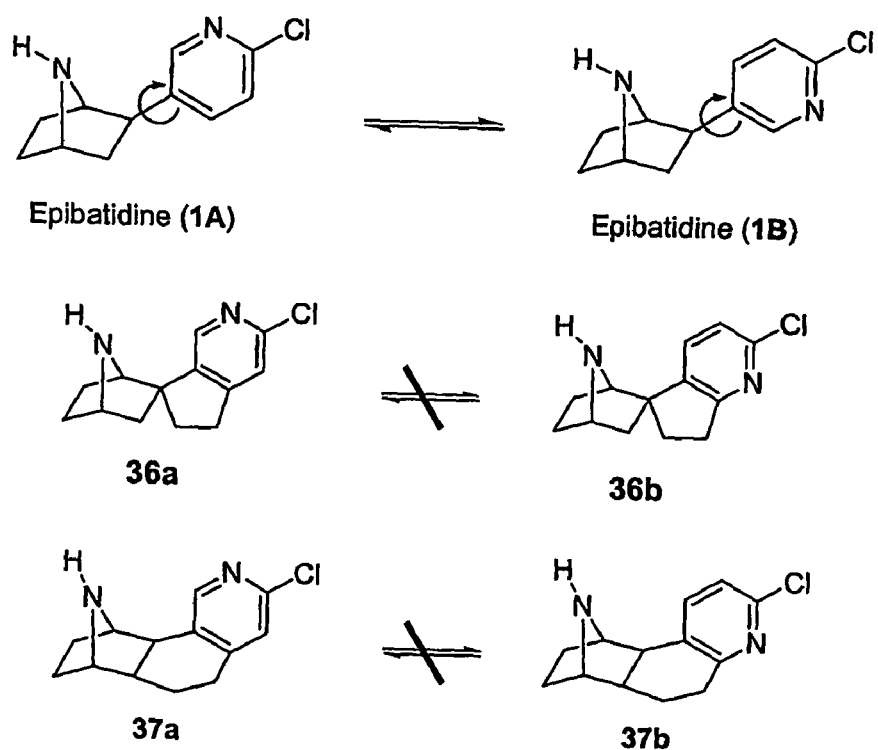
FIG. 5 depicts the limited rotational movement of the constrained epibatidine analogs.

For convenience, certain terms employed in the specification, examples, and appended claims are collected here.

The articles "a", and "an" are used herein to refer to one or to more than one (i.e., to at least one) of the grammatical object of the article. By way of example, "an element" means one element or more than one element.

The term "$ED_{50}$" means the dose of a drug which produces 50% of its maximum response or effect. Alternatively, the dose which produces a predetermined response in 50% of test subjects or preparations.

The term "$LD_{50}$" means the dose of a drug which is lethal in 50% of test subjects.

The term "therapeutic index" refers to the therapeutic index of a drug defined as $LD_{50}/ED_{50}$.

The term "structure-activity relationship (SAR)" refers to the way in which altering the molecular structure of drugs alters their interaction with a receptor, enzyme, etc.

The term "agonist" refers to a compound that mimics the action of natural transmitter or, when the natural transmitter is not known, causes changes at the receptor complex in the absence of other receptor ligands.

The term "antagonist" refers to a compound that binds to a receptor site, but does not cause any physiological changes unless another receptor ligand is present.

The term "inverse agonist" refers to a compound that binds to a constitutively active receptor site and reduces its physiological function.

The term "competitive antagonist" refers to a compound that binds to a receptor site; its effects can be overcome by increased concentration of the agonist.

The term "partial agonist" refers to a compound that binds to a receptor site but does not produce the maximal effect regardless of its concentration.

The term "ligand" refers to a compound that binds at the receptor site.

The term "heteroatom" as used herein means an atom of any element other than carbon or hydrogen. Preferred heteroatoms are boron, nitrogen, oxygen, phosphorus, sulfur and selenium.

The term "alkyl" refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. In preferred embodiments, a straight chain or branched chain alkyl has 30 or fewer carbon atoms in its backbone (e.g., $C_1$-$C_{30}$ for straight chain, $C_3$-$C_{30}$ for branched chain), and more preferably 20 or fewer. Likewise, preferred cycloalkyls have from 3-10 carbon atoms in their ring structure, and more preferably have 5, 6 or 7 carbons in the ring structure.

Unless the number of carbons is otherwise specified, "lower alkyl" as used herein means an alkyl group, as defined above, but having from one to ten carbons, more preferably from one to six carbon atoms in its backbone structure. Likewise, "lower alkenyl" and "lower alkynyl" have similar chain lengths. Preferred alkyl groups are lower alkyls. In preferred embodiments, a substituent designated herein as alkyl is a lower alkyl.

The term "aralkyl", as used herein, refers to an alkyl group substituted with an aryl group (e.g., an aromatic or heteroaromatic group).

The terms "alkenyl" and "alkynyl" refer to unsaturated aliphatic groups analogous in length and possible substitution to the alkyls described above, but that contain at least one double or triple bond respectively.

The term "aryl" as used herein includes 5-, 6- and 7-membered single-ring aromatic groups that may include from zero to four heteroatoms, for example, benzene, naphthalene, anthracene, pyrene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics." The aromatic ring can be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings can be cycloalkyls, cycloalkenyls, cycloalkynyls, aryls and/or heterocyclyls.

The terms ortho, meta and para apply to 1,2-, 1,3- and 1,4-disubstituted benzenes, respectively. For example, the names 1,2-dimethylbenzene and ortho-dimethylbenzene are synonymous.

The terms "heterocyclyl" or "heterocyclic group" refer to 3- to 10-membered ring structures, more preferably 3- to 7-membered rings, whose ring structures include one to four heteroatoms. Heterocycles can also be polycycles. Heterocyclyl groups include, for example, azetidine, azepine, thiophene, thianthrene, furan, pyran, isobenzofuran, chromene, xanthene, phenoxathiin, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring can be substituted at one or more positions with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

The terms "polycyclyl" or "polycyclic group" refer to two or more rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

The term "carbocycle", as used herein, refers to an aromatic or non-aromatic ring in which each atom of the ring is carbon.

As used herein, the term "nitro" means —$NO_2$; the term "halogen" designates —F, —Cl, —Br or —I; the term "sulfhydryl" means —SH; the term "hydroxyl" means —OH; and the term "sulfonyl" means —$SO_2$—.

The terms "amine" and "amino" are art-recognized and refer to both unsubstituted and substituted amines, e.g., a moiety that can be represented by the general formula:

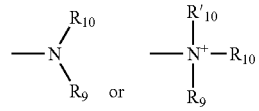

wherein $R_9$, $R_{10}$ and $R'_{10}$ each independently represent a group permitted by the rules of valence.

The term "acylamino" is art-recognized and refers to a moiety that can be represented by the general formula:

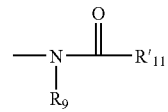

wherein $R_9$ is as defined above, and $R'_{11}$ represents a hydrogen, an alkyl, an alkenyl or —$(CH_2)_m$—$R_8$, where m and $R_8$ are as defined above.

The term "amido" is art recognized as an amino-substituted carbonyl and includes a moiety that can be represented by the general formula:

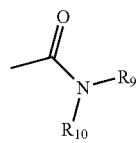

wherein $R_9$, $R_{10}$ are as defined above. Preferred embodiments of the amide will not include imides which may be unstable.

The term "alkylthio" refers to an alkyl group, as defined above, having a sulfur radical attached thereto. In preferred embodiments, the "alkylthio" moiety is represented by one of —S-alkyl, —S-alkenyl, —S-alkynyl, and —S—$(CH_2)_m$—$R_8$, wherein m and $R_8$ are defined above. Representative alkylthio groups include methylthio, ethyl thio, and the like.

The term "carbonyl" is art recognized and includes such moieties as can be represented by the general formula:

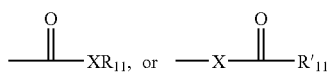

wherein X is a bond or represents an oxygen or a sulfur, and $R_{11}$ represents a hydrogen, an alkyl, an alkenyl, —$(CH_2)_m$—$R_8$ or a pharmaceutically acceptable salt, $R'_{11}$ represents a hydrogen, an alkyl, an alkenyl or —$(CH_2)_m$—$R_8$, where m and $R_8$ are as defined above. Where X is an oxygen and $R_{11}$ or $R'_{11}$ is not hydrogen, the formula represents an "ester". Where X is an oxygen, and $R_{11}$ is as defined above, the moiety is referred to herein as a carboxyl group, and particularly when $R_{11}$ is a hydrogen, the formula represents a "carboxylic acid". Where X is an oxygen, and $R'_{11}$ is hydrogen, the formula represents a "formate". In general, where the oxygen atom of the above formula is replaced by sulfur, the formula represents a "thiolcarbonyl" group. Where X is a sulfur and $R_{11}$ or $R'_{11}$ is not hydrogen, the formula represents a "thiolester." Where X is a sulfur and $R_{11}$ is hydrogen, the formula represents a "thiolcarboxylic acid." Where X is a sulfur and $R'_{11}$ is hydrogen, the formula represents a "thiolformate." On the other hand, where X is a bond, and $R_{11}$ is not hydrogen, the above formula represents a "ketone" group. Where X is a bond, and $R_{11}$ is hydrogen, the above formula represents an "aldehyde" group.

The terms "alkoxyl" or "alkoxy" as used herein refers to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as can be represented by one of —O-alkyl, —O-alkenyl, —O-alkynyl, —O—$(CH_2)_m$—$R_8$, where m and $R_8$ are described above.

The abbreviations Me, Et, Ph, Ti, Ni, Ts, Ms represent methyl ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the *Journal of Organic Chemistry*; this list is typically presented in a table entitled *Standard List of Abbreviations*. The abbreviations contained in said list, and all abbreviations utilized by organic chemists of ordinary skill in the art are hereby incorporated by reference.

Analogous substitutions can be made to alkenyl and alkynyl groups to produce, for example, aminoalkenyls, aminoalkynyls, amidoalkenyls, amidoalkynyls, iminoalkenyls, iminoalkynyls, thioalkenyls, thioalkynyls, carbonyl-substituted alkenyls or alkynyls.

As used herein, the definition of each expression, e.g. alkyl, m, n, etc., when it occurs more than once in any structure, is intended to be independent of its definition elsewhere in the same structure.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc.

As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

The phrase "protecting group" as used herein means temporary substituents which protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M *Protective Groups in Organic Synthesis*, $2^{nd}$ ed.; Wiley: New York, 1991).

Certain compounds of the present invention may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as failing within the scope of the invention. Additional asymmetric carbon atoms may be present in a substituent such as an alkyl group. All such isomers, as well as mixtures thereof, are intended to be included in this invention.

If, for instance, a particular enantiomer of a compound of the present invention is desired, it may be prepared by asymmetric synthesis, it may be isolated using chiral chromatography methods, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

Contemplated equivalents of the compounds described above include compounds which otherwise correspond thereto, and which have the same general properties thereof (e.g., functioning as analgesics), wherein one or more simple variations of substituents are made which do not adversely affect the efficacy of the compound in binding to opioid receptors. In general, the compounds of the present invention may be prepared by the methods illustrated in the general reaction schemes as, for example, described below, or by modifications thereof using readily available starting materials, reagents and conventional synthesis procedures. In these reactions, it is also possible to make use of variants which are in themselves known, but are not mentioned here.

For purposes of this invention, the chemical elements are identified in accordance with the Periodic Table of the Elements, CAS version, Handbook of Chemistry and Physics, 67th Ed., 1986-87, inside cover.

DISCUSSION OF SELECTED PREFERRED EMBODIMENTS

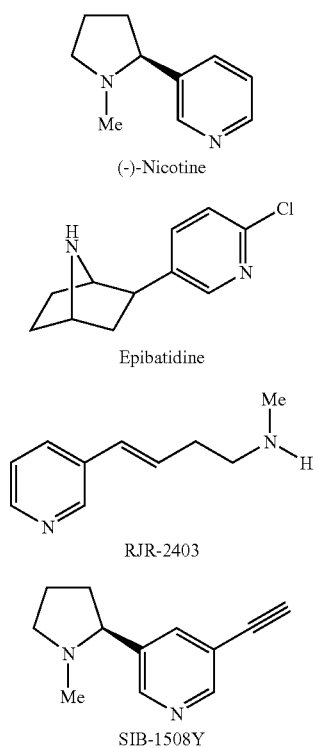

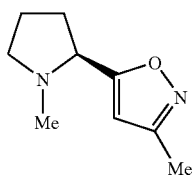

ABT-418 (5)

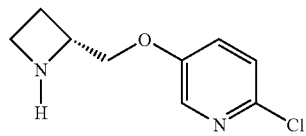

ABT-594 (6)

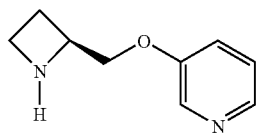

A-85380 (7)

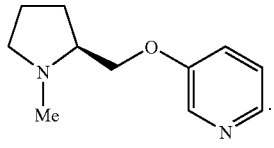

A-84543 (8)

It has been shown that C-5 position of the pyridyl moiety of A-84543 (8) could tolerate sterically bulky substituents without losing the binding affinity at α4β2 nAChR. We investigated the effects of the C-5 substituents of the pyridine on the binding affinity and subtype-selectivity at neuronal nicotinic acetylcholine receptors caused by the steric factor as well as the hydropathy profile of the introduced group. In the nicotinic series, introduction of an ethynyl substituent at the C-5 position of the pyridyl ring lead to SIB-1508Y (4) with altered subtype selectivity for neuronal nAChRs. Thus, a series of 5-alkynyl substituted A-84543 analogues 11-17 were prepared in good yields from 5-bromo derivative 10 by Pd—C catalyzed Sonogashira reaction in aqueous system (Scheme 1). The intermediate 10 was readily obtained by treatment of 3,5-dibromopyridine with (S)-1-methyl-2-pyrrolidinyl-methanol (9) in the presence of sodium hydride. The 5-ethynyl derivative 19 was prepared by treatment 12 with NaH. Catalytic hydrogenation of 10 and 16 on Pd—C provided 8 and 19, respectively.

Scheme 1.ª

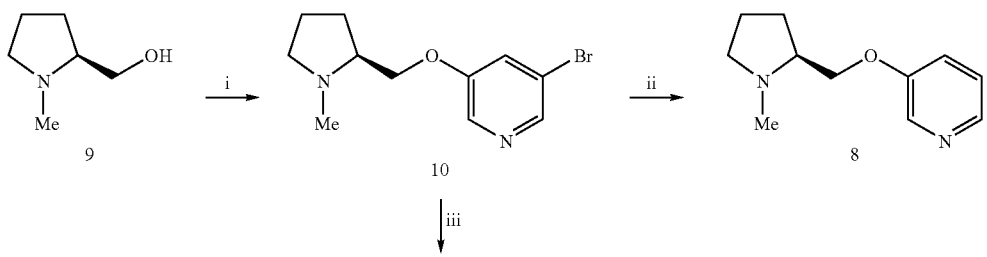

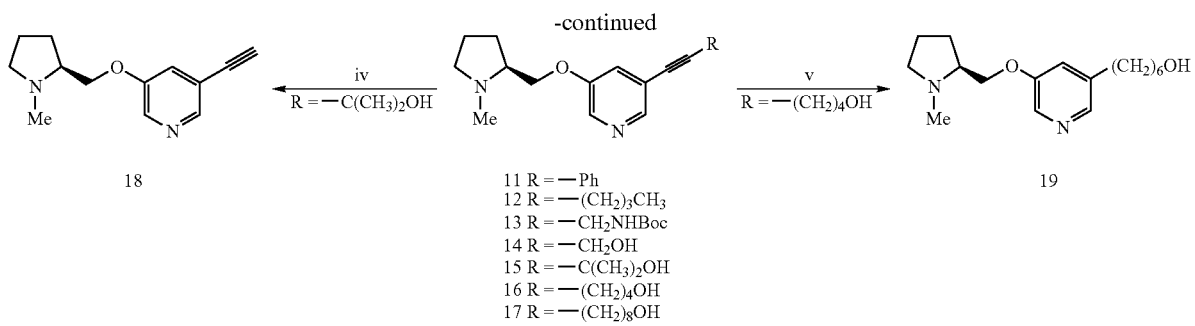

11 R = —Ph
12 R = —(CH$_2$)$_3$CH$_3$
13 R = —CH$_2$NHBoc
14 R = —CH$_2$OH
15 R = —C(CH$_3$)$_2$OH
16 R = —(CH$_2$)$_4$OH
17 R = —(CH$_2$)$_8$OH

[a]Reagents: (i) NaH, DMF, then 3,5-dibromopyridine, room temperature, 70%; (ii) 10% Pd-C, EtOH, H$_2$ (1 atm), 99% (iii) Alkyne, 10% Pd-C (cat.), CuI (cat.), K$_2$CO$_3$, DME, H$_2$O, reflux, 72 h, 55-95%; (iv) NaH (cat.), toluene, 120° C., 1 h, 99%; (v) 10% Pd-C, EtOAc, H$_2$ (1 atm), 99%.

5-(6-Hydroxy-1-hexynyl) derivative 26 and N-demethyl analogue of 16 were synthesized as shown in Scheme 2. Treatment of the alcohols 20 and 21 with 3-bromo-5-hydroxypyridine under Mitsunobu conditions provided the corresponding 3-pyridyl ethers 22 and 23, which were coupled with 5-hexyn-1-ol under the Pd—C catalyzed Sonogashira reaction protocol to afford the corresponding 24 and 25 in good yield. Removal of the Boc protection groups in 24 and 25 provided 26 and 27, respectively.

Scheme 2[a]

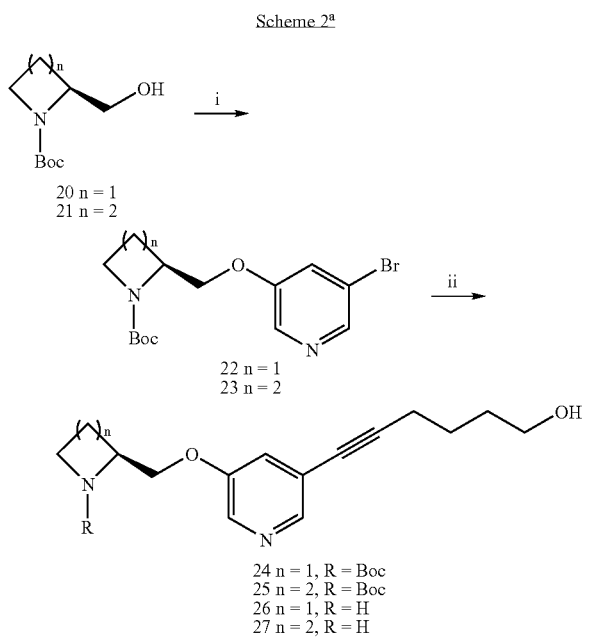

24 n = 1, R = Boc
25 n = 2, R = Boc
26 n = 1, R = H
27 n = 2, R = H

[a]Reagents: (i) 3-Brom-5-hydroxypyridine, PPh$_3$, DEAD, THF, room temperature, 81-85%; (ii) a) 5-Hexyn-1-ol, 10% Pd-C (cat.), CuI (cat.), K$_2$CO$_3$, DME, H$_2$O, reflux, 72 h, 83-95%; b) CF$_3$CO$_2$H, CH$_2$Cl$_2$, 85-93%.

Two epibatidine analogues 31 and 34 were prepared as shown in Schemes 3 and 4, respectively. Reductive Heck reaction of the olefin 28 with 3,5-dibromopyridine provided 29, which was coupled with 6-[(tert-butyldimethylsilyl)oxy]-1-hexyne under the catalysis with Pd(PPh$_3$)Cl$_2$ and CuI to give 30. Removal of the TBS and Boc protection groups together with trifluoroacetic acid provided 5-(6-hydroxy-1-hexynyl) substituted dechloroepibatidine analogue 31 (Scheme 3). 6-(6-Hydroxy-1-hexynyl) substituted epibatidine analogue 34 were prepared from 32 in a similar manner (Scheme 4).

Scheme 3[a]

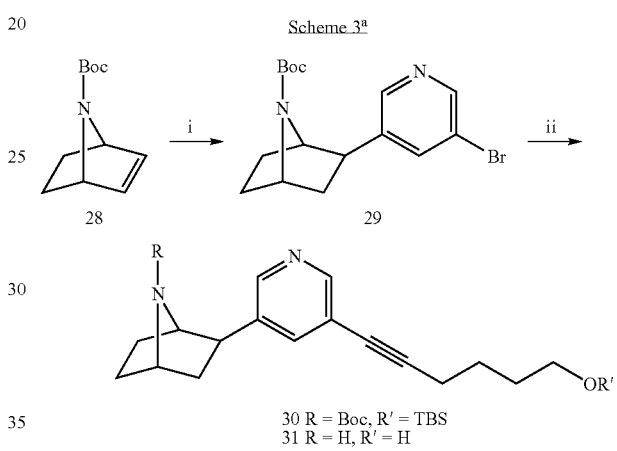

30 R = Boc, R' = TBS
31 R = H, R' = H

[a]Reagents: (i) 3,5-Dibromopyridine, Pd (PPh$_3$)$_4$ (cat.), piperidine, HCO$_2$H, DMF, 80° C., 72 h, 61%; (ii) a) 6-[(tert-Butyldimethylsilyl)oxy]-1-hexyne, Pd (PPh$_3$)$_2$Cl$_2$, CuI, Bu$_4$NI, Et$_3$N, DMF, reflux; 48 h, 93%; b) CF$_3$CO$_2$H, CH$_2$Cl$_2$, 90%.

Scheme 4[a]

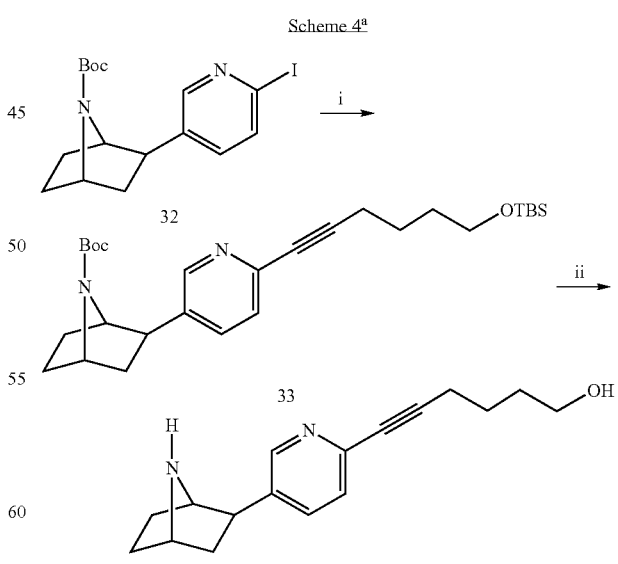

[a]Reagents: (i) 6-[(tert-Butyldimethylsilyl)oxy]-1-hexyne, Pd (PPh$_3$)$_2$Cl$_2$, CuI, Bu$_4$NI, Et$_3$N, DMF, room temperature, 24 h; then 60° C., 24 h, 94%; (ii) CF$_3$CO$_2$H, CH$_2$Cl$_2$, 81%.

Three fluorine-containing 3-pyridyl ether analogues 36, 41, and 42 were also prepared, in particular, with the expectation that they could serve for PET imaging purposes if appropriately labeled with $^{18}F$. 5-(6-Fluoro-1-hexynyl) derivative 36 was prepared from the alcohol 16 by treatment with iodine in the presence of $PPh_3$ and imidazole, followed by silver fluoride (Scheme 5). Tosylation of the alcohols 24 and 25 provided the corresponding tosylates 37 and 38. Treatment of 37 and 38 with tetrabutylammonium fluoride followed by trifluoroacetic acid gave 41 and 42, respectively, in good yields (Scheme 6).

Scheme 5[a]

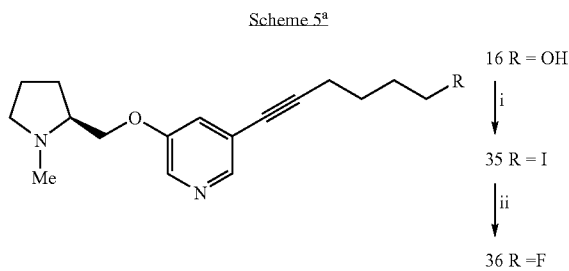

16 R = OH
35 R = I
36 R = F

[a]Reagents: (i) $I_2$, $PPh_3$, imidazole, $CH_2Cl_2$, 92%; (ii) AgF, acetonitrile, room temperature, 10 h, 57%.

Scheme 6[a]

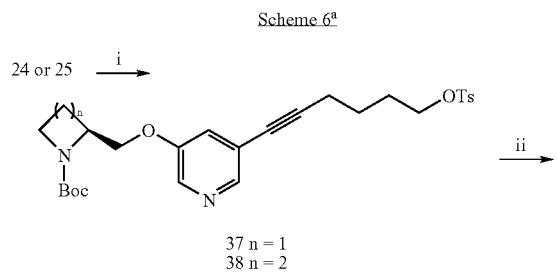

24 or 25

37 n = 1
38 n = 2

39 n = 1, R = Boc
40 n = 2, R = Boc
41 n = 1, R = H
42 n = 2, R = H

[a]Reagents: (i) p-TsCl, $Et_3N$, DMAP (cat.), $CH_2Cl_2$, 75-82%; (ii) a) Tetrabutylammonium fluoride (1 M in THF), room temperature, 10-15 h, 97-100%; b) $CF_3CO_2H$, $CH_2Cl_2$, 87-93%.

In order to assess the steric and hydropathic effects of the C-5 substituents of the pyridine on the binding affinity and subtype-selectivity at neuronal nicotinic acetylcholine receptors. A series of A-84543 analogues 10-19 were evaluated by their binding assays at the six heterologously expressed nAChR subtypes (α2β2, α2β4, α3β2, α3β4, α4β2, and α4β4) and at receptors in rat forebrain. The results are summarized in Table 1. The binding affinity ratios for a ligand, calculated from its affinities at an α subunit paired with either the β2 osubunit or the β4 subunit, represents a measure of the selectivity of that ligand with regard to the β subunits. These ratios are shown in Table 2. We also compared the affinities of these agonists for the heterologously expressed α3β4 subunit combination to their affinities for the rat forebrain receptor. An α3β4 subtype is found in many sympathetic ganglia, while an α4β2 subtype is the predominant receptor in rat forebrain; therefore, the affinity ratios of drugs at these subtypes can help to predict the likelihood of possibly limiting autonomic nervous system side effects of drugs aimed at the predominant receptor in forebrain.

TABLE 1

Binding affinities ($K_i$, nM) of (−)-nicotine (1), (±)-epibatidine (2) and 3, 4, 6-8, 11, 12 at heterologously expressed nAChR subtypes and rat forebrain[a]

| | | $K_i$ (nM) | | | | | | |
|---|---|---|---|---|---|---|---|---|
| Ligand | R= | α2β2 | α2β4 | α3β2 | α3β4 | α4β2 | α4β4 | Rat forebrain |
| 1 | N/A | 12 | 112 | 47 | 443 | 10 | 40 | 13 |
| 2 | N/A | 0.025 | 0.095 | 0.035 | 0.565 | 0.061 | 0.157 | 0.060 |
| 7 | N/A | 0.073 | 18.4 | 0.208 | 77.7 | 0.142 | 8.04 | 0.248 |
| 8 | —H | 1.07 | 209.0 | 9.04 | 835.0 | 1.40 | 205.0 | 5.15 |
| 10 | —Br | 1.32 | 546 | 29.3 | 2,040 | 1.56 | 345 | 7.24 |

TABLE 1-continued

Binding affinities ($K_i$, nM) of (−)-nicotine (1), (±)-epibatidine (2) and 3, 4, 6-8, 11, 12 at heterologously expressed nAChR subtypes and rat forebrain[a]

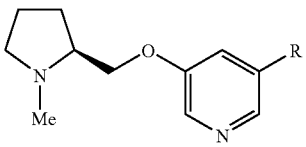

| Ligand | R= | | $K_i$(nM) | | | | | |
|---|---|---|---|---|---|---|---|---|
| | | α2β2 | α2β4 | α3β2 | α3β4 | α4β2 | α4β4 | Rat forebrain |
| 18 | —C≡CH | 0.75 | 434 | 10.7 | 3,080 | 1.02 | 473 | 3.65 |
| 11 | ≡—Ph | 4.52 | 437 | 4.96 | 2,460 | 0.936 | 369 | 6.40 |
| 12 | ≡—(CH$_2$)$_3$Me | 13.4 | 1,720 | 20.3 | 9,560 | 2.61 | 1410 | 6.81 |
| 13 | ≡—CH$_2$NHBoc | 1.19 | 8,240 | 7.27 | 59,900 | 2.07 | 8280 | 3.71 |
| 14 | ≡—CH$_2$OH | 2.43 | 1,880 | 7.64 | 18,200 | 0.954 | 1690 | 3.16 |
| 15 | ≡—C(Me)$_2$OH | 1.93 | 5,890 | 19.70 | 32,600 | 1.34 | 5060 | 8.39 |
| 16 | ≡—(CH$_2$)$_4$OH | 2.87 | 3,230 | 12.6 | 40,200 | 0.81 | 1270 | 3.56 |
| 17 | ≡—(CH$_2$)$_8$OH | 26.8 | 7,800 | 52.1 | 62,700 | 6.50 | 3560 | 21.70 |
| 19 | —(CH$_2$)$_6$OH | 3.33 | 1,150 | 13.40 | 20,000 | 0.75 | 968 | 5.39 |

[a]$K_d$ values (nM) for [$^3$H]-epibatidine used for calculating $K_i$ values were 0.02 for α2β2, 0.08 for α2β4, 0.03 for α3β2, 0.30 for α3β4, 0.04 for α4β2 and 0.09 for α4β4. The $K_i$ values of (−)-nicotine (1) and epibatidine (2) shown were the mean of 3 to 6 independent measurements. The $K_i$ values of 7,8, and 10-19 shown were the mean of 3 independent measurements.

TABLE 2

Binding affinity ratios for nAChR α subunits paired with
β2 or β4 subunits and
the α3β4 subunit combination versus the rat forebrain (primary α4β2)

| Ligand | Affinity ratio[a] | | | | cLogP[b] |
|---|---|---|---|---|---|
| | α2β4/ α2β2 | α3β4/ α3β2 | α4β4/ α4β2 | α3β4/ Forbrain | |
| 1 | 9 | 9 | 4 | 34 | 0.88 |
| 2 | 4 | 16 | 3 | 9 | 1.55 |
| 7 | 252 | 374 | 57 | 313 | 0.725 |
| 8 | 195 | 92 | 146 | 162 | 1.83 |
| 10 | 414 | 70 | 221 | 282 | 2.73 |
| 18 | 579 | 288 | 464 | 844 | 2.10 |
| 11 | 97 | 496 | 423 | 384 | 4.47 |
| 12 | 128 | 471 | 540 | 1,404 | 4.08 |
| 13 | 6,924 | 8,240 | 4,000 | 16,146 | 2.48 |
| 14 | 774 | 2,382 | 1,772 | 5,760 | 0.64 |
| 15 | 3,052 | 1,655 | 3,776 | 3,886 | 1.35 |
| 16 | 1,125 | 3,190 | 1,568 | 11,292 | 2.23 |
| 17 | 291 | 1,203 | 548 | 2,890 | 4.34 |
| 19 | 345 | 1,493 | 1,290 | 3,710 | 2.99 |

[a] Ratio of the corresponding $K_i$ values.
[b] http://www.daylight.coin/daycgi/clogp.

As shown in Tables 1 and 2, neither nicotine (1) nor epibatidine (2) shows any significant selectivity among the six rat nAChR subtypes and rat forebrain (<45-fold). A-85380 (7) and A-84543 (8) possessed very high affinity for all three of the nAChR subtypes containing β2 subunits but much lower affinity for the subtypes containing β 4 subunits, although the best selectivities among the six nAChR subtypes and rat forebrain are still less than 400-fold. The improved selectivity suggests the possibility of developing subtype-selective ligands and therapeutically useful drugs. As a matter of fact, 7 and 8, as the novel lead compounds, have caused extensive investigation since their discovery in the mid 1990s. Introduction of additional substituent groups at the C5 position of the pyridyl ring of 8 resulting 10-19 didn't cause any significant difference on the binding affinities at the α4β2 containing subtype or the rat forebrain (within 5-fold). These results are in accord with the previous conclusion that the C5 position of the pyridyl ring of 8 could tolerate substitutions without losing affinity for α4β2 receptor subtype. However, it is noteworthy that the subtype selectivities of the derivatives 10-19 among the six heterologously expressed neuronal nAChR subtypes and rat forebrain are much dependent on the properties of the substituent groups. First of all, the presence of a bulky substitutions at the C5 position of pyridyl part slightly improved the nAChR subtype selectivity for α4β2 or the receptors in rat forebrain over the ganglionic α3β4, although the steric volume of substitutions has little effect on α4β2 nAChR binging affinity. Secondly, the ligands 13-17 and 19 with appendages containing additional polar groups, such as hydroxyl group and amide group, show significantly improved affinity ratios, e.g. α2β4/α2β2, α3β4/α3β2, α4β4/α4β2, and α3β4/forbrain, in comparison to 8. For example, the affinity ratios, as compared in Table 2, for 13 are over 4000 and up to 16,000. These high active and selective analogues containing to appropriately functionalized side-chain appendages are quite interesting, because in addition to their general use as pharmacological tools, they can be used to make fluorescent probes and affinity columns for certain nAChR subtypes, as well as for PET imaging study after labeled with $^{11}$C or $^{18}$F. The 5-(6-hydroxy-1-hexynyl) derivative 16 is one of the best ligands possessing not only high affinity for the α4β2 subtype but also high selectivity among the nAChR subtypes compared. Its analogue 17 with a prolonged (10-carbon) side-chain appendage shows both lower affinity and less subtype selectivity at the six heterologously expressed nAChR subtypes and rat forebrain. The saturated analogue 19 shows similar binding affinities for the 132 containing subtypes as those of 16, but the former is a little less selective.

The 6-hydroxy-1-hexynyl substituent at the CS position of the pyridine ring of 16 is an optimum group for attaining both the expected high binding affinity at the α4β2 receptor and the excellent subtype-selectivity. Therefore, 5-(6-hydroxy-1-hexynyl) substituted A-85380 analogue 26, N-demethyl 5-(6-hydroxy-1-hexynyl) substituted A-84543 analogue 27 were prepared and evaluated at the six defined rat nicotinic receptor subtypes and rat forebrain. The binding affinity results, together with the subtype selectivity of α3β4 vs the receptors in rat forebrain, are summarized in Table 3. The N-demethyl derivative 27 shows a little higher not only binding affinities at the nAChR subtypes but also subtype selectivity of α3β4 vs rat forebrain than its N-methyl analogue 16. Similar to 16 and 27, the four-membered ring analogue 26 possessed much higher affinities at receptors composed of an α subunit in combination with the β2 subunit than the β4 subunit. In fact, 26 is the most selective nAChR agonist known at α4β2 vs ganglionic α3β4 receptors (54,000-fold) while possessed the similar high binding affinity as epibatidine (2) and A-85380 (7) at the α4β2 subtype.

TABLE 3

Binding affinities ($K_i$, nM) of 16, 26, 27, 31, 34, 36, 41, 42 at heterologously expressed nAChR subtypes and rat forebrain[a]

| Ligand | $K_i$ (nM) | | | | | | | Affinity ratio | cLogP[c] |
|---|---|---|---|---|---|---|---|---|---|
| | α2β2 | α2β4 | α3β2 | α3β4 | α4β2 | α4β4 | Forebrain | (α3β4/Forbrain)[b] | |
| 16 | 2.87 | 3,230 | 12.6 | 40,200 | 0.81 | 1270 | 3.56 | 11,292 | 2.23 |
| 26 | 0.06 | 269 | 0.53 | 4,840 | 0.09 | 74 | — | 53,778 | 1.12 |
| 27 | 1.51 | 835 | 2.69 | 16,100 | 0.665 | 778 | 1.15 | 14,000 | 1.68 |
| 31 | 0.352 | 45.10 | 0.146 | 266.0 | 0.166 | 15.40 | 0.215 | 1,237 | 1.15 |
| 34 | 16.90 | 67.40 | 19.8 | 95.40 | 67.70 | 61.80 | 52.00 | 2 | 1.15 |
| 36 | | | | | | | | | 3.49 |
| 41 | 0.796 | 197 | 0.635 | 5,490 | 0.201 | 118 | 0.362 | 15,166 | 2.38 |
| 42 | 3.50 | 680 | 5.27 | 7,580 | 0.907 | 721 | 3.45 | 2,197 | 2.94 |

[a] $K_i$ values (nM) for [$^3$H]-epibatidine used for calculating $K_i$ values were 0.02 for α2β2, 0.08 for α2β4, 0.03 for α3β2, 0.30 for α3β4, 0.04 for α4β2 and 0.09 for α4β4. The $K_i$ values were the mean of 3 independent measurements.
[b] Ratio of the corresponding $K_i$ values.
[c] http://www.daylight.com/daycgi/clogp.

If epibatidine (2) and the 3-pyridyl ethers 7 and 8 bind at nAChRs in common manners, the significant improvement of the subtype selectivity of 16, 26, and 27 by introducing a bulky hydrophilic 6-hydroxy-1-hexynyl group at the C5 position of the pyridyl ring should also apply to the corresponding epibatidine analogues. It is noteworthy that, although a lot of epibatidine analogues have been prepared with the expectation to improve their subtype selectivity, in most reports, pharmacological investigations, if conducted at all, are limited to measurements at the α4β2 receptor or only one or two other nAChR subtypes. A very recent study reveals that introduction of a bulky phenyl group at the C5 position of the pyridyl ring of epibatidine results in ligands with antagonist action. On the other hand, it has been shown that dechloroepibatidine binds with similar affinity as epibatidine at the α4β2 nAChR subtype. Thus, the 5-(6-hydroxy-1-hexynyl) substituted dechloroepibatidine analogues 31 was prepared and evaluated at the six rat nicotinic receptor subtypes and rat forebrain. As shown in Table 3, 31 also possessed subnanomolar affinities at the β2 containing subtypes although there are 3-14 folds less active than epibatidine (2) at each β2 containing subtypes. It is noteworthy that 31 was quite selective for an α subunit paired with the β2 versus the β4 subunit, and the affinity ratios were up to 1,800. While epibatidine itself activates and binds to most nAChR subtypes with picomolar affinity (K; ratios less than 20). 6-(6-Hydroxy-1-hexynyl) substituted dechloroepibatidine analogue 34, 200-1000 folds lower binding affinities than epibatidine at the nAChRs, didn't show much subtype selectivity among the neuronal nAChRs interest (less than 6-fold). This result is in agreement with the previous results that introduction of a bulky substituent at C6-position of the pyridine ring of both epibatidine and nicotine resulted in markedly decreased nAChR binding affinities. Together with the present results, we can conclude that the nicotine analogues, epibatidine analogues, and the 3-pyridyl ether analogues herein are binding in a similar fashion at the nAChRs. The C5-position, if not the only position, of the pyridyl ring of nicotine, epibatidine, and the 3-pyridyl ether analogues (e.g. 7 and 8) could tolerate an additional large polar group to obtain significant subtype selectivity without losing the binding affinity at the α4β2 subtype.

All of the three fluoride analogues of 16, 26, and 27, i.e. compounds 36, 41, and 42, show not only subnanomolar affinities for α4β2 nAChR subtype but also excellent selectivities (up to 15,000-fold) for the receptors in rat forebrain over α3β4 subtype. The excellent receptor affinity and subtype selectivity of these fluoride analogues are very useful as they are potential agents for PET imaging study in the diagnosis of certain CNS disorders. It is noteworthy that the selective ligands 14-16 could also be extremely useful for the PET imaging study by labeling the N-methyl as $^{11}$C-methyl, as these ligands with lower lipophilicity (lower cLogP values) which is desirable to decrease nonspecific binding of the radioligands.

The therapeutic potential of nicotinic ligands depends substantially on the ability to affect selectively certain receptor subtypes with beneficial effects. While nicotine, epibatidine, and some 3-pyridyl ethers show good affinity for the neuronal nAChRs, they generally lack selectivity. Along with our objective in the design of subtype selective nAChR ligands, we discovered that introduction of a bulky hydrophilic group, like 6-hydroxy-1-hexynyl, at the C5 position of the pyridyl ring of nicotine (1), epibatidine (2), and the 3-pyridyl ether analogues (7 and 8) could significantly improve nAChR subtype selectivity at receptors composed of an α subunit in combination with the β2 subunit than the β4 subunit without losing the binding affinities at the α4β2 subtype. For example, compounds 26, 27, and 31 were 2 orders of magnitude more selective for α4β2 over α3β4 than the corresponding parent compounds 7, 8, and 2. These ligands with high affinity and selectivity are quite interesting because, in addition to their general use as pharmacological tools, they containing appropriately functionalized side-chain appendages could be used to make fluorescent probes and affinity columns for certain nAChR subtypes. In light of the high affinity and selectivity found for ligands 14-16 and the fluorinated analogues 36, 41, and 42, their use in brain PET imaging studies is an aspect of the present invention.

Synthesis of Compounds

The compounds of the invention may be prepared by any conventional method useful for the preparation of analogous compounds and as described in the examples below.

Starting materials for the processes described in the present patent application are known or can be prepared by known processes from commercially available materials.

A compound of the invention can be converted to another compound of the invention using conventional methods.

The products of the reactions described herein are isolated by conventional means such as extraction, crystallization, distillation, chromatography, and the like.

Examples of the nicotinic ACh receptor ligands of the present invention may be prepared by the general methods described in the Schemes hereinafter.

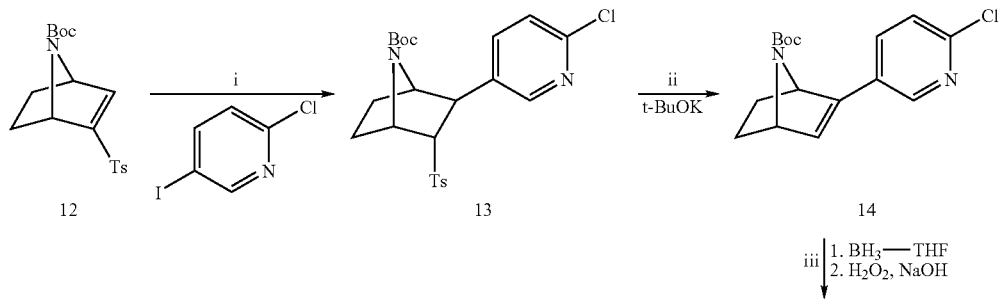

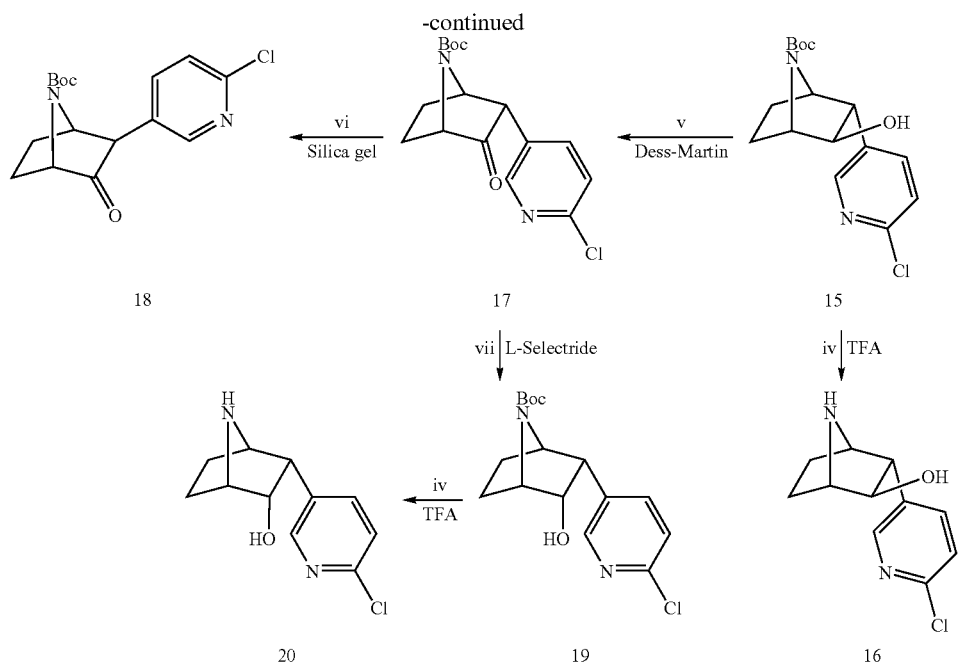

Reagents and conditions: (i) 2-chloro-5-iodopyridine, n-BuLi, THF, -78° C., 86%. (ii) t-BuOK, THF, -78° C. to rt, 2 h, 98%. (iii) BH₃·THF, THF, rt, overnight, then aq. NaOH, 35% H₂O₂, 39%. (iv) CF₃COOH, CH₂Cl₂, rt, 3 h. (v) Dess-Martin periodinane, CH₂Cl₂, rt, 96%. (vi) silica gel, rt, 2 days. (vii) L-Selectride, THF, -30 to 0° C., 91%.

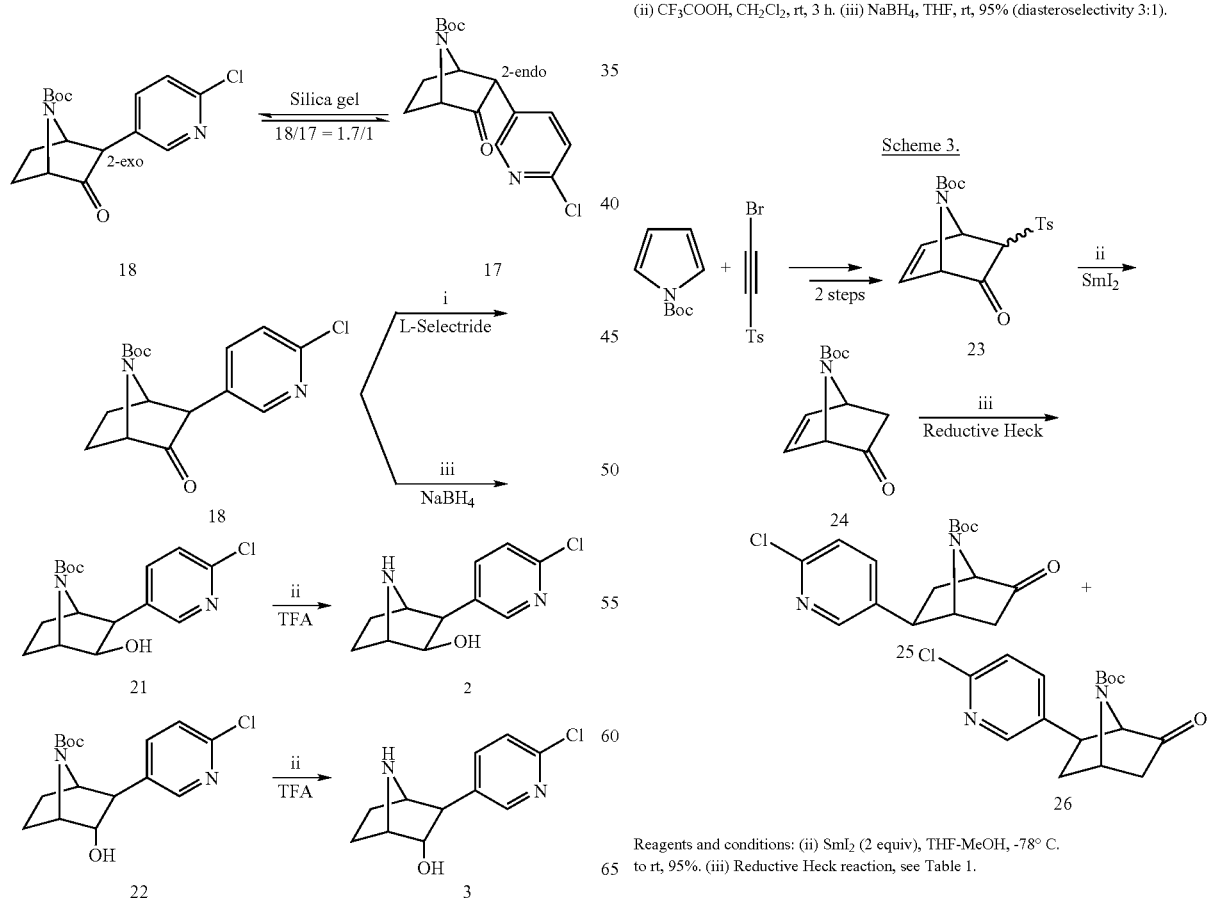

Reagents and conditions: (i) L-Selectride, THF, -30 to 0° C., 92%. (ii) CF₃COOH, CH₂Cl₂, rt, 3 h. (iii) NaBH₄, THF, rt, 95% (diastereoselectivity 3:1).

Reagents and conditions: (ii) SmI₂ (2 equiv), THF-MeOH, -78° C. to rt, 95%. (iii) Reductive Heck reaction, see Table 1.

TABLE 1

Reductive Heck reaction on 24 and 27

| Entry | Compound | Conditions | Products (ratio)[a] | Yield (%)[b] |
|---|---|---|---|---|
| 1 | 24 | Pd(OAc)$_2$, 2-chloro-5-iodopyridine, HCO$_2$Na, n-Bu$_4$NCl, DMF, 100 °C. | 25:26 (5.0:1) | 56 |
| 2 | 24 | Pd(OAc)$_2$(PPh)$_2$, 2-chloro-5-iodopyridine, piperidine, HCO$_2$H, DMF, 75° C. | 25:26 (2.5:1) | 38 |
| 3 | 24 | Pd(PPh)$_4$, 2-chloro-5-iodopyridine, piperidine, HCO$_2$H, DMF, 75° C. | 25:26 (0.9:1) | 47 |
| 4 | 27 | Pd(PPh)$_4$, 2-chloro-5-iodopyridine, piperidine, HCO$_2$H, DMF, 75° C. | 28:29 (12:1)[c] | 92 |

[a]Ratios were determined from the $^1$H NMR spectra of the product mixtures after chromatography.

[b]Overall yields were of isolated material after chromatography.

[c]Ratio was determined from the $^1$H NMR spectrum of the crude reaction products.

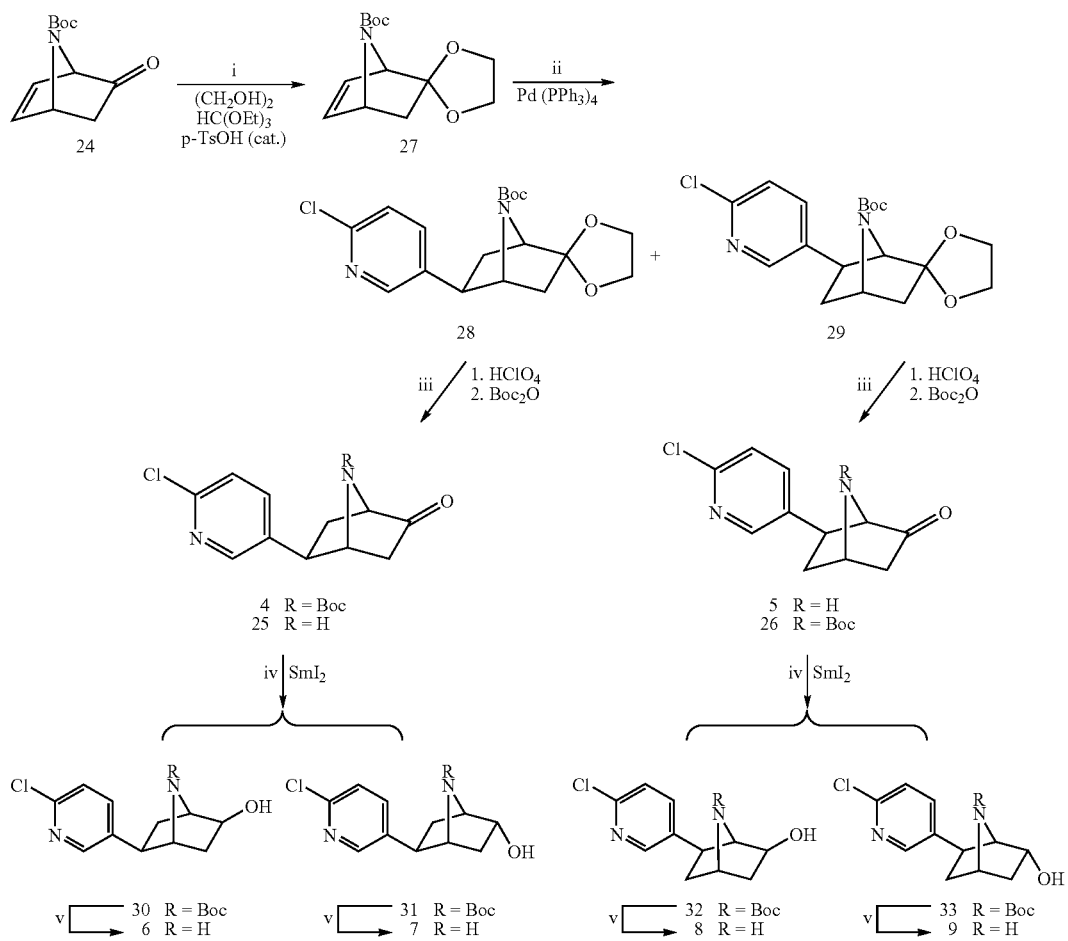

Scheme 4.

Reagents and conditions: (i) HOCH$_2$CH$_2$OH, (EtO)$_3$CH, p-TsOH (cat.), THF, 64%. (ii) 8, Pd (PPh$_3$)$_4$ (cat.), piperidine, HCO$_2$H, DMF, 75° C., 92%. (iii) 1. HClO$_4$; 2. Boc$_2$O, Et$_3$N, THF, 77-83% for two steps. (iv) see Table 2. (v) CF$_3$COOH, CH$_2$Cl$_2$, 93-97%.

Scheme 5.
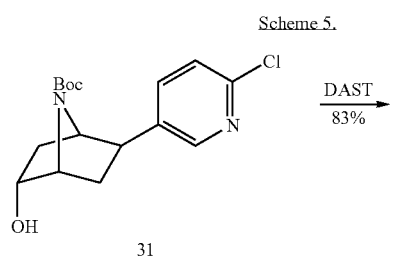
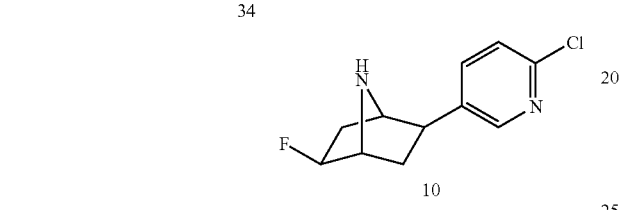
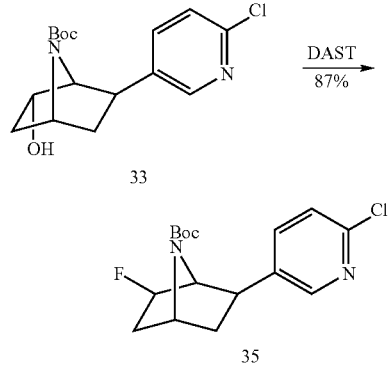
Scheme 6. Retrosynthesis.
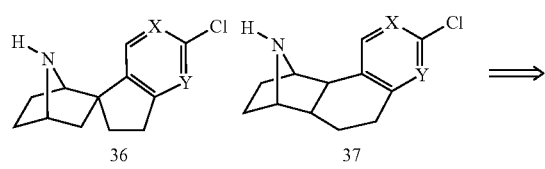
a: X = N, Y = CH
b: X = CH, Y = N
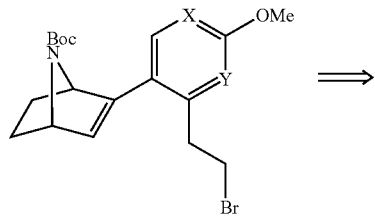
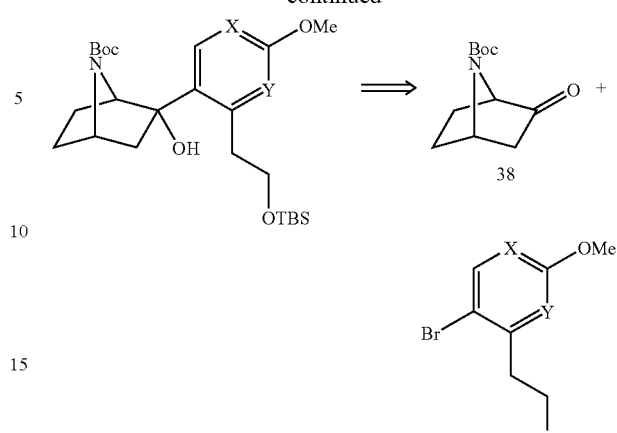
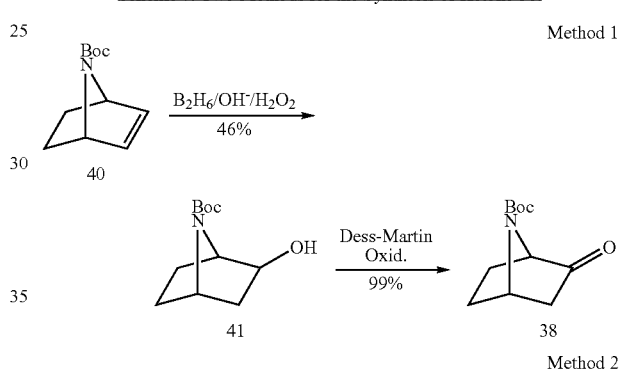
Scheme 7. Two Methods for the Synthesis of Ketone 38.
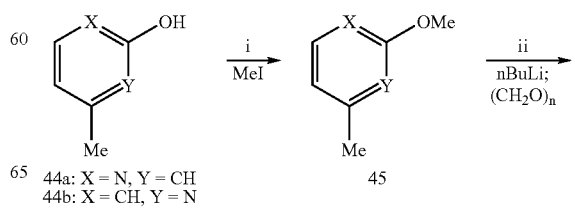
Scheme 8.

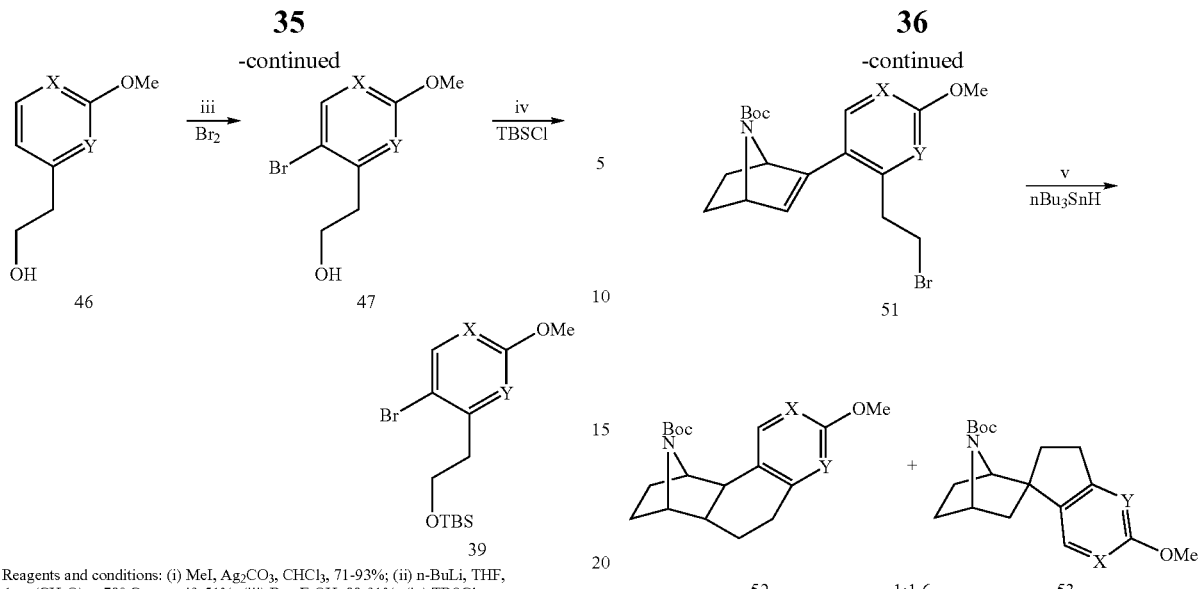
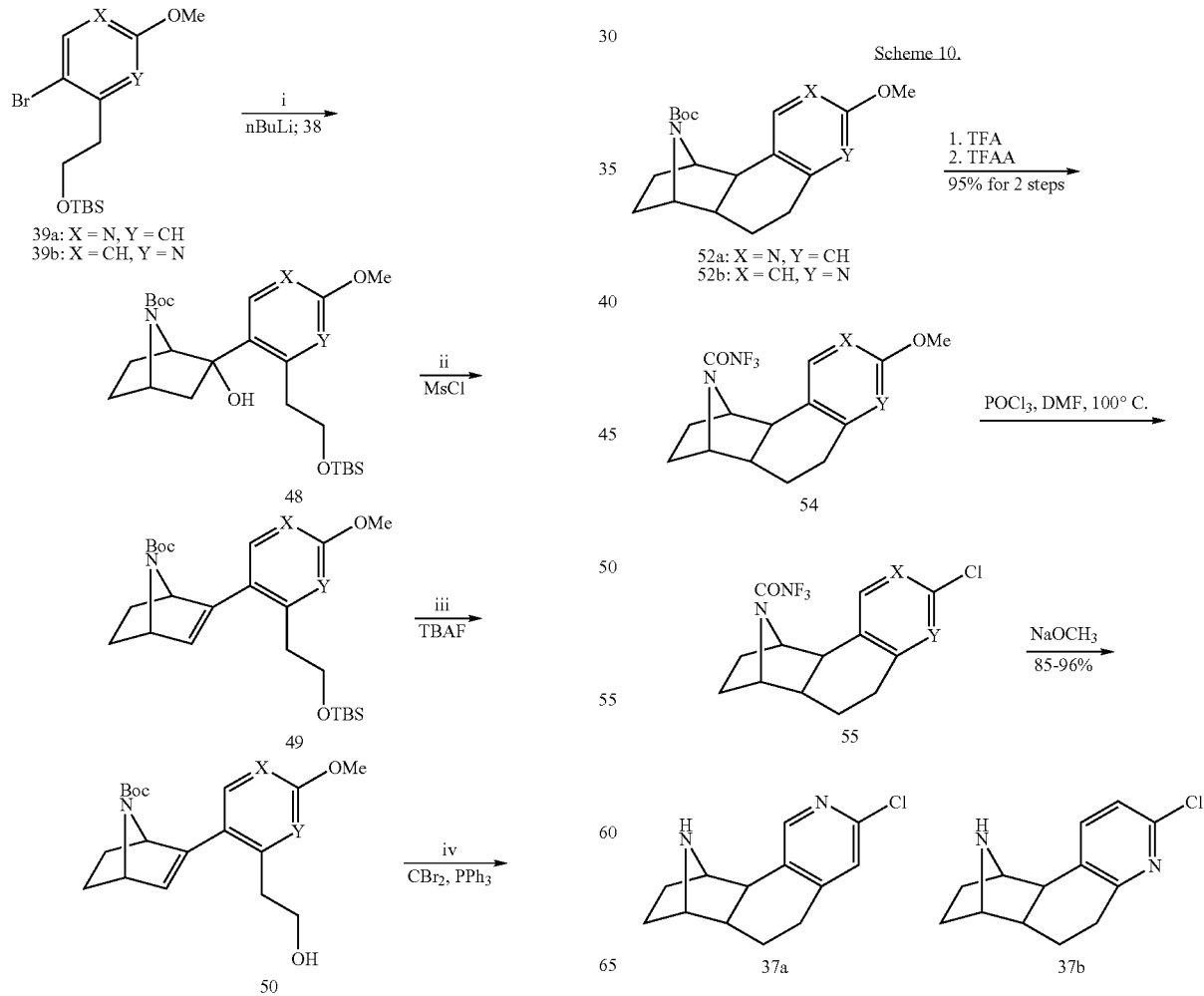

Scheme 11.

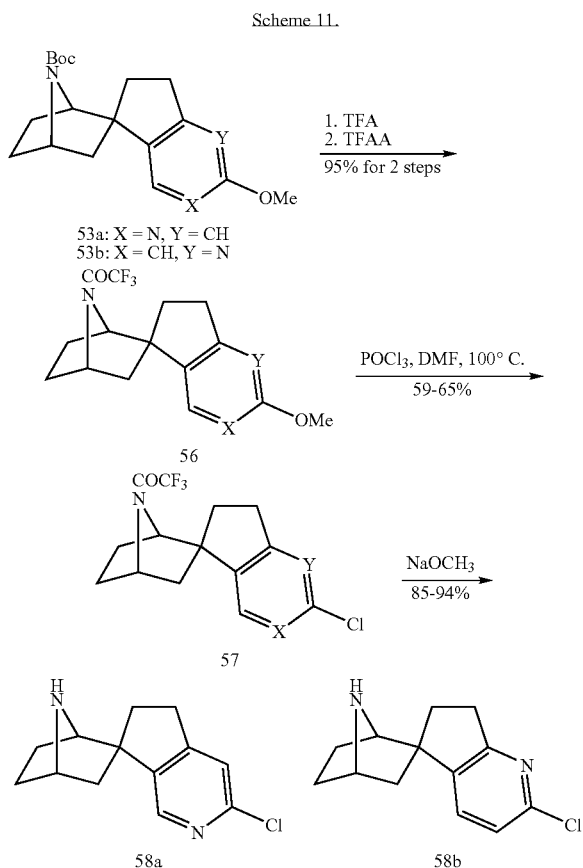

Binding Affinity Assays

Many different assay methods can be used to determine the activity of the compounds of the present invention. These assay methods include, for example, the following but also include other methods known to one of ordinary skill in the art.

Nicotinic ACh receptors in the brain are pentameric structures composed of subunits distinct from those found in skeletal muscles. The existence of eight α-subunits (α2-α9) and three β-subunits (β2-β4) in the mammalian brain has been described.

The predominant subtype with high affinity for nicotine is comprised of three α-subunits and two β-subunits.

The affinity of compounds of the invention for nicotinic ACh receptors may be investigated in three tests for in vitro inhibition of $^3$H-epibatidin binding, $^3$H-α-bungarotoxin binding and $^3$H-cytisine binding as described below:

In Vitro Inhibition of $^3$H-Cytisine Binding

The predominant subtype with high affinity for nicotine is comprised of α4 and β2 subunits. nAChRs of the latter type may selectively be labelled by the nicotine agonist $^3$H-cytisine.

Tissue Preparation: Preparations may be performed at 0-4° C. unless otherwise indicated. Cerebral corticies from male Wistar rats (150-250 g) may be homogenized for 20 sec in 15 mL Tris, HCl (50 mM, pH 7.4) containing 120 mM NaCl, 5 mM KCl, 1 mM MgCl2 and 2.5 mM CaCl2 using an Ultra-Turrax homogenizer. The homogenate may then be centrifuged at 27,000×g for 10 min. The supernatant may then be discarded and the pellet resuspended in fresh buffer and centrifuged a second time. The final pellet may be resuspended in fresh buffer (35 mL per g of original tissue) and used for binding assays.

Assay: Aliquots of 500 μl homogenate may be added to 25 μl of test solution and 25 μl of $^3$H-cytisine (1 nM, final

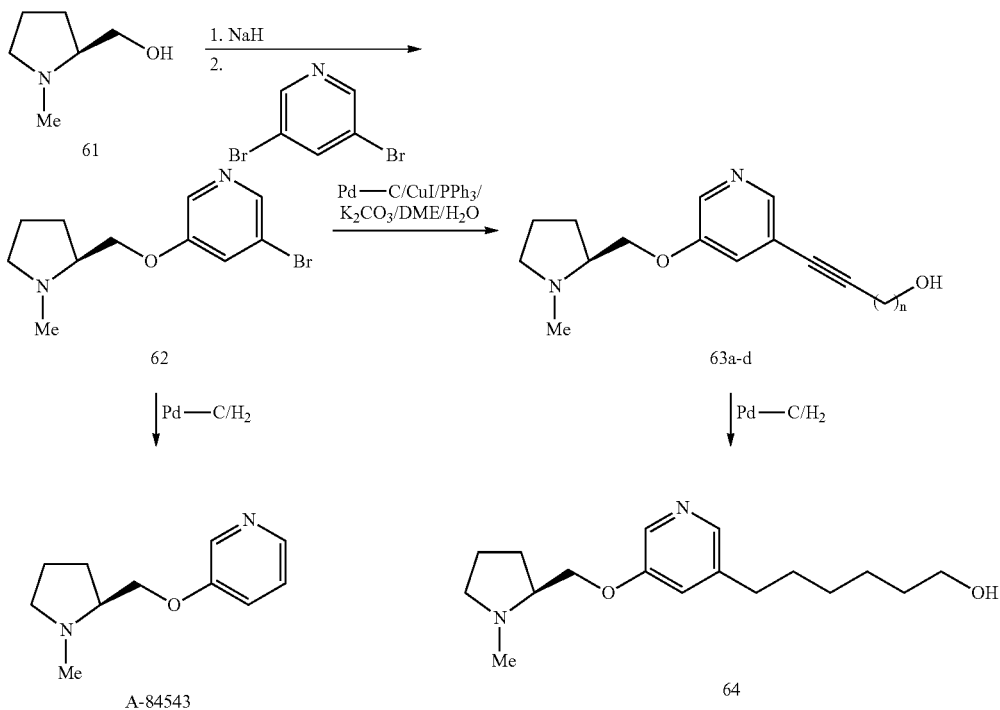

Scheme 12. Synthesis A-84543 analogs.

concentration), mixed and incubated for 90 min at 2° C. Non-specific binding may then be determined using (−)-nicotine (100 µM, final concentration). After incubation the samples may be added to 5 mL of ice-cold buffer and poured directly onto Whatman GF/C glass fiber filters under suction and immediately washed with 2×5 mL ice-cold buffer. The amount of radioactivity on the filters may then be determined by conventional liquid scintillation counting. Specific binding is total binding minus non-specific binding.

In Vitro Inhibition of $^3$H-α-Bungarotoxin Binding Rat Brain

α-Bungarotoxin is a peptide isolated from the venom of the Elapidae snake Bungarus multicinctus (Mebs et al., Biochem. Biophys. Res. Commun., 44(3), 711 (1971)) and has high affinity for neuronal and neuromuscular nicotinic receptors, where it acts as a potent antagonist. $^3$H-α-Bungarotoxin binds to a single site in rat brain with a unique distribution pattern in rat brain (Clarke et al., J. Neurosci. 5, 1307-1315 (1985)).

$^3$H-α-Bungarotoxin labels nAChR are formed by the α7 subunit isoform found in the brain and the isoform in the neuromuscular junction (Changeaux, Fidia Res. Found. Neurosci. Found. Lect. 4, 21-168 (1990). Functionally, the α7 homo-oligomer expressed in oocytes has a calcium permeability greater than neuromuscular receptors and, in some instances greater than NMDA channels (Seguela et al., J. Neurosci. 13, 596-604 (1993).

Tissue Preparation: Preparations may be performed at 0-4° C. unless otherwise indicated. Cerebral cortices from male Wistar rats (150-250 g) may be homogenized for 10 sec in 15 mL 20 mM Hepes buffer containing 118 mM NaCl, 4.8 mM KCl, 1.2 mM MgSO4 and 2.5 mM CaCl2 (pH 7.5) using an Ultra-Turrax homogenizer. The tissue suspension may then be centrifuged at 27,000×g for 10 min. The supernatant is discarded and the pellet is washed twice by centrifugation at 27,000×g for 10 min in 20 mL fresh buffer, and the final pellet may be resuspended in fresh buffer containing 0.01% BSA (35 mL per g of original tissue) and used for binding assays.

Assay: Aliquots of 500 µl homogenate may be added to 25 µl of test solution and 25 µl of $^3$H-α-bungarotoxin (2 nM, final concentration), mixed and incubated for 2 h at 37° C. Non-specific binding may then be determined using (−)-nicotine (1 mM, final concentration). After incubation the samples may be added to 5 mL of ice-cold Hepes buffer containing 0.05% PEI and poured directly onto Whatman GF/C glass fibre filters (presoaked in 0.1% PEI for at least 6 h) under suction and immediately washed with 2×5 mL ice-cold buffer. The amount of radioactivity on the filters may then be determined by conventional liquid scintillation counting. Specific binding is total binding minus non-specific binding.

In Vitro Inhibition of $^3$H-Epibatidin Binding

As discussed previously, Epibatidin is an alkaloid that was first isolated from the skin of the Ecuadoran frog Epipedobates tricolor and was found to have very high affinity for neuronal nicotinic receptors, where it acts as a potent agonist. It is believed that $^3$H-epibatidin binds to two sites in rat brain, both of which have pharmacological profiles consistent with neuronal nicotinic receptors and a similar brain regional distribution (Hougling et al., Mol. Pharmacol. 48, 280-287 (1995)).

The high affinity binding site for $^3$H-epibatidin is most certainly binding to the α4β2 subtype of nicotinic receptors. The identity of the low affinity site is still believed to be unknown. The inability of α-bungarotoxin to compete for $^3$H-epibatidin binding sites may indicate that neither site measured represents the nicotinic receptor composed of α7 subunits.

Tissue preparation: Preparations may be performed at 0-4° C. unless otherwise indicated. The forebrain (÷cerebellum) from a male Wistar rat (150-250 g) may be homogenized for 10-20 sec in 20 mL Tris, HCl (50 mM, pH 7.4) using an Ultra-Turrax homogenizer. The tissue suspension may then be centrifuged at 27,000×g for 10 min. The supernatant is then discarded and the pellet may then be washed three times by centrifugation at 27,000×g for 10 min in 20 mL fresh buffer, and the final pellet may be resuspended in fresh buffer (400 mL per g of original tissue) and used for binding assays.

Assay: Aliquots of 2.0 mL homogenate may be added to 0.100 mL of test solution and 0.100 mL of $^3$H-epibatidin (0.3 nM, final concentration), mixed and incubated for 60 min at room temperature. Non-specific binding may then be determined using (−)-nicotine (30 µM, final concentration). After incubation the samples may then be poured directly onto Whatman GF/C glass fibre filters (presoaked in 0.1% PEI for at least 20 min) under suction and immediately washed with 2×5 mL ice-cold buffer. The amount of radioactivity on the filters may be determined by conventional liquid scintillation counting. Specific binding is total binding minus non-specific binding.

TABLE 2

Binding affinities of (±)-epibatidine (1) and epibatidine analogs 2-11 to six nAChR subtypes.

| Ligand | Introduced Group | $K_i$ (nM) | | | | | |
|---|---|---|---|---|---|---|---|
| | | α2β2 | α2β4 | α3β2 | α3β4 | α4β2 | α4β4 |
| 1 | | 0.025 | 0.095 | 0.035 | 0.565 | 0.061 | 0.157 |
| 2 | 3-exo-OH | 814 | 617 | 1133 | 1171 | 2371 | 515 |
| 3 | 3-endo-OH | 2.5 | 15.3 | 7.3 | 39.1 | 2.9 | 11.2 |
| 6 | 5-exo-OH | 16.9 | 67.5 | 19.3 | 223.9 | 29.3 | 72.8 |
| 7 | 5-endo-OH | 93.7 | 238 | 285 | 916 | 70.9 | 247 |
| 8 | 6-exo-OH | 6.3 | 39.7 | 8.9 | 143.9 | 12.6 | 45.6 |
| 9 | 6-endo-OH | 1.53 | 5.85 | 1.36 | 27.29 | 0.92 | 5.57 |
| 10 | 5-exo-F | 0.86 | 5.59 | 0.65 | 10.36 | 1.73 | 1.22 |
| 11 | 6-exo-F | 0.22 | 0.48 | 0.15 | 2.48 | 0.33 | 0.17 |
| 4 | 5-oxo | 642 | 1140 | 1890 | 4430 | 7080 | 3240 |
| 5 | 6-oxo | 1010 | 3240 | 1500 | 8870 | 2020 | 3560 |

TABLE 3

Binding affinities ($K_i$, nM) of (−)-nicotine, (±)-epibatidine and four constrained epibatidine analogues to six nAChR subtypes[a].

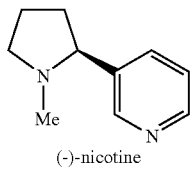
(−)-nicotine

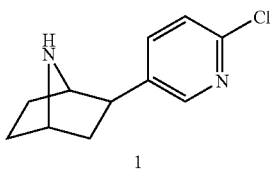
1

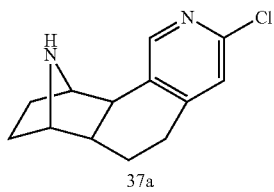
37a

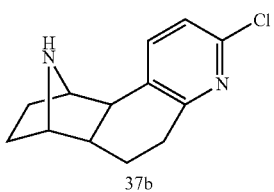
37b

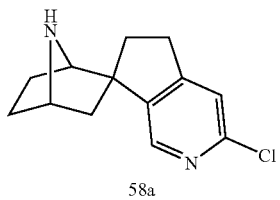
58a

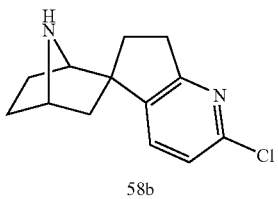
58b

| Ligand | α2β2 | α2β4 | α3β2 | α3β4 | α4β2 | α4β4 |
| --- | --- | --- | --- | --- | --- | --- |
| Nicotine | 12 +/− 2 | 112 +/− 21 | 47 +/− 11 | 443 +/− 60 | 10 +/− 2 | 40 +/− 6 |
| 1 | 0.025 +/− 0.001 | 0.095 +/− 0.017 | 0.035 +/− 0.011 | 0.565 +/− 0.121 | 0.061 +/− 0.009 | 0.157 +/− 0.006 |
| 37a | 290 +/− 5 | 717 +/− 36 | 354 +/− 10 | 2280 +/− 220 | 73 +/− 11 | 637 +/− 302 |
| 37b | 59 +/− 7 | 32 +/− 3 | 530 +/− 81 | 201 +/− 16 | 295 +/− 85 | 41 +/− 14 |
| 58a | 12600 +/− 5300 | 10700 +/− 1000 | 19700 +/− 4500 | 14900 +/− 4500 | 29200 +/− 4300 | 10500 +/− 4500 |
| 58b | 2690 +/− 230 | 7180 +/− 190 | 4070 +/− 850 | 13800 +/− 1700 | 6990 +/− 2000 | 9460 +/− 3700 |

[a]$K_d$ values (nM) for [3H]-epibatidine used for calculating $K_i$ values were 0.02 for a2b2, 0.08 for a2b4, 0.03 for a3b2, 0.30 for a3b4, 0.04 for a4b2 and 0.09 for a4b4 (Xiao and Kellar, 2003, manuscript in preparation). The $K_i$ values of (−)-nicotine and epibatidine (1) shown were the mean ± SEM of 3 to 6 independent measurements. The $K_i$ values of 20a,b and 23a,b shown were the mean ± SEM of 3 independent measurements.

TABLE 4
Binding affinities of (±)-epibatidine (1) and bivalent analogues 59a-d to six nAChR subtypes.
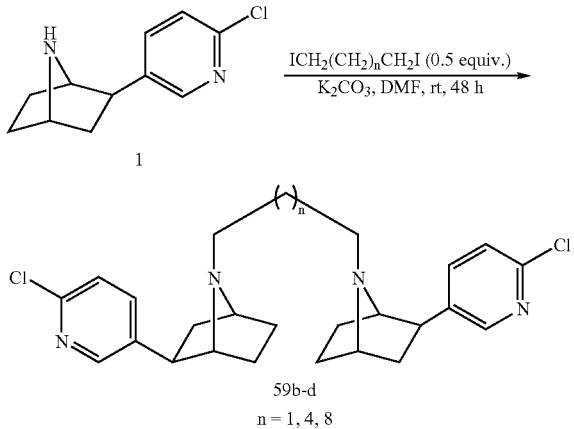
TABLE 4-continued
| Ligand | n = | Ki (nM) | | | | | |
| --- | --- | --- | --- | --- | --- | --- | --- |
| | | α2β2 | α2β4 | α3β2 | α3β4 | α4β2 | α4β4 |
| 1 | N/A | 0.025 | 0.095 | 0.035 | 0.565 | 0.061 | 0.157 |
| 59a | 0 | 1.3 | 2.9 | 5.6 | 11.8 | 10.7 | 18.0 |
| 59b | 1 | 6.1 | 15.7 | 5.2 | 62.9 | 8.7 | 23.3 |
| 59c | 4 | 4.1 | 37.4 | 6.6 | 64.7 | 7.2 | 31.9 |
| 59d | 8 | 5.8 | 24.2 | 6.8 | 67.7 | 10.3 | 18.7 |

TABLE 5
Ki Values (nM) of Ligand Binding to Rat nAChR Subtypes.
| Compounds | ID (PDSP#) | $\alpha2\beta2$ | $\alpha2\beta4$ | $\alpha3\beta2$ | $\alpha3\beta4$ | $\alpha4\beta2$ | $\alpha4\beta2^*$ | $\alpha4\beta4$ |
|---|---|---|---|---|---|---|---|---|
| | Cytisine | 0.5706 | 3.508 | 8.064 | 210.1 | 1.346 | 2.573 | 1.519 |
| | ZW-16 | 1335 | 2625 | >1000 | >10000 | 570.9 | 1496 | 732.3 |
| | ZW-17 | 2980 | 14020 | >1000 | >10000 | 3110 | 4548 | 3227 |
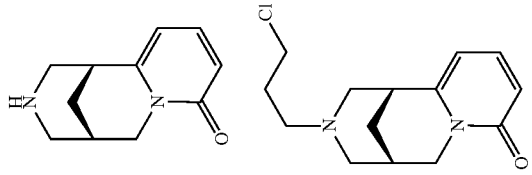
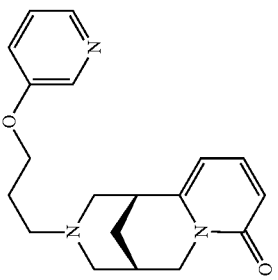

TABLE 5-continued

Ki Values (nM) of Ligand Binding to Rat nAChR Subtypes.

| Compounds | ID (PDSP#) | $\alpha 2\beta 2$ | $\alpha 2\beta 4$ | $\alpha 3\beta 2$ | $\alpha 3\beta 4$ | $\alpha 4\beta 2$ | $\alpha 4\beta 2^*$ | $\alpha 4\beta 4$ |
|---|---|---|---|---|---|---|---|---|
| | ZW-18 | 318.2 | 3476 | >1000 | >10000 | 468.3 | 935.8 | 746.2 |
| | ZW-19 | 239.9 | 1432 | >1000 | >10000 | 383.2 | 603.1 | 467.9 |
| | ZW-36 (02-0528) | 51.0 | 773.0 | 3,590.0 | 26,100.0 | 1,790.0 | 173.0 | 149.0 |

TABLE 5-continued

Ki Values (nM) of Ligand Binding to Rat nAChR Subtypes.

| Compounds | ID (PDSP#) | $K_i$ (nM) | | | | | | |
|---|---|---|---|---|---|---|---|---|
| | | α2β2 | α2β4 | α3β2 | α3β4 | α4β2 | α4β2* | α4β4 |
| (structure) | ZW-37 (02-0529) | 39.10 | 314.00 | 3,010.0 | 11,700.00 | 1,010.0 | 110.00 | 73.40 |
| (structure) | ZW-24 (02-0482) | 814 | 617 | 1,133 | 1,171 | 2,371 | 2,064 | 515 |
| (structure) | ZW-25 (02-0483) | 2.49 | 15.3 | 7.31 | 39.1 | 2.92 | 4.79 | 11.2 |
| (structure) | ZW-26 (02-0484) | 93.7 | 238 | 285 | 916 | 70.9 | 134 | 247 |
| (structure) | ZW-27 (02-0485) | 1.532 | 5.850 | 1.359 | 27.290 | 0.916 | 4.108 | 5.574 |

TABLE 5-continued

Ki Values (nM) of Ligand Binding to Rat nAChR Subtypes.

| Compounds | ID (PDSP#) | K$_i$ (nM) | | | | | | |
|---|---|---|---|---|---|---|---|---|
| | | α2β2 | α2β4 | α3β2 | α3β4 | α4β2 | α4β2* | α4β4 |
| [structure] | ZW-28 (02-0486) | 16.950 | 67.510 | 19.280 | 223.900 | 29.330 | 69.020 | 72.75 |
| [structure] | ZW-29 (02-0487) | 6.298 | 39.730 | 8.884 | 143.900 | 12.580 | 22.930 | 45.57 |
| [structure] | ZW-30 (02-0488) | 0.864 | 5.590 | 0.646 | 10.360 | 1.734 | 2.109 | 1.225 |
| [structure] | ZW-31 (02-0489) | 0.218 | 0.481 | 0.149 | 2.476 | 0.328 | 0.668 | 0.172 |
| [structure] | ZW-32 (02-0501) | 2,464 | 7,088 | 3,664 | 14,890 | 5,048 | 12,122 | 9,564 |
| [structure] | ZW-33 (02-0502) | 59.41 | 32.24 | 540.5 | 200.7 | 210.35 | 575.85 | 39.78 |

TABLE 5-continued

Ki Values (nM) of Ligand Binding to Rat nAChR Subtypes.

| Compounds | ID (PDSP#) | $K_i$(nM) | | | | | | |
|---|---|---|---|---|---|---|---|---|
| | | α2β2 | α2β4 | α3β2 | α3β4 | α4β2 | α4β2* | α4β4 |
| (structure) | ZW-34 (02-0503) | 12,784 | 11,610 | 15,985 | 36,700 | 28,020 | 54,350 | 10,200 |
| (structure) | ZW-35 (02-0504) | 293.6 | 693.5 | 345.35 | 2,167 | 67.42 | 339.5 | 672.5 |
| (structure) | ZW-38 (02-0530) | 4.120 | 37.400 | 6.610 | 64.700 | 7.2 | 14.200 | 31.900 |
| (structure) | ZW-39 (02-0531) | 16.900 | 67.400 | 19.8 | 95.400 | 67.700 | 52.000 | 61.800 |
| (structure) | ZW-56 (02-0581) | 6.08 | 15.70 | 5.17 | 62.90 | 8.66 | 10.10 | 23.30 |

TABLE 5-continued
Ki Values (nM) of Ligand Binding to Rat nAChR Subtypes.
| Compounds | ID (PDSP#) | $\alpha 2\beta 2$ | $\alpha 2\beta 4$ | $\alpha 3\beta 2$ | $\alpha 3\beta 4$ | $\alpha 4\beta 2$ | $\alpha 4\beta 2$* | $\alpha 4\beta 4$ |
|---|---|---|---|---|---|---|---|---|
|  | ZW-57 (02-0582) | 5.78 | 24.20 | 6.75 | 67.70 | 10.30 | 13.90 | 18.70 |
| 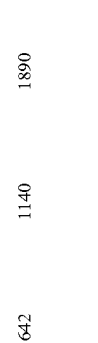 | ZW-80 (03-0897) | 642 | 1140 | 1890 | 4430 | 7080 | 4570 | 3240 |
|  | ZW-81 (03-0898) | 1010 | 3240 | 1500 | 8870 | 2020 | 1350 | 3560 |
|  | ZW-82 (03-0899) | 30 | 93.8 | 147 | 173 | 57.3 | 304 | 53.1 |
|  | ZW-83 (03-0900) (mix) | 1.28 | 2.86 | 5.56 | 11.8 | 10.7 | 29.1 | 18 |
|  | ZW-84 (03-0901) | 7.08 | 16.6 | 21.1 | 67.6 | 21.9 | 112 | 84.5 |

TABLE 5-continued

Ki Values (nM) of Ligand Binding to Rat nAChR Subtypes.

| Compounds | ID (PDSP#) | α2β2 | α2β4 | α3β2 | K$_i$(nM) α3β4 | α4β2 | α4β2* | α4β4 |
|---|---|---|---|---|---|---|---|---|
| A-84543 | ZW-85 (03-1066) | 1.07 | 209.0 | 9.04 | 835.0 | 1.40 | 5.15 | 205.0 |
| | ZW-86 (03-1067) | 1.32 | 546.0 | 29.3 | 2040.0 | 1.56 | 7.24 | 345.0 |
| | ZW-87 (03-1068) | 0.75 | 434.0 | 10.70 | 3080.0 | 1.02 | 3.65 | 473.0 |
| | ZW-88 (03-1069) | 1.93 | 5890.0 | 19.70 | 32600.0 | 1.34 | 8.39 | 5060.0 |
| | ZW-89 (03-1070) | 2.43 | 1880.0 | 7.64 | 18200.0 | 0.954 | 3.16 | 1690.0 |

TABLE 5-continued

Ki Values (nM) of Ligand Binding to Rat nAChR Subtypes.

| Compounds | ID (PDSP#) | α2β2 | α2β4 | α3β2 | α3β4 | α4β2 | α4β2* | α4β4 |
|---|---|---|---|---|---|---|---|---|
| | ZW-90 (03-1071) | 2.87 | 3230.0 | 12.6 | 40200.0 | 0.81 | 3.56 | 1270.0 |
| | ZW-91 (03-1072) | 3.33 | 1150.0 | 13.40 | 20000.0 | 0.75 | 5.39 | 968.0 |
| | ZW-92 (03-1073) | 406.0 | 31600.0 | 870.0 | 89600.0 | 201.0 | 505.0 | 31900.0 |
| | ZW-93 (03-1074) | 26.8 | 7800.0 | 52.1 | 62700.0 | 6.50 | 21.70 | 3560.0 |
| | ZW-94 (03-1230) | 0.352 | 45.10 | 0.146 | 266.0 | 0.166 | 0.215 | 15.40 |

TABLE 5-continued

Ki Values (nM) of Ligand Binding to Rat nAChR Subtypes.

| Compounds | ID (PDSP#) | $K_i$ (nM) | | | | | | |
|---|---|---|---|---|---|---|---|---|
| | | α2β2 | α2β4 | α3β2 | α3β4 | α4β2 | α4β2* | α4β4 |
| (5-pentyl-pyridin-3-yl-azabicycle) | ZW-95 (03-1231) | 0.323 | 24.90 | 0.165 | 122.0 | 0.151 | 0.314 | 7.91 |
| (chloro-pyridine-carboxylate-azabicycle) | ZW-96 (03-1270) | 5,410 | 28,100 | 5,510 | 10,700 | 7,870 | 18,400 | 46,500 |
| (pyridyl-butynyl-methylpyrrolidine ether) | ZW-97 (03-1271) | 1.19 | 8,240 | 7.27 | 59,900 | 2.07 | 3.71 | 8,280 |
| (pyridyl-fluoroethynyl-methylpyrrolidine ether) | ZW-98 (03-1272) | 4.52 | 437 | 4.96 | 2,460 | 0.936 | 6.40 | 369 |
| (pyridyl-aminobutynyl-methylpyrrolidine ether) | ZW-99 (03-1274) | 7.52 | 7,400 | 47.4 | 127,000 | 7.18 | 41.4 | 6,130 |

TABLE 5-continued
Ki Values (nM) of Ligand Binding to Rat nAChR Subtypes.
| Compounds | ID (PDSP#) | $\alpha 2\beta 2$ | $\alpha 2\beta 4$ | $\alpha 3\beta 2$ | $\alpha 3\beta 4$ | $\alpha 4\beta 2$ | $\alpha 4\beta 2^*$ | $\alpha 4\beta 4$ |
|---|---|---|---|---|---|---|---|---|
| 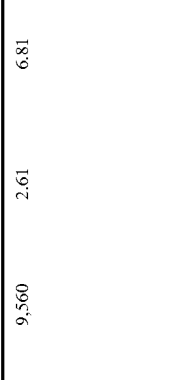 | ZW-100 (03-1275) | 13.4 | 1,720 | 20.3 | 9,560 | 2.61 | 6.81 | 1,410 |
|  | ZW-101 (03-1276) | 1.51 | 835 | 2.69 | 16,100 | 0.665 | 1.15 | 778 |
| 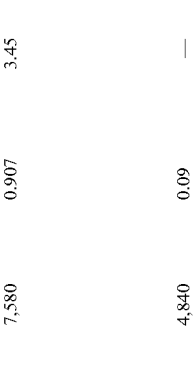 | ZW-102 (03-1277) | 3.50 | 680 | 5.27 | 7,580 | 0.907 | 3.45 | 721 |
|  | ZW-103 (03-1278) | 0.06 | 269 | 0.53 | 4,840 | 0.09 | — | 74 |
|  | ZW-104 (03-1279) | 0.796 | 197 | 0.635 | 5,490 | 0.201 | 0.362 | 118 |

TABLE 5-continued
Ki Values (nM) of Ligand Binding to Rat nAChR Subtypes.
| Compounds | ID (PDSP#) | $K_i$ (nM) | | | | | | |
|---|---|---|---|---|---|---|---|---|
| | | α2β2 | α2β4 | α3β2 | α3β4 | α4β2 | α4β2* | α4β4 |
| 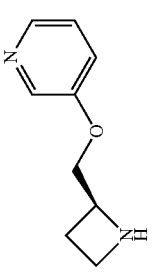 | A-85380 | 0.073 | 18.4 | 0.208 | 77.7 | 0.142 | 0.248 | 8.04 |
| 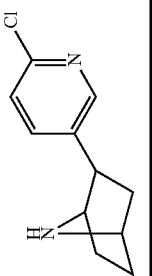 | Nicotine | 12 | 112 | 47 | 443 | 10 | — | 40 |
| 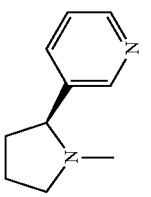 | Epibatidine | 0.025 | 0.095 | 0.035 | 0.565 | 0.061 | 0.060 | 0.157 |
*Rat forebrain, mainly α4β2.

TABLE 6

Summary Table of Competition Binding with [3H]-Epibatidine.*
Concentration of [3H]-EB: 0.099 nM, 0.091 nM # of Concentration of Tested Ligand:

| Samples (PDSP#) | Concentration Range | Ki (nM)* | | | | | | |
|---|---|---|---|---|---|---|---|---|
| | | α2β2 | α2β4 | α3β2 | α3β4 | α4β2 | α4β2** | α4β4 |
| ZW-85 | 0.00197-100 μM | 1.070 | 209.000 | 9.040 | 835.000 | 1.400 | 5.150 | 205.000 |
| ZW-86 | 0.00197-100 μM | 1.320 | 546.000 | 29.300 | 2040.000 | 1.560 | 7.240 | 345.000 |
| ZW-87 | 0.00197-100 μM | 0.749 | 434.000 | 10.700 | 3080.000 | 1.020 | 3.650 | 473.000 |
| ZW-88 | 0.00197-100 μM | 1.930 | 5890.000 | 19.700 | 32600.000 | 1.340 | 8.390 | 5060.000 |
| ZW-89 | 0.00197-100 μM | 2.430 | 1880.000 | 7.640 | 18200.000 | 0.954 | 3.160 | 1690.000 |
| ZW-90 | 0.00197-100 μM | 2.870 | 3230.000 | 12.600 | 40200.000 | 0.810 | 3.560 | 1270.000 |
| ZW-91 | 0.00197-100 μM | 3.330 | 1150.000 | 13.400 | 20000.000 | 0.754 | 5.390 | 968.000 |
| | 0.00197-100 μM | 406.00 | 31600.00 | 870.00 | | | 505.00 | |
| ZW-92 | | 0 | 0 | 0 | 89600.000 | 201.000 | 0 | 31900.00 |
| ZW-93 | 0.00197-100 μM | 26.800 | 7800.000 | 52.100 | 62700.000 | 6.500 | 21.700 | 3560.000 |
| Epibatidine*** | | 0.0 25 | 0.095 | 0.035 | 0.565 | 0.061 | 0.060 | 0.157 |
| A-85380*** | | 0.0 73 | 18.400 | 0.208 | 77.700 | 0.142 | 0.248 | 8.040 |

*n = 1.
**Forebrain mainly α4β2.

Dosages

The dosage of any compositions of the present invention will vary depending on the symptoms, age and body weight of the patient, the nature and severity of the disorder to be treated or prevented, the route of administration, and the form of the subject composition. Any of the subject formulations may be administered in a single dose or in divided doses. Dosages for the compositions of the present invention may be readily determined by techniques known to those of skill in the art or as taught herein.

In certain embodiments, the dosage of the subject compounds will generally be in the range of about 0.01 ng to about 10 g per kg body weight, specifically in the range of about 1 ng to about 0.1 g per kg, and more specifically in the range of about 100 ng to about 10 mg per kg.

An effective dose or amount, and any possible affects on the timing of administration of the formulation, may need to be identified for any particular composition of the present invention. This may be accomplished by routine experiment as described herein, using one or more groups of animals (preferably at least 5 animals per group), or in human trials if appropriate. The effectiveness of any subject composition and method of treatment or prevention may be assessed by administering the composition and assessing the effect of the administration by measuring one or more applicable indices, and comparing the post-treatment values of these indices to the values of the same indices prior to treatment.

The precise time of administration and amount of any particular subject composition that will yield the most effective treatment in a given patient will depend upon the activity, pharmacokinetics, and bioavailability of a subject composition, physiological condition of the patient (including age, sex, disease type and stage, general physical condition, responsiveness to a given dosage and type of medication), route of administration, and the like. The guidelines presented herein may be used to optimize the treatment, e.g., determining the optimum time and/or amount of administration, which will require no more than routine experimentation consisting of monitoring the subject and adjusting the dosage and/or timing.

While the subject is being treated, the health of the patient may be monitored by measuring one or more of the relevant indices at predetermined times during the treatment period. Treatment, including composition, amounts, times of administration and formulation, may be optimized according to the results of such monitoring. The patient may be periodically reevaluated to determine the extent of improvement by measuring the same parameters. Adjustments to the amount(s) of subject composition ministered and possibly to the time of administration may be made based on these reevaluations.

Treatment may be initiated with smaller dosages which are less than the optimum dose of the compound. Thereafter, the dosage may be increased by small increments until the optimum therapeutic effect is attained.

The use of the subject compositions may reduce the required dosage for any individual agent contained in the compositions because the onset and duration of effect of the different agents may be complimentary.

Toxicity and therapeutic efficacy of subject compositions may be determined by standard pharmaceutical procedures in cell cultures or experimental animals, e.g., for determining the $LD_{50}$ and the $ED_{50}$.

The data obtained from the cell culture assays and animal studies may be used in formulating a range of dosage for use in humans. The dosage of any subject composition lies preferably within a range of circulating concentrations that include the $ED_{50}$ with little or no toxicity. The dosage may vary within this range depending upon the dosage form employed and the route of administration utilized. For compositions of the present invention, the therapeutically effective dose may be estimated initially from cell culture assays.

Formulation

The compositions of the present invention may be administered by various means, depending on their intended use, as is well known in the art. For example, if compositions of the present invention are to be administered orally, they may be formulated as tablets, capsules, granules, powders or syrups. Alternatively, formulations of the present invention may be administered parenterally as injections (intravenous, intramuscular or subcutaneous), drop infusion preparations or suppositories. For application by the ophthalmic mucous membrane route, compositions of the present invention may be formulated as eyedrops or eye ointments. These formulations may be prepared by conventional means, and, if desired, the compositions may be mixed with any conventional additive, such as an excipient, a binder, a disintegrating agent, a lubricant, a corrigent, a solubilizing agent, a suspension aid, an emulsifying agent or a coating agent.

In formulations of the subject invention, wetting agents, emulsifiers and lubricants, such as sodium lauryl sulfate and magnesium stearate, as well as coloring agents, release agents, coating agents, sweetening, flavoring and perfuming agents, preservatives and antioxidants may be present in the formulated agents.

Subject compositions may be suitable for oral, nasal, topical (including buccal and sublingual), rectal, vaginal, aerosol and/or parenteral administration. The formulations may conveniently be presented in unit dosage form and may be prepared by any methods well known in the art of pharmacy. The amount of composition that may be combined with a carrier material to produce a single dose vary depending upon the subject being treated, and the particular mode of administration.

Methods of preparing these formulations include the step of bringing into association compositions of the present invention with the carrier and, optionally, one or more accessory ingredients. In general, the formulations are prepared by uniformly and intimately bringing into association agents with liquid carriers, or finely divided solid carriers, or both, and then, if necessary, shaping the product.

Formulations suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia), each containing a predetermined amount of a subject composition thereof as an active ingredient. Compositions of the present invention may also be administered as a bolus, electuary, or paste.

In solid dosage forms for oral administration (capsules, tablets, pills, dragees, powders, granules and the like), the subject composition is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the subject composition moistened with an inert liquid diluent. Tablets, and other solid dosage forms, such as dragees, capsules, pills and granules, may optionally be scored or prepared with coatings and shells, such as enteric coatings and other coatings well known in the pharmaceutical-formulating art.

Liquid dosage forms for oral administration include pharmaceutically acceptable emulsions, microemulsions, solutions, suspensions, syrups and elixirs. In addition to the subject composition, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Suspensions, in addition to the subject composition, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations for rectal or vaginal administration may be presented as a suppository, which may be prepared by mixing a subject composition with one or more suitable non-irritating excipients or carriers comprising, for example, cocoa butter, polyethylene glycol, a suppository wax or a salicylate, and which is solid at room temperature, but liquid at body temperature and, therefore, will melt in the body cavity and release the active agent. Formulations which are suitable for vaginal administration also include pessaries, tampons, creams, gels, pastes, foams or spray formulations containing such carriers as are known in the art to be appropriate.

Dosage forms for transdermal administration of a subject composition includes powders, sprays, ointments, pastes, creams, lotions, gels, solutions, patches and inhalants. The active component may be mixed under sterile conditions with a pharmaceutically acceptable carrier, and with any preservatives, buffers, or propellants which may be required.

The ointments, pastes, creams and gels may contain, in addition to a subject composition, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays may contain, in addition to a subject composition, excipients such as lactose, talc, silicic acid, aluminum hydroxide, calcium silicates and polyamide powder, or mixtures of these substances. Sprays may additionally contain customary propellants, such as chlorofluorohydrocarbons and volatile unsubstituted hydrocarbons, such as butane and propane.

Compositions of the present invention may alternatively be administered by aerosol. This is accomplished by preparing an aqueous aerosol, liposomal preparation or solid particles containing the compound. A non-aqueous (e.g., fluorocarbon propellant) suspension could be used. Sonic nebulizers may be used because they minimize exposing the agent to shear, which may result in degradation of the compounds contained in the subject compositions.

Ordinarily, an aqueous aerosol is made by formulating an aqueous solution or suspension of a subject composition together with conventional pharmaceutically acceptable carriers and stabilizers. The carriers and stabilizers vary with the requirements of the particular subject composition, but typically include non-ionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

Pharmaceutical compositions of this invention suitable for parenteral administration comprise a subject composition in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and non-aqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity may be maintained, for example, by the use of coating materials, such as lecithin, by the maintenance of the required particle size in the case of dispersions, and by the use of surfactants.

Kits

This invention also provides kits for conveniently and effectively implementing the methods of this invention. Such kits comprise any subject composition, and a means for facilitating compliance with methods of this invention. Such kits provide a convenient and effective means for assuring that the subject to be treated takes the appropriate active in the correct dosage in the correct manner. The compliance means of such kits includes any means which facilitates administering the actives according to a method of this invention. Such compliance means include instructions, packaging, and dispensing means, and combinations thereof. Kit components may be packaged for either manual or partially or wholly automated practice of the foregoing methods. In other embodiments involving kits, this invention contemplates a kit including compositions of the present invention, and optionally instructions for their use.

EXEMPLIFICATION

The invention now being generally described, it will be more readily understood by reference to the following examples which are included merely for purposes of illustration of certain aspects and embodiments of the present invention, and are not intended to limit the invention.

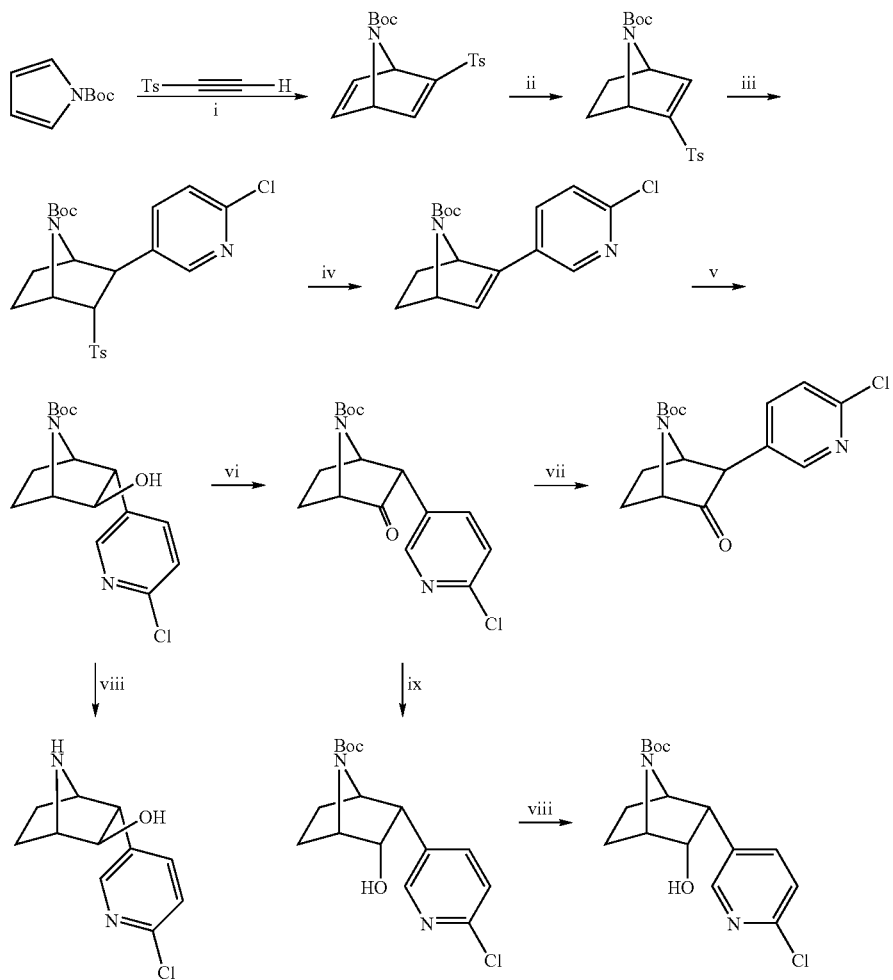

Reagents and conditions: (i) Toluene, 80° C.; (ii) Pd—C (cat.), H$_2$; (iii) 2-chloro-5-iodopyridine, n-BuLi, THF, -78° C., 86%; (iv) t-BuOK, THF, -78° C. to rt, 98%; (v) BH$_3$•THF, THF, rt, overnight, then aq. NaOH, 35% H$_2$O$_2$, 63%; (vi) Dess-Martin periodinane, CH$_2$Cl$_2$, 96%; (vii) silica gel, rt; (viii) CF$_3$COOH, CH$_2$Cl$_2$; (ix) L-Selectride, THF, -30 to 0° C., 91%.

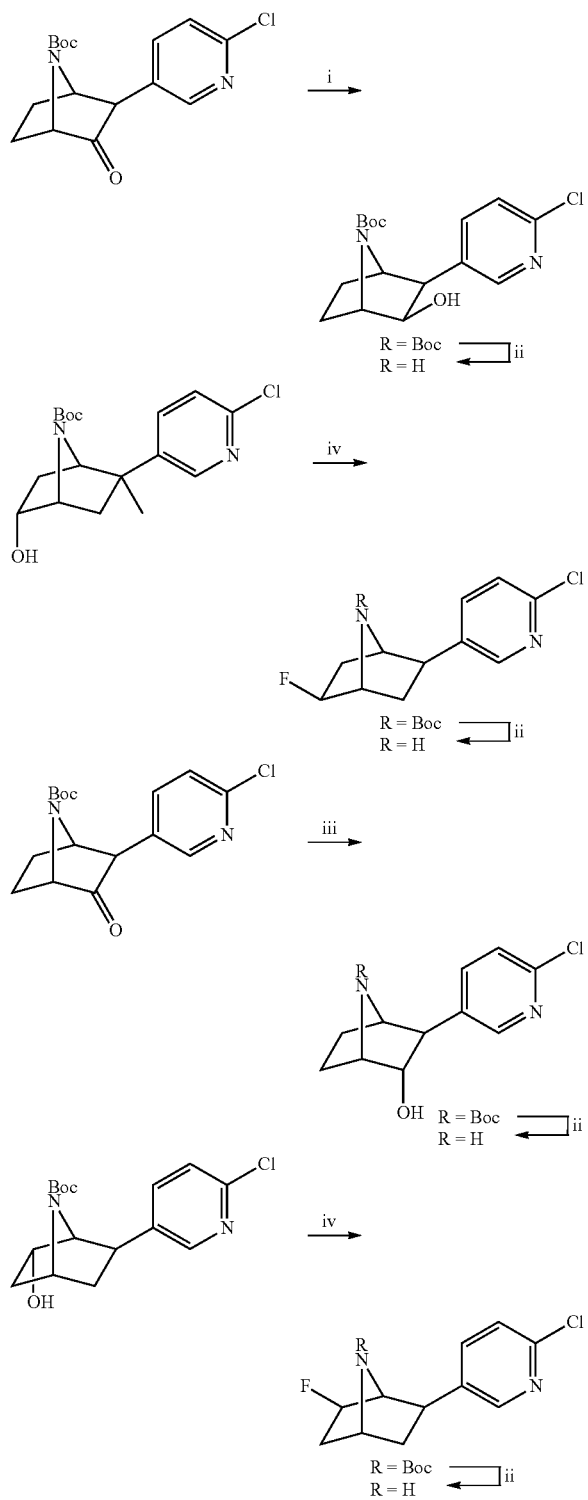

Reagents and conditions (i) L-Selectride, THF, -78° C. to rt, 92%; (ii) CF$_3$COOH, CH$_2$Cl$_2$; (iii) NaBH$_4$, THF, 95% (diastereo-selectivity 3:1); (iv) DAST, CH$_2$Cl$_2$, -78° C. to rt, 83-87%.

7-tert-Butoxycarbonyl-2-p-tolylsulfonyl)-7-azabicyclo [2.2.1]hept-2,5-diene: A stirred mixture of p-tolylsulfonylacetylene (6 g, 33 mmol) and N-tert-butoxycarbonylpyrrole (14 g, 83 mmol) was heated under N$_2$ at 80° C. for 36 h. Then the excess N-tert-butoxycarbonylpyrrole was removed in vacuo and the slurry residue was chromatographied with n-hexane-EtOAc (10:1 to 4:1) to give the product as a yellow solid (9.5 g, 83%). $^1$H NMR (CDCl$_3$) δ 7.75 (AB, 2H, J=8.1 Hz), 7.57 (s, 1H), 7.35 (AB, 2H, J=8.1 Hz), 6.94 (m, 1H), 6.87 (dd, 1H, J=5.4, 2.7 Hz), 5.38 (s, 1H), 5.17 (s, 1H), 2.44 (s, 3H), 1.26 (s, 9H); $^{13}$C NMR (CDCl$_3$) δ 154.02, 152.80, 151.60, 145.10, 144.03, 143.18, 141.67, 130.20, 128.27, 81.56, 67.83, 67.02, 27.98, 21.81.

7-tert-Butoxycarbonyl-2-(p-tolylsulfonyl)-7-azabicyclo [2.2.1]hept-2-ene: A mixture of 7-tert-butoxycarbonyl-2-p-tolylsulfonyl)-7-azabicyclo[2.2.1]hept-2-ene (4.2 g, 12.1 mmol), CH$_3$CN (160 mL), 5% Pd—C (0.4 g) was vigorously stirred under 1 atm of H$_2$ at room temperature. After the required volume of H$_2$ was absorbed, the reaction mixture was filtered through Celite. The filtrate was concentrated in vacuo to give a white solid (4.2 g, 100%). $^1$H NMR (CDCl$_3$) δ 7.81 and 7.36 (AB, 4H, J=8.1 Hz), 7.06 (d, 1H, J=2.4 Hz), 4.83 (s, 1H), 4.77 (d, 1H, J=3.6 Hz), 2.45 (s, 3H), 2.10-1.95 (m, 2H), 1.45-1.26 (m, 2H), 1.21 (s, 9H).

7-tert-Butoxycarbonyl-2-exo-(2-chloro-5-pyridyl)-3-endo-(p-tolylsulfonyl)-7-azabicyclo[2.2.1]heptane: To a stirred solution of 5-iodo-2-chloropyridine (4.5 g, 19 mmol) in THF (135 mL) under N$_2$ at -78° C. was added dropwise n-BuLi (2.5 M in hexanes, 9.0 mL, 22 mmol). After 30 min a solution of 7-tert-butoxycarbonyl-2-(p-tolylsulfonyl)-7-azabicyclo[2.2.1]hept-2-ene (5.7 g, 16 mmol) in THF (60 mL) was added dropwise to the metallated pyridine. After 1 h at -78° C., sat. aq. NaHCO$_3$ (20 mL) was added and the solution was warmed to room temperature. The mixture was concentrated in vacuo, diluted with brine (100 mL), and extracted with EtOAc (3×100 mL). The combined organic layers were washed with brine, dried over MgSO$_4$, filtered and concentrated. The residue was purified by chromatography with CHCl$_3$-hexane-diethyl ether (8:6:1) to give a white foam (6.5 g, 86%). $^1$H NMR (CDCl$_3$) δ 8.18 (s, 1H), 7.66 and 7.28 (AB, 4H, J=8.1 Hz), 7.54 (dd, 1H, J=8.1, 1.8 Hz), 7.17 (d, 1H, J=8.1 Hz), 4.44 (s, 1H), 4.28 (d, 1H, J=4.5 Hz), 3.58 (t, 1H, J=4.5 Hz), 3.32 (s, 1H), 2.67 (m, 1H), 2.41 (s, 3H), 2.05-1.70 (m, 3H), 1.42 (s, 9H).

7-tert-Butoxycarbonyl-2-(2-chloro-5-pyridyl)-7-azabicyclo[2.2.1]hept-2-ene: To a stirred solution of 7-tert-butoxycarbonyl-2-exo-(2-chloro-5-pyridyl)-3-endo-p-tolylsulfonyl)-7-azabicyclo[2.2.1]heptane (400 mg, 0.86 mmol) in THF (40 mL) was added t-BuOK (350 mg, 3.12 mmol) in one portion under N$_2$ at -78° C. The reaction mixture was warmed slowly to room temperature and stirred at room temperature for 1 h. Then sat. aq. NH$_4$Cl (5 mL) was added and the mixture was concentrated. The residue was dissolved in EtOAc (50 mL) and washed with brine, dried over Na$_2$SO$_4$, concentrated, and purified by chromatography with hexane-EtOAc (5:1) to give a syrup (260 mg, 98%). $^1$H NMR (CDCl$_3$) δ 8.42 (d, 1H, J=2.4 Hz), 7.64 (dd, 1H, J=8.4, 2.4 Hz), 7.30 (d, 1H, J=8.4 Hz), 6.56 (s, 1H), 5.04 (s, 1H), 4.82 (s, 1H), 2.11-1.96 (m, 2H), 1.42 (s, 9H), 1.36-1.16 (m, 2H). $^{13}$C NMR (CDCl$_3$) δ 155.08, 150.15, 146.22, 143.57, 135.28, 130.86, 127.97, 124.31, 80.27, 61.15, 60.40, 28.19, 25.70, 24.21.

7-tert-Butoxycarbonyl-2-endo-(2-chloro-5-pyridyl)-3-exo-hydroxyl-7-azabicyclo[2.2.1]heptane: To a solution of 7-tert-butoxycarbonyl-2-(2-chloro-5-pyridyl)-7-azabicyclo [2.2.1]hept-2-ene (1.80 g, 5.9 mmol) in anhydrous THF (50 mL) was added dropwise borane-THF complex (1.0 M in THF, 18 mL, 18 mmol) under N$_2$ at -78° C. The reaction mixture was slowly warmed to room temperature and stirred at room temperature overnight. Then the reaction mixture was quenched by sequential addition of water (15 mL), sodium hydroxide solution (6.0 M, 15 mL), ethanol (10 mL), and 35% of hydrogen peroxide solution (15 mL). The mixture was stirred for a further 30 min, and then diluted with EtOAc (200 mL). The organic layer was separated and washed with brine, dried over $Na_2SO_4$, and concentrated. The residue was purified by chromatography with hexane-EtOAc (2:1) to give a syrup (1.20 g, 63%). $^1$H NMR (CDCl$_3$) δ 8.24 (d, 1H, J=2.4 Hz), 7.48 (dd, 1H, J=8.1, 2.4 Hz), 7.30 (d, 1H, J=8.1 Hz), 4.40 (t, 1H, J=4.2 Hz), 4.24 (d, 1H, J=4.5 Hz), 4.05 (s, 1H), 3.20 (s, 1H), 2.5 (br s, 1H), 1.85 (m, 1H), 1.56 (m, 1H), 1.48 (s, 9H), 1.36-1.25 (m, 2H). $^{13}$C NMR (CDCl$_3$) δ 156.43, 150.03, 149.31, 138.60, 133.13, 124.27, 80.71, 79.15, 64.40, 59.90, 56.39, 28.45, 25.07, 22.39.

7-tert-Butoxycarbonyl-2-endo-(2-chloro-5-pyridyl)-7-azabicyclo[2.2.1]heptan-3-one: To a solution of 7-tert-butoxycarbonyl-2-endo-(2-chloro-5-pyridyl)-3-exo-hydroxyl-7-azabicyclo[2.2.1]heptane (730 mg, 2.2 mmol) in $CH_2Cl_2$ (50 mL) was added Dess-Martin periodinane (1.2 g, 2.8 mmol) and the reaction mixture was stirred at room temperature for 4 h. After removal of most of the solvent in vacuo, the residue was passed through a short silica gel column. The crude product was further purified by chromatography with hexane-EtOAc (4:1) to give a syrup (700 mg, 96%). $^1$H NMR (CDCl$_3$) δ 8.25 (d, 1H, J=2.4 Hz), 7.55 (dd, 1H, J=8.4, 2.4 Hz), 7.34 (d, 1H, J=8.4 Hz), 4.75 (t) 1H, J=4.8 Hz), 4.44 (d, 1H, J=5.4 Hz), 3.85 (d, 1H, J=5.1 Hz), 2.23-2.10 (m, 1H), 1.88-1.75 (m, 1H), 1.71-1.60 (m, 1H), 1.56-1.43 (m, 1H), 1.50 (s, 9H). $^{13}$C NMR (CDCl$_3$) δ 208.23, 154.87, 150.86, 149.95, 138.79, 129.06, 124.55, 81.73, 64.97, 60.58, 55.88, 28.36, 25.32, 22.76.

7-tert-Butoxycarbonyl-2-exo-(2-chloro-5-pyridyl)-7-azabicyclo[2.2.1]heptan-3-one: A solution of 7-tert-butoxycarbonyl-2-endo-(2-chloro-5-pyridyl)-7-azabicyclo[2.2.1]heptan-3-one (200 mg, 0.62 mmol) in $CH_2Cl_2$ was loaded on a precoated silica gel plate (size: 20×20 cm; layer thickness: 250 μm. Silica Gel 60 $F_{254}$, Merck Co.). After 2 days at room temperature, the silica gel was removed and washed with EtOAc, and the solution was concentrated. The residue was purified by chromatography with hexane-EtOAc (5:1) to give the recovered starting material (74 mg, 37%), followed by a white solid (126 mg, 63%). $^1$H NMR (CDCl$_3$) δ 8.36 (d, 1H, J=2.4 Hz), 7.64 (dd, 1H, J=8.4, 2.4 Hz), 7.28 (d, 1H, J=8.4 Hz), 4.72 (s, 1H), 4.43 (d, 1H, J=3.6 Hz), 3.18 (s, 1H), 2.20-2.0 (m, 2H), 1.90-1.75 (m, 2H), 1.45 (s, 9H). $^{13}$C NMR (CDCl$_3$) δ 206.07, 154.73, 150.59, 149.16, 137.84, 130.57, 124.40, 81.60, 63.41, 60.58, 56.87, 28.35, 28.17, 24.70. Anal. Calcd for (C$_{16}$H$_{19}$ClN$_2$O$_3$. 1/5H$_2$O) C, 58.88; H, 5.99; N, 8.58. Found: C, 59.08; H, 5.81; N, 8.54.

7-tert-Butoxycarbonyl-2-endo-(2-chloro-5-pyridyl)-3-endo-hydroxyl-7-azabicyclo[2.2.1]heptane: To a stirred solution of 7-tert-butoxycarbonyl-2-endo-(2-chloro-5-pyridyl)-7-azabicyclo[2.2.1]heptan-3-one (120 mg, 0.37 mmol) in anhydrous THF (10 mL) was added L-Selectride (1.0 M in THF, 520 μL, 0.52 mmol) under N$_2$ at −30° C. The reaction mixture was slowly warmed to 0° C. in 1 h. Ethanol (2 mL) was added, followed by saturated aq. NH$_4$Cl (2 mL) and then diluted with EtOAc (50 mL). The organic layer was separated and washed with brine, dried over Na$_2$SO$_4$, and concentrated. The residue was purified by chromatography with hexane-EtOAc (30:1) to give a syrup (110 mg, 91%). $^1$H NMR (CDCl$_3$) δ 8.22 (d, 1H, J=2.4 Hz), 7.68 (dd, 1H, J=8.4, 2.4 Hz), 7.24 (d, 1H, J=8.4 Hz), 4.58 (m, 1H), 4.33 (t, 1H, J=4.5 Hz), 4.21 (s, 1H), 3.34 (dd, 1H, J=9.6, 4.5 Hz), 3.28 (d, 1H, J=3.9 Hz), 2.23 (m, 1H), 1.76-1.53 (m, 3H), 1.47 (s, 9H). Anal. Calcd for (C$_{16}$H$_{21}$ClN$_2$O$_3$. 1/4H$_2$O) C, 58.36; H, 6.58; N, 8.51. Found: C, 58.48; H, 6.68; N, 8.33.

7-tert-Butoxycarbonyl-2-exo-(2-chloro-5-pyridyl)-3-exo-hydroxyl-7-azabicyclo[2.2.1]heptane: To a stirred solution of 7-tert-butoxycarbonyl-2-exo-(2-chloro-5-pyridyl)-7-azabicyclo[2.2.1]heptan-3-one (40 mg, 0.12 mmol) in anhydrous THF (4 mL) at −78° C. under N$_2$ was added L-Selectride (1.0 M in THF, 160 mL, 0.16 mmol). The reaction mixture was slowly warmed to room temperature in 1 h. After this time, the solution was cooled to 0° C. and ethanol (0.5 mL) was added, followed by saturated aq. NH$_4$Cl (0.5 mL) and then diluted with EtOAc (30 mL). The organic layer was separated and washed with brine, dried over Na$_2$SO$_4$, and concentrated. The residue was purified by chromatography with hexane-EtOAc (2:1) to give a syrup (37 mg, 92%). $^1$H NMR (CDCl$_3$) δ 8.21 (d, 1H, J=2.1 Hz), 7.70 (d, 1H, J=6.9 Hz), 7.28 (d, 1H, J=8.4 Hz), 4.30 (d, 1H, J=3.0 Hz), 4.19 (d, 1H, J=5.1 Hz), 4.08 (t, 1H, J=7.5 Hz), 3.04 (d, 1H, J=7.5 Hz), 1.95-1.70 (m, 3H), 1.58-1.50 (m, 2H), 1.48 (s, 9H). $^{13}$C NMR (CDCl$_3$) δ 156.09, 150.01, 149.95, 139.49, 133.14, 124.07, 80.69, 76.12, 63.16, 61.15, 51.92, 29.22, 28.49, 24.31. Anal. Calcd for (C$_{16}$H$_{21}$ClN$_2$O$_3$. 1/5H$_2$O) C, 58.52; H, 6.57; N, 8.53. Found: C, 58.29; H, 6.27; N, 8.25.

7-tert-Butoxycarbonyl-2-exo-(2-chloro-5-pyridyl)-3-endo-hydroxyl-7-azabicyclo[2.2.1]heptane: To a stirred solution of 7-tert-butoxycarbonyl-2-exo-(2-chloro-5-pyridyl)-7-azabicyclo[2.2.1]heptan-3-one (40 mg, 0.12 mmol) in THF (5 mL) was added NaBH$_4$ (20 mg, 0.5 mmol) and water (200 Fu) and the reaction mixture was stirred at room temperature for 1 h. After that water (5 mL) was added and neutralized to pH 7.0 with 1 M aq. HCl. (0.5 mL). The mixture was extracted with EtOAc (3×10 mL). The combined organic layer was washed with brine, dried over Na$_2$SO$_4$, and concentrated. The residue was purified by chromatography with hexane-EtOAc (2:1) to give a syrup (29 m g, 72%). $^1$H NMR (CDCl$_3$) δ 8.21 (d, 1H, J=2.4 Hz), 7.66 (dd, 1H, J=8.4, 2.4 Hz), 7.25 (d, 1H, J=8.4 Hz), 4.27 (t, 1H, J=3.9 Hz), 4.15-4.08 (m, 2H), 3.47 (d, 1H, J=4.5 Hz), 2.43 (d, 1H, J=3.6 Hz), 2.30-2.20 (m, 1H), 1.93-1.78 (m, 1H), 1.75-1.65 (m, 2H), 1.44 (s, 9H). $^{13}$C NMR (CDCl$_3$) δ 155.61, 149.65, 148.52, 138.89, 137.47, 124.55, 80.57, 80.14, 63.10, 60.44, 54.20, 30.39, 28.45, 20.47. Anal. Calcd for (C$_{16}$H$_{21}$ClN$_2$O$_3$. 1/10H$_2$O) C, 58.84; H, 6.54; N, 8.58. Found: C, 58.58; H, 6.28; N, 8.42.

7-tert-Butoxycarbonyl-2-exo-(2-chloro-5-pyridyl)-5-exo-fluoro-7-azabicyclo[2.2.1]heptane: To a stirred solution of 7-tert-butoxycarbonyl-2-exo-(2-chloro-5-pyridyl)-5-endo-hydroxyl-7-azabicyclo[2.2.1]heptane (42 mg, 0.13 mmol) in dry CH$_2$Cl$_2$ (3 mL) at −78° C. under N$_2$ was slowly added diethylaminosulfur trifluoride (66 μL, 0.5 mmol). The reaction mixture was stirred at −78° C. for 1 h, and then warmed slowly to room temperature. After that the reaction mixture was quenched by adding saturated aqueous NaHCO$_3$, and diluted with EtOAc. The organic layer was washed with brine, dried over Na$_2$SO$_4$, and concentrated. The residue was purified by chromatography with hexane-EtOAc (5:1) to give the product (35 mg, 87%). $^1$H NMR (CDCl$_3$) δ 8.29 (d, 1H, J=2.4 Hz), 7.61 (dd, 1H, J=8.4, 2.4 Hz), 7.27 (d, 1H, J=8.4 Hz), 5.14 (d, 1H, J=57.3 Hz), 4.53 (s, 1H), 4.16 (s, 1H), 3.06 (dd, 1H, J=9.3, 5.1 Hz), 2.67 (ddd, 1H, J=13.2, 9.3, 2.4 Hz), 2.35 (m, 1H), 1.80 (m, 1H), 1.62 (ddd, 1H, J=24.9, 13.8, 2.1 Hz), 1.42 (s, 9H). $^{13}$C NMR 2.35 (m, 1H), 1.80 (m, 1H), 1.62

(ddd, 1H, J=24.9, 13.8, 2.1 Hz), 1.42 (s, 9H). $^{13}$C NMR (CDCl$_3$) δ 154.59, 149.87, 148.92, 139.63, 137.45, 124.40, 90.14 (d, J=191 Hz), 80.97, 62.24, 58.32, 44.59, 38.10, 31.77, 28.43. $^{19}$F NMR (CDCl$_3$) δ-114 (d, J=191 Hz).

7-tert-Butoxycarbonyl-2-exo-(2-chloro-5-pyridyl) exo-fluoro-7-azabicyclo[2.2.1]heptane: Yield, 83%. $^1$H NMR (CDCl$_3$) δ 8.31 (d, 1H, J=2.4 Hz), 7.62 (dd, 1H, J=8.4, 2.4 Hz), 7.27 (d, 1H, J=8.4 Hz), 5.12 (d, 1H, J=57 Hz), 4.37 (s, 1H), 4.32 (s, 1H), 3.62 (dd, 1H, J=9.0, 5.1 Hz), 2.30 (m, 1H), 2.19 (dd, 1H, J=12.3, 9.0 Hz), 1.95 (m, 1H), 1.53 (ddd, 1H, J=25.2, 13.8, 2.4 Hz), 1.41 (s, 9H). $^{13}$C NMR (CDCl$_3$) δ 154.59, 149.87, 149.25, 138.99, 137.93, 124.35, 90.06 (d, J=194 Hz), 80.97, 63.75, 56.85, 39.78, 36.54, 35.95, 28.41. $^{19}$F NMR (CDCl$_3$) δ-115 (d, J=293 Hz).

2-endo-(2-Chloro-5-pyridyl)-3-exo-hydroxyl-7-azabicyclo[2.2.1]heptane.

General procedure for removal of Boc group: To a solution of 7-tert-butoxycarbonyl-2-endo-(2-chloro-5-pyridyl)-3-exo-hydroxyl-7-azabicyclo[2.2.1]heptane (90 mg, 0.28 mmol) in CH$_2$Cl$_2$ (6 mL) under N$_2$ was added trifluoroacetic acid (500 μL). The reaction mixture was stirred at room temperature for 3 h and then rendered basic with saturated aq. Na$_2$CO$_3$. The mixture was diluted with EtOAc (100 mL) and the organic phase was washed with brine, dried over Na$_2$SO$_4$, and concentrated. The residue was purified by chromatography with CH$_2$Cl$_2$-MeOH (2:1) to give the product (58 mg, 94%). $^1$H NMR (CDCl$_3$) δ 8.23 (d, 1H, J=2.4 Hz), 7.45 (dd, 1H, J=8.4, 2.4 Hz), 7.29 (d, 1H, J=8.4 Hz), 4.00 (d, 1H, J=3.0 Hz), 4.78 (t, 1H, J=4.5 Hz), 3.57 (d, 1H, J=5.7 Hz), 2.99 (s, 1H), 2.35 (br s, 2H), 1.76-1.62 (m, 1H), 1.46-1.15 (m, 3H). $^{13}$C NMR (CDCl$_3$) δ 149.78, 149.37, 138.42, 134.08, 124.17, 78.88, 64.78, 60.38, 57.73, 25.43, 23.12. Anal. Calcd for (C$_{11}$H$_{13}$ClN$_2$O.1/4HCl) C, 56.51; H, 5.71; N, 11.98. Found: C, 56.86; H, 5.31; N, 11.64.

2-endo-(2-Chloro-5-pyridyl)-3-endo-hydroxyl-7-azabicyclo[2.2.1]heptane: Yield, 95%. $^1$H NMR (CDCl$_3$) δ 8.23 (d, 1H, J=2.4 Hz), 7.66 (dd, 1H, J=8.4, 2.4 Hz), 7.26 (d, 1H, J=8.4 Hz), 4.46 (dd, 1H, J=9.0, 3.9 Hz), 3.75 (s, 1H), 3.64 (s, 1H), 3.18 (dd, 1H, J=8.4, 3.9 Hz), 2.49 (br s, 2H), 2.20 (m, 1H), 1.69 (m, 1H), 1.56-1.38 (m, 2H). $^{13}$C NMR (CDCl$_3$) δ 151.91, 149.57, 141.75, 132.10, 123.46, 70.86, 62.54, 61.88, 47.54, 24.02, 21.76. Anal. Calcd for (C$_{11}$H$_{13}$ClN$_2$O.1/3H$_2$O) C, 57.27; H, 5.97; N, 12.14. Found: C, 56.99; H, 5.89; N, 11.74.

2-exo-2-Chloro-5-pyridyl)-3-exo-hydroxyl-7-azabicyclo[2.2.1]heptane: Yield, 90%. $^1$H NMR (CDCl$_3$) δ 8.25 (d, 1H, J=2.4 Hz), 7.70 (dd, 1H, J=8.1, 2.4 Hz), 7.26 (d, 1H, J=8.1 Hz), 3.98 (d, 1H, J=6.9 Hz), 3.67 (s, 1H), 3.59 (d, 1H, J=5.1 Hz), 2.90 (d, 1H, J=6.9 Hz), 2.06 (br s, 2H), 1.71-1.62 (m, 1H), 1.58-1.50 (m, 2H), 1.48-1.38 (m, 1H). $^{13}$C NMR (CDCl$_3$) δ 150.13, 149.53, 139.47, 134.31, 123.90, 76.40, 63.02, 61.53, 51.48, 31.30, 25.08. Anal. Calcd for (C$_{11}$H$_{13}$ClN$_2$O.1/2H$_2$O) C, 56.53; H. 6.04; N, 11.99. Found: C, 56.92; H, 5.99; N, 11.69.

2-exo-(2-Chloro-5-pyridyl)-3-endo-hydroxyl-7-azabicyclo[2.2.1]heptane: Yield, 93%. $^1$H NMR (CDCl$_3$) δ 8.29 (d, 1H, J=2.4 Hz), 7.84 (dd, 1H, J=8.4, 2.4 Hz), 7.24 (d, 1H, J=8.4 Hz), 4.08 (td, 1H, J=4.2, 1.2 Hz), 3.68 (t, 1H, J=4.5 Hz), 3.54 (d, 1H, J=4.5 Hz), 2.32 (br s, 2H), 2.29 (d, 1H, J=3.9 Hz), 2.24 (ddd, 1H, J=12.6, 8.7, 5.7 Hz), 1.74 (m, 1H), 1.65 (tt, 1H, J=12.0, 4.8 Hz), 1.50 (tt, 1H, J=12.0, 4.5 Hz). $^{13}$C NMR (CDCl$_3$) δ 149.42, 148.78, 139.72, 137.95, 124.30, 81.16, 64.25, 60.92, 53.54, 32.46, 22.13. Anal. Calcd for (C$_{11}$H$_{13}$ClN$_2$O.1/2H$_2$O) C, 56.53; H, 6.04; N, 11.99. Found: C, 56.48; H, 5.70; N, 11.73.

2-exo-(2-Chloro-5-pyridyl)-5-exo-fluoro-7-azabicyclo[2.2.1]heptane: Yield, 87%. $^1$H NMR (CDCl$_3$) δ 8.32 (d, 1H, J=2.7 Hz), 7.73 (dd, 1H, J=8.4, 2.7 Hz), 7.26 (d, 1H, J=8.4 Hz), 5.08 (dddd, 1H, J=57.6, 7.2, 4.8, 2.4 Hz), 3.88 (t, 1H, J=4.8 Hz), 3.50 (d, 1H, J=5.1 Hz), 2.99 (dd, 1H, J=9.3, 5.1 Hz), 2.61 (ddd, 1H, J=12.9, 9.0, 2.4 Hz), 2.11 (m, 1H), 1.65 (br s, 1H), 1.61 (dd, 1H, J=13.5, 5.7 Hz), 1.55 (ddd, 1H, J=24.9, 13.8, 2.4 Hz). $^{13}$C NMR (CDCl$_3$) δ 149.52, 148.95, 140.78, 137.89, 124.26, 92.69 (d, J=189 Hz), 63.13 (d, J=3 Hz), 59.08 (d, J=20 Hz), 44.36, 39.25 (d, J=24 Hz), 32.05 (d, J=8 Hz). $^{19}$F NMR (CDCl$_3$) δ-113 (dt, J=58, 21 Hz). Anal. Calcd for (C$_{11}$H$_{12}$ClFN$_2$.0.5H$_2$O) C, 57.15; H, 5.45; N, 12.12. Found: C, 57.14; H, 5.54; N, 11.85.

2-exo-(2-Chloro-5-pyridyl)-6-fluoro-7-azabicyclo[2.2.1]heptane: Yield, 92%. $^1$H NMR (CDCl$_3$) δ 8.35 (d, 1H, J=2.4 Hz), 7.74 (dd, 1H, J=8.4, 2.4 Hz), 7.26 (d, 1H, J=8.4 Hz), 5.06 (dddd, 1H, J=58, 9.9, 4.8, 2.7 Hz), 3.76 (t, 1H, J=4.8 Hz), 3.64 (d, 1H, J=4.5 Hz), 3.56 (dd, 1H, J=9.0, 5.4 Hz), 2.14 (dd, 1H, J=12.6, 9.0 Hz), 2.10 (m, 1H), 1.78 (m, 1H), 1.70 (br s, 1H), 1.46 (ddd, 1H, J=25.2, 13.5, 2.7 Hz). $^{13}$C NMR (CDCl$_3$) δ 149.54, 149.25, 140.18, 138.30, 124.23, 92.59 (d, J=191 Hz), 65.30 (d, J=19 Hz), 57.32 (d, J=3 Hz), 40.10, 37.45 (d, J=23 Hz), 35.57 (d, J=8 Hz). $^{19}$F NMR (CDCl$_3$) δ-115 (ddd, J=58, 25, 15 Hz). Anal. Calcd for (C$_{11}$H$_{12}$ClFN$_2$.0.3H$_2$O) C, 56.93; H, 5.47; N, 12.07. Found: C, 57.19; H, 5.56; N, 11.67.

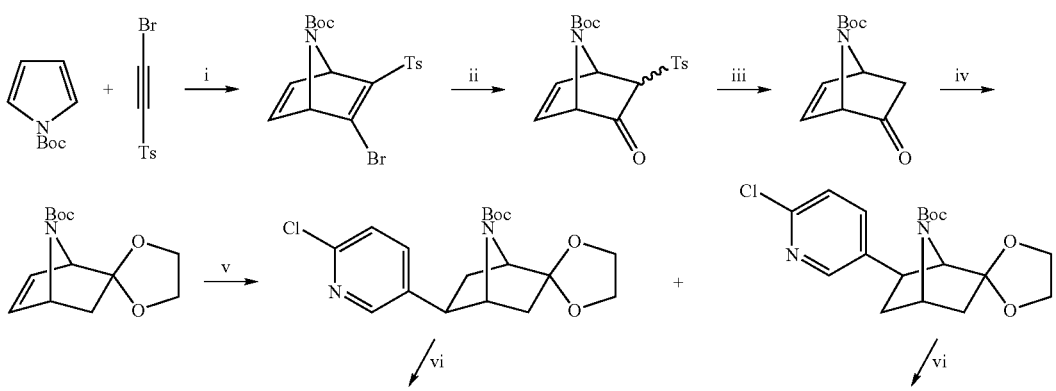

-continued

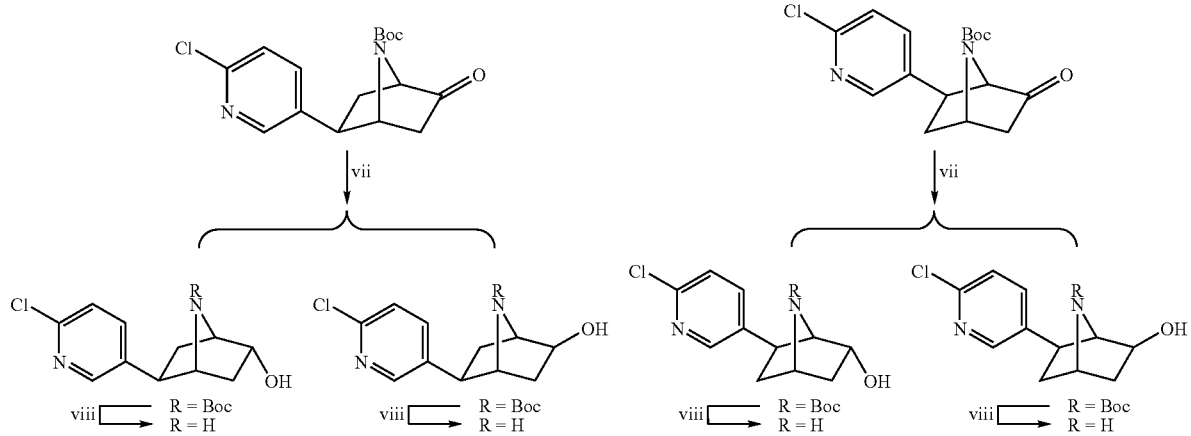

Reagents and conditions: (i) Toluene, 70° C., 78%. (ii) a) Et₂NH, Et₃N; b) conc. HCl, 85%. (iii) SmI₂ (2 equiv), THF—MeOH, -78° C. to rt, 95%. (iv) HOCH₂CH₂OH, (EtO)₃CH, p-TsOH (cat.), THF, 64%. (v) 2-Chloro-5-iodopyridine, Pd(PPh₃)₄ (cat.), piperidine, HCO₂H, DMF, 75° C., 92%. (vi) a). HClO₄; b). Boc₂O, Et₃N, THF, 77-83% for two steps. (vii) SmI₂, THF—H₂O. (viii) CF₃COOH, CH₂Cl₂, 93-97%.

1-Bromo-2-p-tolylsulfonylacetylene: To a stirred solution of trimethylsilyl p-tolylsulfonylacetylene (10 g, 40 mmol) in acetone (300 mL) was added silver nitrate (0.68 g, 4 mmol) followed by the addition of N-bromosuccinimide (7.6 g, 44 mmol) in one portion. The mixture was stirred at room temperature for 1 h. The resulting precipitate was filtered and washed with acetone. Silica gel (20 g) was added to the filtrate and the solvent was removed under reduced pressure. The residue was subjected to column chromatography with hexane/EtOAc (5:1) to afford the product as a light yellow solid (10 g, 96%). Mp. 99-101° C. $^1$H NMR (CDCl₃) δ 7.87 (d, 2H, J=7.8 Hz), 7.39 (d, 2H, J=7.8 Hz), 2.47 (s, 3H); $^{13}$C NMR (CDCl₃) δ 146.19, 138.16, 130.34, 127.83, 78.14, 61.70, 21.97.

7-tert-Butoxycarbonyl-2-bromo-3-p-tolylsulfonyl)-7-azabicyclo[2.2.1]hept-2,5-diene A mixture of Boc-pyrrole (6.43 g, 38.4 mmol), toluene (10 mL), and 1-bromo-2-p-tolylsulfonylacetylene (5 g, 19.2 mmol) was stirred at 90° C. under N₂ for 24 h. After cooled to room temperature, the reaction mixture was passed through a short silica gel column. The crude product was purified by chromatography with n-Hexane/EtOAc (5:1) to afford a light yellow syrup (5.8 g, 71%). $^1$H NMR (CDCl₃) δ 7.81 (d, 2H, J=8.1 Hz), 7.36 (d, 2H, J=8.1 Hz), 6.98 (s, 1H), 6.97 (br s, 1H), 5.38 (s, 1H), 5.17 (br s, 1H). 2.45 (s, 3H), 1.31 (s, 9H).

7-tert-Butoxycarbonyl-2-oxo-3-p-tolylsulfonyl)-7-azabicyclo[2.2.1]hept-5-ene:

To a stirred solution of 7-tert-butoxycarbonyl-2-bromo-3-p-tolylsulfonyl)-7-azabicyclo[2.2.1]hept-2,5-diene (5.7 g, 13.4 mmol) and triethylamine (9.5 mL, 67 mmol) in acetonitrile (35 mL) was added dropwise a solution of diethylamine (1.5 mL, 15 mmol) in acetonitrile (20 mL) under N₂. The mixture was stirred at room temperature for 1.5 h. A 10% HCl (45 mL) solution was then added dropwise. The mixture was stirred for additional 4 h. Water (40 mL) was added and the mixture was extracted with CH₂Cl₂ (50 mL×3). The combined organic layer was washed with brine, dried over MgSO₄, and concentrated. The residue was purified by chromatography with hexane-EtOAc (2:1) to give the product as a mixture (4.1 g, 84%). 2-α isomer: $^1$H NMR (CDCl₃) δ 7.81 (d, 1H, J=8.1 Hz), 7.38 (d, 1H, J=8.1 Hz), 6.96 (dd, 1H, J=6.0, 2.1 Hz), 4.27 (ddt, 1H, J=5.4, 2.7, 0.9 Hz), 5.19 (s, 1H), 4.70 (s, 1H), 4.01 (d, 1H, J=3.9 Hz), 2.46 (s, 3H), 1.42 (s, 9H). 2β isomer: $^1$H NMR (CDCl₃) δ 7.77 (d, 1H, J=8.1 Hz), 7.32 (d, 1H, J=8.1 Hz), 6.76 (d, 1H, J=3.6 Hz), 6.55 (s, 1H), 5.45 (s, 1H), 4.57 (s, 1H), 3.55 (s, 1H), 2.43 (s, 3H), 1.41 (s, 9H).

7-tert-Butoxycarbonyl-2-oxo-7-azabicyclo[2.2.1]hept-5-ene:

7-tert-Butoxycarbonyl-2-oxo-3-(p-tolylsulfonyl)-7-azabicyclo[2.2.1]hept-5-ene (2.4 g, 6.6 mmol) in THF (20 mL) and MeOH (10 mL) was added to 140 mL of a solution of SmI₂ (0.1 M in THF, 14 mmol) at −78° C. under N₂. The resultant brown mixture was stirred for 10 min at −78° C. and then warmed to room temperature. The reaction mixture was quenched by adding saturated aq. K₂CO₃, and filtered. The filtrate was concentrated in vacuo and the residue was dissolved in EtOAc (100 mL), washed with brine, dried over Na₂SO₄, and concentrated. The residue was purified by chromatography with n-hexane-EtOAc (5:1) to give a light yellow oil (1.31 g, 95%). $^1$H NMR (CDCl₃) δ 6.73 (dd, 1H, J=5.4, 1.8 Hz), 6.42 (d, 1H, J=4.2 Hz), 5.06 (s, 1H), 4.55 (s, 1H), 2.29 (dd, 1H, J=15.9, 3.9 Hz), 1.91 (d, 1H, J=15.9 Hz), 1.44 (s, 9H); $^{13}$C NMR (CDCl₃) δ 205.48, 155.18, 143.10, 130.61, 81.86, 68.38, 60.20, 35.98, 28.29.

Preparation of the 1,3-dioxolane from 7-tert-butoxycarbonyl-2-oxo-7-azabicyclo[2.2.1]hept-5-ene: A solution of 7-tert-Butoxycarbonyl-2-oxo-7-azabicyclo[2.2.1]hept-5-ene (460 mg, 2.2 mmol), THF (2 mL), ethylene glycol (0.24 mL, 4.4 mmol), triethyl orthoformate (0.56 mL, 3.4 mmol) and PTSA (50 mg) was stirred at room temperature for 3 days. The reaction mixture was concentrated and the residue was purified by chromatography with hexane-EtOAc (5:1) to give the 1,3-dioxolane (355 mg, 64%). $^1$H NMR (CDCl₃) δ 6.60-6.30 (m, 2H), 4.73 (s, 1H), 4.35 (m, 1H), 4.10-3.85 (m, 4H), 2.19 (dd, 1H, J=12.0, 3.9 Hz), 1.55 (d, 1H, J=12.0 Hz), 1.42 (s, 9H).

2 (2-Choro-5-pyridyl)-7-azabicyclo[2.2.1]heptan-5-one and 2-exo-(2-chloro-5-pyridyl)-7-azabicyclo[2.2.1]heptan-6-one: To a stirred mixture of the above 1,3-dioxolane (330 mg, 1.31 mmol), 2-chloro-5-iodopyridine (0.85 g, 3.95 mmol), Pd(PPh₃)₄ (230 mg, 0.2 mmol) in DMF (3 mL) at room temperature under argon was added piperidine (0.45 mL, 4.6 mmol) and formic acid (0.15 mL, 3.95 mmol). The reaction mixture was stirred at 75° C. for 48 h. The solvent was removed in vacuo and the residue was dissolved in EtOAc (100 mL), washed with brine, dried over Na₂SO₄, and concentrated. The resulting residue was purified by chromatography with hexane-EtOAc (4:1) to give a syrup (445 mg, 92%).

The above syrup was dissolved in $CH_2Cl_2$ (0.5 mL) and 70% $HClO_4$ (1 mL) was added. The reaction mixture was stirred at room temperature for 5 h. The solution was adjusted to pH=7 with aq. $NaHCO_3$. The mixture was extracted with EtOAc. The organic layers were combined, washed with brine, dried and concentrated. The residue was purified by chromatography with EtOAc. 2-exo-(2-Chloro-5-pyridyl)-7-azabicyclo[2.2.1]heptan-5-one: $^1$H NMR ($CDCl_3$) δ 8.37 (d, 1H, J=2.7 Hz), 7.87 (dd, 1H, J=8.4, 2.7 Hz), 7.28 (d, 1H, J=8.4 Hz), 3.87 (d, 1H, J=5.4 Hz), 3.74 (d, 1H, J=5.4 Hz), 3.00 (dd, 1H, J=9.0, 4.8 Hz), 2.33 (dd, 1H, J=18.0, 5.4 Hz), 2.24-2.15 (m, 2H), 1.90 (dt, 1H, J=13.5, 5.4 Hz); $^{13}$C NMR ($CDCl_3$) δ 214.38, 149.70, 148.86, 139.77, 137.89, 124.15, 63.82, 61.87, 46.23, 42.70, 34.18. 2-exo-(2-Chloro-5-pyridyl)-7-azabicyclo[2.2.1]heptan-6-one: $^1$H NMR ($CDCl_3$) δ 8.37 (d, 1H, J=2.4 Hz), 7.81 (dd, 1H, J=8.4, 2.4 Hz), 7.27 (d, 1H, J=8.4 Hz), 4.18 (t, 1H, J=4.8 Hz), 3.53 (s, 1H), 3.07 (dd, 1H, J=9.0, 5.1 Hz), 2.32 (dq, 1H, J=18.0, 2.7 Hz), 2.23-2.12 (m, 2H), 2.00-1.91 (m, 1H); $^{13}$C NMR ($CDCl_3$) δ 213.42, 149.93, 148.85, 138.33, 137.89, 124.16, 70.12, 55.70, 45.38, 38.79, 38.44.

7-ter-Butoxycarbonyl-2-exo-(2-chloro-5-pyridyl)-7-azabicyclo[2.2.1]heptan-5-one:
$^1$H NMR ($CDCl_3$) δ 8.30 (d, 1H, J=2.4 Hz), 7.65 (dd, 1H, J=8.4, 2.4 Hz), 7.29 (d, 1H, J=8.4 Hz), 4.51 (d, 1H, J=5.1 Hz), 4.38 (d, 1H, J=5.7 Hz), 3.11 (dd, 1H, J=9.0, 5.1 Hz), 2.55 (dd, 1H, J=17.7, 5.4 Hz), 2.31-2.03 (m, 3H), 1.44 (s, 9H); $^{13}$C NMR ($CDCl_3$) δ 208.72, 154.45, 149.98, 148.53, 138.24, 137.08, 124.29, 81.57, 63.64, 62.18, 44.62, 43.20, 34.28, 28.08.

7-tert-Butoxycarbonyl-2-exo-(2-chloro-5-pyridyl)-7-azabicyclo[2.2.1]heptan-6-one: $^1$H NMR ($CDCl_3$) δ 8.29 (d, 1H, J=2.4 Hz), 7.61 (dd, 1H, J=8.4, 2.4 Hz), 7.27 (d, 1H, J=8.4 Hz), 4.76 (t, 1H, J=4.8 Hz), 4.20 (s, 1H), 3.17 (dd, 1H, J=9.0, 5.1 Hz), 2.52 (dq, 1H, J=18.0, 2.4 Hz), 2.23 (dd, 1H, J=12.9, 9.0 Hz), 2.15 (d, 1H, J=18.0 Hz), 2.07 (m, 1H), 1.41 (s, 9H); $^{13}$C NMR ($CDCl_3$) δ 208.03, 154.34, 150.17, 148.59, 137.30, 136.88, 124.26, 81.53, 69.13, 56.41, 43.97, 39.84, 38.11, 28.08. MS m/z (%): 324 ($[M+2]^+$, 0.3), 322 ($M^+$, 0.8), 294 (12), 266 (38), 240 (31), 238 (95), 194 (53), 179 (33), 167 (55), 142 (34), 140 (100), 126 (28).

General procedure for $SmI_2$ reduction of the ketone: 7-tert-Butoxycarbonyl-2-exo-(2-chloro-5-pyridyl)-7-azabicyclo[2.2.1]heptan-5-one (32 mg, 0.1 mmol) in 1 mL of THF and 0.5 mL of water was added to a solution of $SmI_2$ (0.1 M in THF, 2 mL, 0.2 mmol) at room temperature under $N_2$. After 10 min 1 M HCl was added and the mixture was diluted with EtOAc (20 mL). The organic phase was isolated and washed with brine, dried over $Na_2SO_4$, and concentrated. The residue was purified by chromatography with hexane-EtOAc (2:1 to 1:1) to give the two alcohols.

7-tert-Butoxycarbonyl-2-exo-(2-chloro-5-pyridyl)-5-endo-hydroxyl-7-azabicyclo[2.2.1]heptane: $^1$H NMR ($CDCl_3$) δ 8.27 (d, 1H, J=2.1 Hz), 7.62 (dd, 1H, J=8.4, 2.1 Hz), 7.26 (d, 1H, J=8.4 Hz), 4.43 (s, 1H), 4.31 (s, 1H), 4.10 (s, 1H), 3.03 (dd, 1H, J=9.0, 4.5 Hz), 2.79 (dd, 1H, J=12.6, 9.0 Hz), 2.52 (br s, 1H), 2.33 (s, 1H), 1.70 (dtd, 1H, J=12.9, 4.8, 1.2 Hz), 1.42 (s, 9H), 1.32 (dd, 1H, J=12.9, 3.0 Hz); $^{13}$C NMR ($CDCl_3$) δ 155.00, 149.56, 148.86, 140.20, 137.58, 124.34, 80.53, 70.16, 63.07, 59.82, 45.17, 40.01, 31.19, 28.45. MS m/z (%): 326 ($[M+2]^+$, 0.1), 324 ($M^+$, 0.3), 268 (2), 226 (9), 224 (28), 179 (12), 142 (33), 140 (100).

7-tert-Butoxycarbonyl-2-exo-(2-chloro-5-pyridyl)-5-exo-hydroxyl -7-azabicyclo[2.2.1]heptane: $^1$H NMR ($CDCl_3$) δ 8.24 (d, 1H, J=2.7 Hz), 7.60 (dd, 1H, J=8.4, 2.7 Hz), 7.25 (d, 1H, J=8.4 Hz), 4.35 (d, 1H, J=4.2 Hz), 4.24 (d, 1H, J=4.8 Hz), 4.13 (tt?, 1H, J=4.5, 1.8 Hz), 2.76 (dd, 1H, J=8.7, 4.5 Hz), 2.40 (br s, 1H), 2.04 (dd, 1H, J=13.5, 6.9 Hz), 1.90 (dd, 1H, J=13.2, 8.7 Hz), 1.80 (dt, 1H, J=13.2, 4.8 Hz), 1.71 (dd, 1H, J=13.5, 3.9 Hz), 1.44 (s, 9H); $^{13}$C NMR ($CDCl_3$) δ 155.79, 149.50, 148.70, 139.28, 137.20, 124.08, 80.45, 74.62, 62.66, 61.11, 43.78, 41.94, 34.37, 28.27.

7-tert-Butoxycarbonyl-2-exo-(2-chloro-5-pyridyl)-6-endo-hydroxyl-7-azabicyclo[2.2.1]heptane: $^1$H NMR ($CDCl_3$) δ 8.30 (d, 1H, J=2.4 Hz), 7.66 (dd, 1H, J=8.4, 2.4 Hz), 7.25 (d, 1H, J=8.4 Hz), 4.42 (s, 1H), 4.30 (s, 1H), 4.09 (s, 1H), 3.78 (dd, 1H, J=9.0, 5.4 Hz), 2.51 (br s, 1H), 2.29 (s, 1H), 2.14 (dd, 1H, J=12.3, 9.0 Hz), 1.86 (m, 1H), 1.42 (s, 9H), 1.23 (dd, 1H, J=12.9, 3.0 Hz); $^{13}$C NMR ($CDCl_3$) δ 154.79, 149.06, 148.73, 139.97, 137.88, 124.20, 80.25, 69.97, 65.78 and 65.22 (br), 57.52 and 56.65 (br), 40.89 and 40.00 (br), 37.90, 35.49 (br), 28.19.

7-tert-Butoxycarbonyl-2-exo-(2-chloro-5-pyridyl)-6-exo-hydroxyl -7-azabicyclo[2.2.1]heptane: $^1$H NMR ($CDCl_3$) δ 8.26 (d, 1H, J=2.4 Hz), 7.61 (dd, 1H, J=8.4, 2.4 Hz), 7.26 (d, 1H, J=8.4 Hz), 4.45 (t, 1H, J=4.5 Hz), 4.17-4.12 (m, 2H), 2.75 (dd, 1H, J=9.0, 5.4 Hz), 2.25 (br s, 1H), 1.96 (dd, 1H, J=13.2, 6.6 Hz), 1.88 (dd, 1H, J=12.3, 9.0 Hz), 1.76-1.63 (m, 2H), 1.44 (s, 9H); $^{13}$C NMR ($CDCl_3$) δ 155.71, 149.56, 148.65, 138.85, 137.30, 124.21, 80.43, 74.77, 68.47, 55.30, 41.19, 40.01, 39.25, 28.27.

General procedure for the removal of the Boc group: To a solution of Boc protected starting material in $CH_2Cl_2$ (1 mL) was added dropwise with stirring under $N_2$ trifluoroacetic acid (100 μL). The reaction mixture was stirred at room temperature for 3 h and then rendered basic with saturated aq. $Na_2CO_3$. The mixture was diluted with EtOAc (20 mL) and the organic phase was washed with brine, dried over $Na_2SO_4$, and concentrated. The residue was purified by chromatography with $CH_2Cl_2$/MeOH (2:1) to give the product.

2-exo-(2-Chloro-5-pyridyl)-5-endo-hydroxyl-7-azabicyclo[2.2.1]heptane: $^1$H NMR ($CDCl_3$) δ 8.31 (d, 1H, J=2.4 Hz), 7.72 (dd, 1H, J=8.4, 2.4 Hz), 7.25 (d, 1H, J=8.4 Hz), 4.35 (dtd, 1H, J=10.2, 3.9, 1.2 Hz), 3.68 (t, 1H, J=4.5 Hz), 3.48 (d, 1H, J=5.1 Hz), 2.97 (dd, 1H, J=9.0, 4.5 Hz), 2.70 (dd, 1H, J=12.6, 9.0 Hz), 2.13 (ddd, 1H, J=12.9, 9.9, 5.4 Hz), 1.80 (br s, 2H), 1.55 (dtd, 1H, J=12.6, 4.8, 1.2 HZ), 1.24 (dd, 1H, J=12.9, 3.3 Hz); $^{13}$C NMR ($CDCl_3$) δ 149.34, 148.97, 141.05, 137.90, 124.21, 72.50, 63.75, 60.71, 45.04, 41.23, 31.74.

2-exo-(2-Chloro-5-pyridyl)-5-exo-hydroxyl-7-azabicyclo[2.2.1]heptane: $^1$H NMR ($CDCl_3$) δ 8.28 (d, 1H, J=2.4 Hz), 7.81 (dd, 1H, J=8.4, 2.4 Hz), 7.25 (d, 1H, J=8.4 Hz), 4.07 (dd, 1H, J=6.3, 1.5 Hz), 3.56 (d, 1H, J=5.7 Hz), 3.54 (d, 1H, J=4.8 Hz), 2.64 (dd, 1H, J=9.0, 4.2 Hz), 1.98 (dd, 1H, J=13.5, 6.3 Hz), 1.84 (br s, 2H), 1.75 (dd, 1H, J=13.2, 9.0 Hz), 161 (dt 1H, J=12.9, 4.8 Hz), 1.42 (dd, 1H, J=13.5, 4.8 Hz); $^{13}$C NMR ($CDCl_3$), δ 149.46, 149.12, 140.54, 138.06, 124.19, 74.34, 63.63, 61.82, 43.61, 34.14.

2-exo-(2-Chloro-5-pyridyl)-6-endo-hydroxyl-7-azabicyclo[2.2.1]heptane: $^1$H NMR ($CDCl_3$) δ 8.34 (d, 1H, J=2.7 Hz), 7.74 (dl, 1H, J=8.4, 2.7 Hz), 7.25 (d, 1H, J=8.4 Hz), 4.34 (dt, 1H, J=10.2, 4.5 Hz), 3.71 (t, 1H, J=5.4 Hz), 3.69 (dd, 1H, J=9.3, 5.4 Hz), 3.44 (d, 1H, J=4.8 Hz), 2.11 (m, 1H), 2.10 (dd, 1H, J=12.6, 9.3 Hz), 1.72 (m, 1H), 1.68 (br s, 2H), 1.16 (dd, 1H, J=12.6, 3.9 Hz); $^{13}$C NMR ($CDCl_3$) δ 149.29, 149.00, 140.76, 138.07, 123.98, 72.59, 66.82, 57.67, 40.77, 39.18, 35.10.

2-exo-(2-Chloro-5-pyridyl)-6-exo-hydroxyl-7-azabicyclo[2.2.1]heptane: $^1$H NMR ($CDCl_3$) δ 8.28 (d, 1H, J=2.4 Hz), 7.78 (dd, 1H, J=8.4, 2.4 Hz), 7.25 (d, 1H, J=8.4 Hz), 4.08 (d, 1H, J=5.7 Hz), 3.79 (t, 1H, J=4.5 Hz), 3.35 (s, 1H), 2.57 (dd, 1H, J=8.7, 5.7 Hz), 1.92 (dd, 1H, J=13.2, 6.3 Hz), 1.79 (dd, 1H, J=12.0, 8.7 Hz), 1.72 (br s, 2H), 1.58-1.49 (m, 1H), 1.45-1.36 (m, 1H); $^{13}$C NMR (CDCl$_3$) δ 149.25, 148.72, 137.75, 124.12, 74.33, 69.78, 55.33, 42.43, 39.77, 39.09.

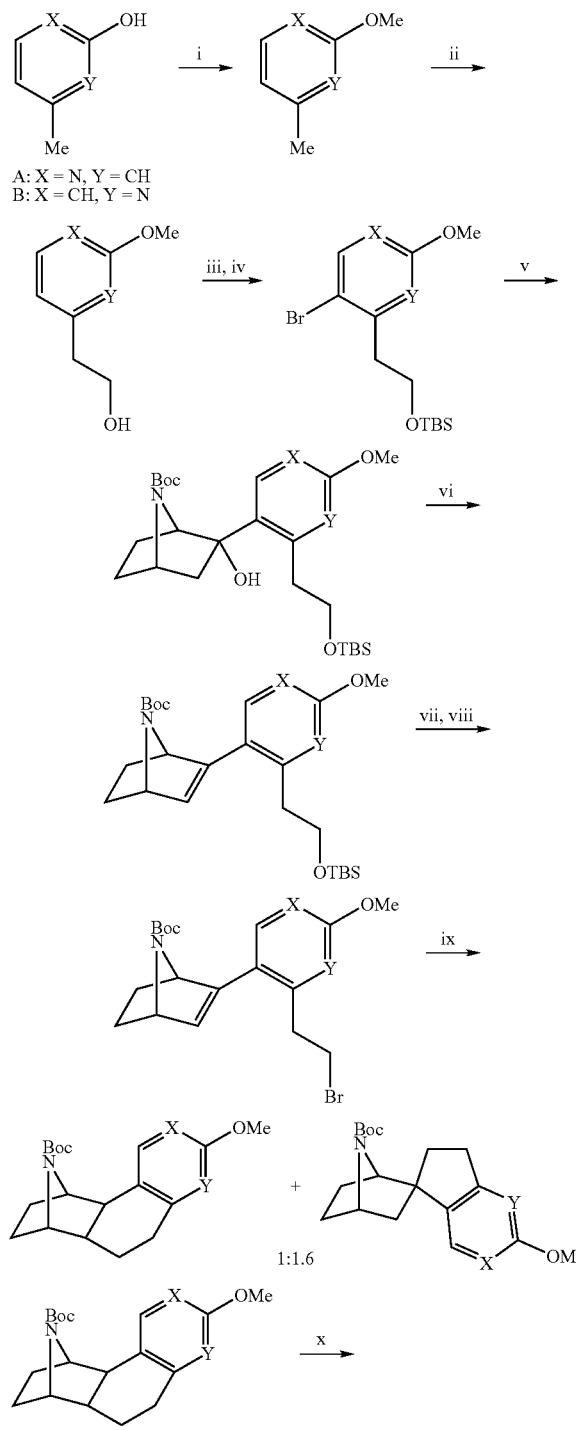

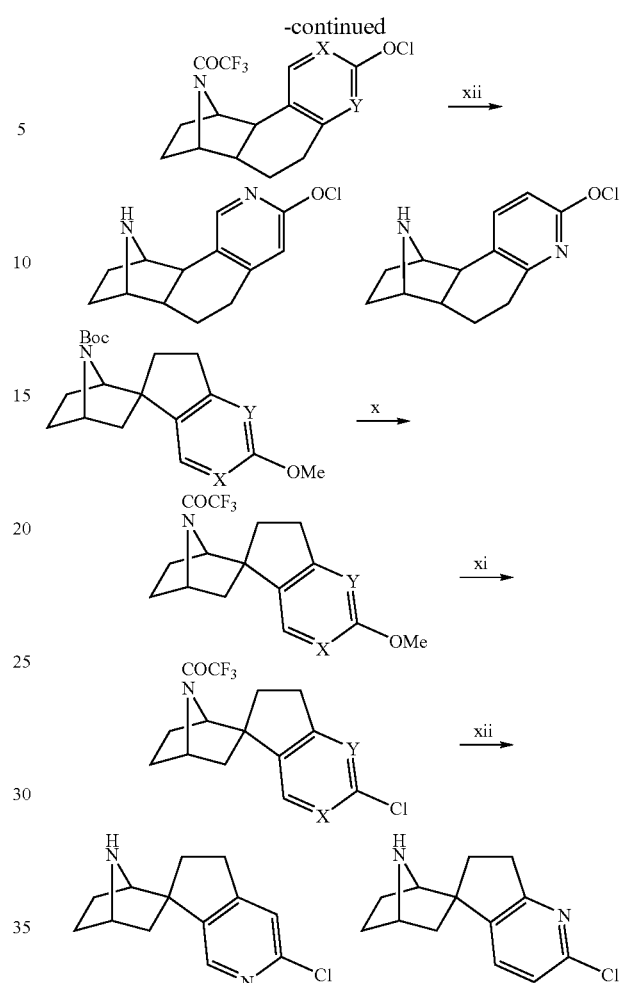

Reagents: (i) MeI, Ag$_2$CO$_3$, CHCl$_3$, 71-93%; (ii) n-BuLi, THF, then (CH$_2$O)$_n$, -78° C. to rt, 49-51%; (iii) Br$_2$, EtOH, 88-91%; (iv) TBSCl, imidazole, DMAP, DMF, 98%; (v) n-BuLi, THF then ketone, -78° C. to rt, 80-86%; (vi) MsCl, Et$_3$N, DMAP, CH$_2$Cl$_2$, 84-87%; (vii) n-Bu$_4$NF, THF, 100%; (viii) PPh$_3$, CBr$_4$, CH$_2$Cl$_2$, 87-88%; (ix) n-Bu$_3$SnH, AIBN, toluene, reflux, 85-87%. (x) a) CF$_3$CO$_2$H, CH$_2$Cl$_2$; b) (CF$_3$CO)$_2$O, pyridine, CH$_2$Cl$_2$; (xi) POCl$_3$, DMF, 0° C. to 95° C., 59-65%; (xii) NaOMe, MeOH, 85-96%.

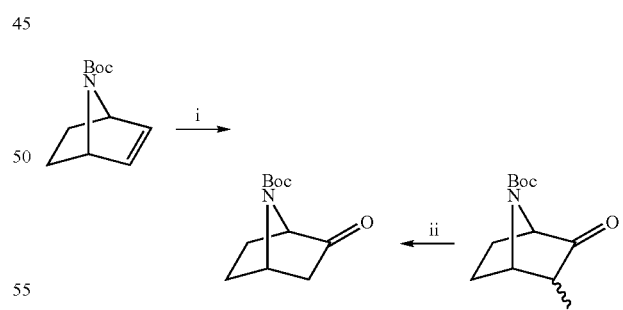

Reagents: (i) a) B$_2$H$_6$, THF, then aq. NaOH, 35% H$_2$O$_2$, 46%; b) Dess-Martin periodinane, CH$_2$Cl$_2$, 99%; (ii) SmI$_2$ (2 equiv), THF—MeOH, -78° C. to rt, 90%.

7-tert-Butoxycarbonyl-7-azabicyclo[2.2.1]hept-2-ene: A solution of 7-tert-butoxycarbonyl-2-(p-tolylsulfonyl)-7-azabicyclo[2.2.1]hept-2-ene (11.5 g, 33 mmol), benzene (125 mL), n-Bu$_3$SnH (20 g, 68.7 mmol) and AIBN (300 mg) was refluxed under N$_2$ for 3 h and then cooled to room temperature, and concentrated. The residue was purified by chromatography with hexane/EtOAc (10:0 to 10:1) to give a colorless oil (15 g). The product was dissolved in THF (150 mL) and nBu4NF (1 M solution in THF, 46 mL) was added. The mixture was refluxed for 24 h and cooled to room temperature, and concentrated. The residue was by chromatography with hexane/ether (10:1) to give a colorless oil (4.4 g, 97%). $^1$H NMR (CDCl$_3$) δ 6.22 (s, 2H), 4.66 (s, 2H), 1.84 (m, 2H), 1.42 (s, 9H), 1.10 (d, 2H, J=7.5).

7-tert-Butoxycarbonyl-7-azabicyclo[2.2.1]heptan-2-one. Method A: To a solution of 7-tert-butoxycarbonyl-7-azabicyclo[2.2.1]hept-2-ene (3 g, 15.4 mmol) in THF (150 mL) at −78° C. under nitrogen was added 40 mL (40 mmol) of 1 M borane-THF complex in THF. The reaction mixture was warmed slowly to room temperature and stirred overnight at room temperature. Then the reaction mixture was quenched by sequentially addition of water (10 mL), aqueous NaOH (6 M, 10 mL), and hydrogen peroxide (30% w/w, 20 mL). The mixture was stirred at room temperature for 30 min. The solvent was removed under reduced pressure and the residue was partitioned between EtOAc (200 mL) and water (50 mL). The organic phase was washed with brine, dried over Na$_2$SO$_4$, and concentrated. The residue was purified by chromatography with hexane/EtOAc (3:1) to give 7-tert-butoxycarbonyl-2-exo-7-azabicyclo[2.2.1]heptan-2-ol as a colorless oil (1.5 g, 46%). $^1$H NMR (CDCl$_3$) δ 4.22 (t, 1H, J=4.5 Hz), 4.11 (d, 1H, J=4.5 Hz), 3.87 (dd, 1H, J=6.9, 1.8 Hz), 3.10 (br s, 1H), 1.81 (dd, 1H, J=12.9, 6.9 Hz), 1.76-1.58 (m, 3H), 1.45 (s, 9H), 1.30-1.20 (m, 2H); $^{13}$C NMR (CDCl$_3$) δ 156.38, 79.53, 73.89, 62.83, 55.11, 41.82, 28.08, 28.00, 23.80.

To a stirred solution of the above alcohol (1.2 g, 5.6 mmol) in methylene chloride (100 mL) was added Dess-Martin periodinane (2.75 g, 6.5 mmol). The reaction mixture was stirred overnight at room temperature. After removal of the solvent in vacuo, the residue was passed through a short silica gel column to give 7-tert-butoxycarbonyl-7-azabicyclo[2.2.1]heptan-2-one (1.18 g, 99%).

Method B: A solution of 7-tert-butoxycarbonyl-2-exo-tosyl-7-azabicyclo[2.2.1]heptane (500 mg, 1.4 mmol) in THF (4 mL) and MeOH (2 mL) was added to 28 mL (2.8 mmol) of SmI$_2$ (0.1 M solution in THF) at −78° C. under N$_2$. The resultant mixture was stirred for 10 min at −78° C. and then warmed to room temperature. The reaction mixture was quenched by adding saturated aq. K$_2$CO$_3$, and filtered. The filtrate was concentrated in vacuo and the residue was dissolved in EtOAc (50 mL), washed with brine, dried over Na$_2$SO$_4$, and concentrated. The residue was purified by chromatography with hexane/EtOAc (5:1) to give 7-tert-butoxycarbonyl-7-azabicyclo[2.2.1]heptan-2-one (260 mg, 90%). $^1$H NMR (CDCl$_3$) δ 4.56 (t, 1H, J=4.5 Hz), 4.25 (d, 1H, J=4.8 Hz), 2.48 (dd, 1H, J=17.1, 5.1 Hz), 2.10-1.92 (m, 3H), 1.69-1.55 (m, 2H), 1.46 (s, 9H); $^{13}$C NMR (CDCl$_3$) δ 209.41, 154.91, 80.65, 63.77, 55.90, 45.07, 28.04, 27.40, 24.26.

2-Methoxy-4-methylpyridine: To a stirred solution of 2-hydroxy-4-methylpyridine (10 g, 92 mmol) in chloroform (350 mL) was added at room temperature silver carbonate (34.2 g, 124 mmol) and iodomethane (130 g, 920 mmol). The reaction mixture was stirred in the dark for 48 h, and then filtered through Celite and washed with ether. The filtrate was concentrated below 20° C., and the residue was purified by chromatography with pentane/ether (5:1) to afford 2-methoxy-4-methylpyridine as a colorless oil (8.0 g, 71%). $^1$H NMR (CDCl$_3$) δ 8.02 (d, 1H, J=5.4 Hz), 6.69 (d, 1H, J=5.4 Hz), 6.55 (s, 1H), 3.91 (s, 3H), 2.28 (s, 3H); $^{13}$C NMR (CDCl$_3$) δ 164.40, 149.72, 146.31, 118.21, 110.88, 53.17, 20.81. MS m/z (%): 123 (M$^+$, 76), 122 (100).

2-Methoxy-6-methylpyridine: Yield, 93%; colorless oil. $^1$H NMR (CDCl$_3$) δ 7.44 (t, 1H, J=7.8 Hz), 6.71 (d, 1H, J=7.8 Hz), 6.53 (d, 1H, J=7.8 Hz), 3.91 (s, 3H), 2.45 (s, 3H); $^{13}$C NMR (CDCl$_3$) δ 163.60, 156.25, 138.68, 115.63, 107.03, 53.18, 24.14. MS m/z (%): 123 (M$^+$, 79), 122 (100).

4-(2-Hydroxyethyl)-2-methoxypyridine: To a stirred solution of 2-methoxy-4-methylpyridine (6 g, 49 mmol) in anhydrous THF (200 mL) at −78° C. under nitrogen was added dropwise 29.4 mL (73.5 mmol) of n-BuLi (2.5 M solution in hexanes). The mixture was stirred at −78° C. for 1 h, and then warmed slowly to 0° C. and stirred at 0° C. for 30 min. The mixture was recooled to −78° C. and paraformaldehyde (10 g) was added in one portion. The mixture was warmed slowly to room temperature and stirred at room temperature for 8 h. The reaction was quenched by addition of saturated aq. NH$_4$Cl and extracted with EtOAc (150 mL×3). The combined organic layers were washed with brine, dried (MgSO$_4$), and concentrated. The residue was purified by chromatography with hexane/EtOAc (2:1) to afford 4-(2-hydroxyethyl)-2-methoxypyridine as a colorless oil (3.8 g, 51%). $^1$H NMR (CDCl$_3$) δ 8.06 (d, 1H, J=5.1 Hz), 6.77 (d, 1H, J=5.1 Hz), 6.62 (s, 1H), 3.92 (s, 3H), 3.87 (t, 2H, J=6.6 Hz), 2.81 (t, 2H, J=6.6 Hz), 1.98 (br s, 1H); $^{13}$C NMR (CDCl$_3$) δ 164.48, 150.63, 146.71, 117.76, 110.91, 62.43, 53.34, 38.30. MS m/z (%): 153 (M, 73), 152 (100), 123 (48).

6-(2-Hydroxyethyl)-2-methoxypyridine: Yield, 49%; colorless oil. $^1$H NMR (CDCl$_3$) δ 7.49 (dd, 1H, J=8.4, 7.5 Hz), 6.72 (d, 1H, J=7.5 Hz), 6.60 (d, 1H, J=8.4 Hz), 4.46 (br s, 1H), 3.99 (t, 2H, J=5.4 Hz), 3.88 (s, 3H), 2.92 (t, 2H, J=5.4 Hz); $^{13}$C NMR (CDCl$_3$) δ 163.27, 157.88, 138.98, 115.56, 108.21, 61.70, 53.02, 38.35. MS m/z (%): 153 (M$^+$, 22), 152 (15), 136 (68), 123 (100).

5-Bromo-4-(2-hydroxyethyl)-2-methoxypyridine: Bromine (2.95 g, 18.4 mmol) was slowly added to a stirred solution of 4-(2-hydroxyethyl)-2-methoxypyridine (1.4 g, 9.2 mmol) in 15 mL of absolute ethanol at 0° C., and the reaction mixture was stirred at this temperature for 30 min. The mixture was neutralized by the addition of 2 N aq. NaOH and extracted with EtOAc (50 mL×3). The organic layers were combined and washed with 5% aq. NaHSO$_3$ and brine, dried (Na$_2$SO$_4$), and concentrated. The residue was purified by chromatography with hexane/EtOAc (4:1) to afford 5-bromo-4-(2-hydroxyethyl)-2-methoxypyridine (1.93 g, 91%). $^1$H NMR (CDCl$_3$) δ 8.14 (s, 1H), 6.68 (s, 1H), 3.86 (s, 3H), 3.85 (t, 2H, J=6.6 Hz), 3.13 (br s, 1H), 2.90 (t, 2H, J=6.6 Hz); $^{13}$C NMR (CDCl$_3$) δ 163.27, 149.24, 148.00, 114.41, 112.60, 60.56, 53.63, 38.34.

5-Bromo-6-(2-hydroxyethyl)-2-methoxypyridine: Yield, 88%. $^1$H NMR (CDCl$_3$) δ 7.66 (d, 1H, J=8.7 Hz), 6.53 (d, 1H, J=8.7 Hz), 4.05 (t, 2H, J=5.4 Hz), 3.90 (br s, 1H), 3.89 (s, 3H), 3.07 (t, 2H, J=5.4 Hz); $^{13}$C NMR (CDCl$_3$) δ 162.28, 155.41, 142.54, 111.90, 111.20, 60.61, 53.52, 37.71.

5-Bromo-4-[2-(ten-butyldimethylsilanyloxy)ethyl]-2-methoxypyridine: A mixture of 5-bromo-4-(2-hydroxyethyl)-2-methoxypyridine (2.33 g, 10 mmol), DMF (15 mL), imidazole (2.18 g, 32 mmol), DMAP (250 mg, 2 mmol), and TBDMSCl (2.44 g, 16 mmol) was stirred overnight at room temperature under nitrogen. After that the reaction mixture was diluted with ethyl acetate (150 mL), washed with brine, dried (Na$_2$SO$_4$), and concentrated. The residue was purified by chromatography with hexane/CH$_2$Cl$_2$/ether (10:1:1) to afford 5-bromo-4-[2-(tert-butyldimethylsilanyloxy)ethyl]-2-methoxypyridine as a colorless oil (3.40 g, 98%). $^1$H NMR (CDCl$_3$) δ 8.20 (s, 1H), 6.68 (s, 1H), 3.90 (s, 3H), 3.83 (t, 2H, J=6.6 Hz), 2.89 (t, 2H, J=6.6 Hz), 0.86 (s, 9H), −0.06 (s, 6H); $^{13}$C NMR (CDCl$_3$) δ 163.37, 149.47, 148.04, 114.55, 113.10, 61.41, 53.60, 38.71, 25.81, 18.20, −5.49.

3-Bromo-2-[2-(tert-butyldimethylsilanyloxy)ethyl]-6-methoxypyridine: Yield, 98%; colorless oil. $^1$H NMR (CDCl$_3$) δ 7.62 (d, 1H, J=8.7 Hz), 6.48 (d, 1H, J=8.7 Hz), 4.01

(t, 2H, J=7.2 Hz), 3.90 (s, 3H), 3.11 (t, 2H, J=7.2 Hz), 0.88 (s, 9H), 0.02 (s, 6H); $^{13}$C NMR (CDCl$_3$) δ 162.38, 154.66, 142.20, 112.15, 109.93, 61.88, 53.50, 40.24, 25.89, 18.28, −5.37.

7-tert-Butoxycarbonyl-2-exo-2-{4-[2-(tert-butyldimethylsilanyloxy)ethyl]-2-methoxy-5-pyridinyl}-7-azabicyclo[2.2.1]heptan-2-ol: To a stirred solution of 5-bromo-4-[2-(tert-butyldimethylsilanyloxy)ethyl]-2-methoxypyridine (385 mg, 1.1 mmol) in anhydrous THF (5 mL) at −78° C. under nitrogen was added dropwise 490 μL (1.22 mmol) of n-butyl lithium (2.5 M solution in hexanes). The reaction mixture was stirred at −78° C. for 1.5 h. The ketone 7-tert-butoxycarbonyl-7-azabicyclo[2.2.1]heptan-2-one (230 mg, 1.1 mmol) in THF (4 mL) was added dropwise and the mixture was stirred at −78° C. for another 1 h. After that it was slowly warmed to room temperature over a period of 1 h and stirred at room temperature for 0.5 h. The reaction was quenched by adding saturated aqueous NH$_4$Cl and extracted with EtOAc (3×20 mL). The combined organic layers were washed with brine, dried Na$_2$SO$_4$), and concentrated. The residue was purified by chromatography with hexane/EtOAc (6:1) to afford 7-tert-butoxycarbonyl-2-exo-2-{4-[2-(tert-butyldimethylsilanyloxy)ethyl]-2-methoxy-5-pyridinyl}-7-azabicyclo[2.2.1]heptan-2-ol as a colorless syrup (425 mg, 80%). $^1$H NMR (CDCl$_3$) δ 8.32 (s, 1H), 6.61 (s, 1H), 4.66 (s, 1H), 4.60 (s, 1H), 4.23 (br s, 1H), 4.07-3.99 (m, 1H), 3.93 (s, 3H), 3.84 (td, 1H, J=9.9, 3.9 Hz), 3.23 (ddd, 1H, J=13.5, 9.9, 5.1 Hz), 2.80 (dm, 1H, J=13.5 Hz), 2.60-2.48 (m, 1H), 2.32-2.18 (m, 1H), 1.85-1.60 (m, 4H), 1.45 (s, 9H), 0.74 (s, 9H), −0.08 (s, 3H), −0.13 (s, 3H); $^{13}$C NMR (CDCl$_3$) δ 163.39, 150.42, 143.89, 134.89, 111.59, 79.66, 64.85, 63.54, 58.10 and 57.10, 53.35, 48.73, 35.06, 29.68 and 29.09, 28.32, 25.64, 22.29 and 21.37, 18.21, −5.77, −5.92.

7-tert-Butoxycarbonyl-2-exo-2-{2-[2-(tert-butyldimethylsilanyloxy)ethyl]-6-methoxy-3-pyridinyl}-7-azabicyclo[2.2.1]heptan-2-ol: Yield, 86%; colorless syrup. $^1$H NMR (CDCl$_3$) δ 7.78 (d, 1H, J=8.7 Hz), 6.52 (d, 1H, J=8.7 Hz), 4.84 (s, 1H), 4.52 (br s, 1H), 4.20 (br s, 1H), 4.16-4.03 (m, 2H), 3.89 (s, 3H), 3.39 (m, 1H), 2.80 (br d, 1H, J=12.9 Hz), 2.54 (m, 1H), 2.27 (dd, 1H, J=12.3, 5.7 Hz), 1.86 (d, 1H, J=12.3 Hz), 1.84-1.62 (m, 3H), 1.44 (s, 9H), 0.71 (s, 9H), −0.12 (s, 3H), −0.17 (s, 3H); $^{13}$C NMR (CDCl$_3$) δ 162.24, 155.17, 136.03, 135.47, 106.74, 79.52, 78.08, 63.59, 63.34, 57.86 and 56.72, 53.19, 49.58 and 49.18, 38.04, 29.63 and 29.14, 28.32, 25.60, 22.25 and 21.45, 18.19, −5.83, −6.04; MS m/z (%): 479 (M$^+$, 4), 421 (6), 321 (8), 310 (11), 290 (10), 252 (18), 246 (11), 245 (28), 178 (100), 177 (41), 162 (23), 136 (33), 114 (88).

7-tert-Butoxycarbonyl-2-{4-[2-(tert-butyldimethylsilanyloxy)ethyl]-2-methoxy-5-pyridinyl}-7-azabicyclo[2.2.1]hept-2-ene: To a stirred solution of 7-tert-butoxycarbonyl-2-exo-2-{4-[2-(tert-butyldimethylsilanyloxy)ethyl]-2-methoxy-5-pyridinyl}-7-azabicyclo[2.2.1]heptan-2-ol (470 mg, 0.98 mmol), DMAP (40 mg, 0.33 mmol), Et$_3$N (800 μL, 5.74 mmol) in dry CH$_2$Cl$_2$ (8 mL) at 0° C. under N$_2$ was added dropwise methanesulfonyl chloride (270 μL, 3.5 mmol). After stirring at 0° C. for 1 h, the reaction mixture was warmed slowly to room temperature and stirred overnight. The reaction mixture was quenched by addition of saturated aq. NaHCO$_3$, and then diluted with EtOAc (60 mL). The organic layer was washed with brine, dried (Na$_2$SO$_4$), and concentrated. The residue was purified by chromatography with hexane/EtOAc (10:1) to afford 7-tert-butoxycarbonyl-2-{4-[2-(tert-butyldimethylsilanyloxy)ethyl]-2-methoxy-5-pyridinyl}-7-azabicyclo[2.2.1]hept-2-ene (380 mg, 84%) as a white solid, mp. 75-76° C. $^1$H NMR (CDCl$_3$) δ 7.92 (s, 1H), 6.67 (s, 1H), 6.24 (s, 1H), 4.88 (d, 1H, J=3.3 Hz), 4.79 (br s, 1H), 3.92 (s, 3H), 3.87-3.60 (m, 2H), 3.00-2.80 (m, 2H), 2.06-1.91 (m, 2H), 1.44 (s, 9H), 1.35-1.20 (m, 2H), 0.84 (s, 9H), −0.04 (s, 6H); $^{13}$C NMR (CDCl$_3$) δ 163.61, 155.19, 149.66, 145.71, 144.90 and 143.54, 132.57 and 131.47, 123.63, 111.48, 79.84, 63.20, 62.52, 60.82, 53.23, 35.90, 28.12, 25.72, 25.24, 24.40 and 23.56, 18.11, −5.61. MS m/z (%): 460 (M$^+$, 1), 347 (12), 319 (62), 275 (100), 201 (21). Anal. Calcd for (C$_{25}$H$_{40}$N$_2$O$_4$Si) C, 65.18; H, 8.75; N, 6.08. Found: C, 65.17; H, 8.84; N, 6.01.

7-tert-Butoxycarbonyl-2-{2-[2-(tert-butyldimethylsilanyloxy)ethyl]-6-methoxy-3-pyridinyl}-7-azabicyclo[2.2.1]hept-2-ene: Yield, 87%; syrup. $^1$H NMR (CDCl$_3$) δ 7.37 (br s, 1H), 6.54 (d, 1H, J=8.4 Hz), 6.26 (s, 1H), 4.89 (d, 1H, J=3.6 Hz), 4.78 (br s, 1H), 4.09-4.04 (m, 2H), 3.90 (s, 3H), 3.06-2.85 (m, 2H), 2.05-1.87 (m, 2H), 1.44 (s, 9H), 1.35-1.18 (m, 2H), 0.80 (s, 9H), −0.07 (s, 6H); $^{13}$C NMR (CDCl$_3$) δ 162.34, 155.37 and 154.88, 145.10, 138.70, 135.24, 132.00 and 130.71, 122.57, 116.22, 107.62, 79.86, 63.54, 62.74, 60.99, 53.14, 38.09, 28.18, 25.78, 25.17, 24.49 and 23.72, 18.20, −5.53. Anal. Calcd for (C$_{25}$H$_{40}$N$_2$O$_4$Si.3/4H$_2$O) C, 63.32; H, 8.82; N, 5.91. Found: C, 62.92; H, 8.30; N, 5.96.

7-ter-Butoxycarbonyl-2-[4-(2-hydroxyethyl)-2-methoxy-5-pyridinyl]-7-azabicyclo[2.2.1]hept-2-ene: To a stirred solution of 7-tert-butoxycarbonyl-2-{4-[2-(tert-butyldimethylsilanyloxy)ethyl]-2-methoxy-5-pyridinyl}-7-azabicyclo[2.2.1]hept-2-ene (360 mg, 0.78 mmol) in anhydrous THF (8 mL) was added 1.56 mL (1.56 mmol) of 1 M tetrabutylammonium fluoride in THF. The reaction solution was stirred at room temperature for 6 h, and then poured into a mixture of water (10 mL) and EtOAc (60 mL). The organic layer was separated and washed with brine, dried (Na$_2$SO$_4$), and concentrated. The residue was purified by chromatography with hexane/EtOAc (2:1) to afford 7-tert-butoxycarbonyl-2-[4-(2-hydroxyethyl)-2-methoxy-5-pyridinyl]-7-azabicyclo[2.2.1]hept-2-ene as a syrup (270 mg, 100%). $^1$H NMR (CDCl$_3$) δ 7.82 (s, 1H), 6.66 (s, 1H), 6.20 (s, 1H), 4.91 (s, 1H), 4.78 (s, 1H), 3.91 (s, 3H), 3.77 (br s, 2H), 3.20-2.85 (m, 2H), 2.40 (br s, 1H), 2.10-1.89 (m, 2H), 1.44 (s, 9H), 1.36-1.16 (m, 2H); $^{13}$C NMR (CDCl$_3$) δ 164.05, 156.36, 149.36, 145.98, 144.61, 132.12, 123.75, 111.27, 80.38, 62.92, 62.28, 61.45, 53.33, 36.88, 28.16, 25.83, 23.46. MS m/z (%): 346 (M$^+$, 1), 318 (8), 262 (100), 218 (12), 199 (21). Anal. Calcd for (C$_{19}$H$_{26}$N$_2$O$_4$.1/3H$_2$O) C, 64.75; H, 7.63; N, 7.95. Found: C, 64.55; H, 7.29; N, 7.64.

7-tert-Butoxycarbonyl-2-[2-2-hydroxyethyl)-6-methoxy-3-pyridinyl]-7-azabicyclo[2.2.1]hept-2-ene: Yield, 100%; syrup. $^1$H NMR (CDCl$_3$) δ 7.42 (d, 1H, J=8.4 Hz), 6.64 (d, 1H, J=8.4 Hz), 6.18 (s, 1H), 4.84 (s, 1H), 4.81 (s, 1H), 4.48 (br s, 1H), 4.10-3.95 (m, 2H), 3.92 (s, 3H), 3.11-2.92 (m, 2H), 2.08-1.92 (m, 2H), 1.44 (s, 9H), 1.34-1.18 (m, 2H); $^{13}$C NMR (CDCl$_3$) δ 162.34, 156.06, 139.07, 132.62, 131.42, 122.00, 108.38, 80.18, 63.23, 61.45, 53.48, 36.30, 28.20, 25.32 and 24.65 and 23.84. MS m/z (%): 346 (M$^+$, 1), 318 (26), 262 (100), 232 (61), 188 (24). Anal. Calcd for (C$_{19}$H$_{26}$N$_2$O$_4$.1/2H$_2$O) C, 64.21; H, 7.66; N, 7.88. Found: C, 64.55; H, 7.48; N, 7.84.

7-tert-Butoxycarbonyl-2-[4-(2-bromoethyl)-2-methoxy-5-pyridinyl]-7-azabicyclo[2.2.1]hept-2-ene: To a stirred solution of 7-tert-butoxycarbonyl-2-[4-(2-hydroxyethyl)-2-methoxy-5-pyridinyl]-7-azabicyclo[2.2.1]hept-2-ene (390 mg, 1.13 mmol) in dry CH$_2$Cl$_2$ (20 mL) under N$_2$ was added CBr$_4$ (745 mg, 2.25 mmol). The mixture was stirred at room temperature for 10 min, and then a solution of PPh$_3$ (590 mg, 2.25 mmol) in dry CH$_2$Cl$_2$ (5 mL) was slowly added. After that the reaction mixture was stirred at room temperature for 2 h and quenched by water, and then diluted with CH$_2$Cl$_2$. The organic layer was separated and washed with brine, dried (Na$_2$SO$_4$), and concentrated. The residue was purified by chromatography with hexane/EtOAc (6:1) to afford 7-tert-butoxycarbonyl-2-[4-(2-bromoethyl)-2-methoxy-5-pyridinyl]-7-azabicyclo[2.2.1]hept-2-ene as a syrup (400 mg, 87%). $^1$H NMR (CDCl$_3$) δ 7.95 (br s, 1H), 6.66 (s, 1H), 6.23 (br s, 1H), 4.86 (d, 1H, J=3.6 Hz), 4.81 (br s, 1H), 3.94 (s, 3H), 3.59-3.46 (m, 2H), 3.42-3.12 (m, 2H), 2.09-1.92 (m, 2H), 1.45 (s, 9H), 1.36-1.20 (m, 2H); $^{13}$C NMR (CDCl$_3$) δ 163.83, 155.35, 148.55, 146.16, 144.63, 132.04, 123.16, 111.15, 80.16, 63.16, 61.35, 53.44, 35.97, 30.76, 28.20, 25.96 and 25.32, 24.55 and 23.62.

7-tert-Butoxycarbonyl-2-[2-(2-bromoethyl)-6-methoxy-3-pyridinyl]-7-azabicyclo[2.2.1]hept-2-ene: Yield, 88%; syrup. $^1$H NMR (CDCl$_3$) δ 7.42 (d, 1H, J=8.4 Hz), 6.62 (d, 1H, J=8.4 Hz), 6.20 (s, 1H), 4.85 (s, 1H), 4.81 (s, 1H), 3.93 (s, 3H), 3.88 (t, 2H, J=7.2 Hz), 3.43-3.25 (m, 2H), 2.08-1.92 (m, 2H), 1.45 (s, 9H), 1.36-1.21 (m, 2H); $^{13}$C NMR (CDCl$_3$) δ 162.50, 155.37, 153.47, 145.38, 138.80, 132.28 and 131.11, 122.07, 108.44, 80.13, 63.41, 61.25, 53.39, 37.90, 30.96, 28.23, 25.82 and 25.22, 24.55 and 23.82.

Radical cyclization of 7-tert-butoxycarbonyl-2-[4-(2-bromoethyl-2-methoxy-5-pyridinyl]-7-azabicyclo[2.2.1]hept-2-ene: To a stirred solution of 7-tert-butoxycarbonyl-2-[4-(2-bromoethyl)-2-methoxy-5-pyridinyl]-7-azabicyclo[2.2.1]hept-2-ene (390 mg, 0.95 mmol) in toluene (25 mL) was added AIBN (50 mg) and tributyltin hydride (512 µL, 1.90 mmol). The reaction mixture was refluxed overnight at 120° C. under N$_2$. After cooling to room temperature, the solvent was removed in vacuo. The residue was purified by chromatography with hexane/ether (3:1) to afford fused cyclized product: 105 mg (33%), white solid, mp. 130-131° C.; $^1$H NMR (CDCl$_3$) δ 8.06 (s, 1H), 6.43 (s, 1H), 4.28 (d, 1H, J=3.3 Hz), 4.08 (br s, 1H), 3.90 (s, 3H), 2.88 (d, 1H, J=8.4 Hz), 2.78-2.68 (m, 1H), 2.41-2.31 (m, 1H), 2.28-2.19 (m, 1H), 1.94-1.52 (m, 6H), 1.48-1.12 (m, 9H); $^{13}$C No (CDCl$_3$) δ 162.24, 151.27, 146.77, 126.93, 108.54, 79.27, 63.68, 62.40, 60.86, 53.25, 43.34, 29.32, 28.10, 27.35, 26.18. MS m/z (%): 330 (M$^+$, 6), 229 (29), 163 (27), 162 (100). Anal. Calcd for (C$_{19}$H$_{26}$N$_2$O$_3$) C, 69.06; H, 7.93; N, 8.48. Found: C, 69.35; H, 8.03; N, 8.31. And the spiro cyclized product: 170 mg (54%), white solid, mp. 82-83° C.; $^1$H NMR (CDCl$_3$) δ 7.88 (s, 1H), 6.60 (s, 1H), 4.30 (br s, 1H), 3.91 (s, 3H), 3.90 (br s, 1H), 2.86 (ddd, 1H, J=16.5, 11.4, 6.9 Hz), 2.72 (dd, 1H, J=16.5, 8.1 Hz), 2.49 (br s, 1H), 2.01-1.51 (m, 7H), 1.47 (s, 9H); $^{13}$C NMR (CDCl$_3$) δ 163.43, 158.07, 141.61, 134.96, 106.37, 79.53, 61.71, 57.17 and 56.33, 53.48, 45.48, 42.92, 30.07, 29.52, 28.34, 24.42 and 23.81. MS m/z (%): 330 (M$^+$, 6), 274 (20), 229 (22), 162 (100), 160 (17), 114 (12). Anal. Calcd for (C$_{19}$H$_{26}$NO$_3$) C, 69.06; H, 7.93; N, 8.48. Found: C, 69.34; H, 7.72; N, 8.26.

General preparation of N-trifluoroacetyl fused epibatidine analogue A: To a stirred solution of the fused radical reaction product A (40 mg, 0.12 mmol) in dry CH$_2$Cl$_2$ (3 mL) was added trifluoroacetic acid (200 µL). The reaction mixture was stirred at room temperature under N$_2$ for 4 h. After that saturated aq. Na$_2$CO$_3$ was added and the mixture was diluted with CH$_2$Cl$_2$ (20 mL). The organic layer was separated and washed with brine, dried (Na$_2$SO$_4$), and concentrated. The residue (30 mg) was used without purification for the following reaction.

The above crude residue (30 mg) was dissolved in 1 mL of CH$_2$Cl$_2$ and 100 µL of pyridine was added. To the stirred mixture was added dropwise trifluoroacetic anhydride (34 µL, 0.24 mmol). The reaction mixture was stirred at room temperature under N$_2$ for 2 h. After that the mixture was diluted with CH$_2$Cl$_2$ (20 mL), washed with saturated aq. NaHCO$_3$ and brine, dried (Na$_2$SO$_4$), and concentrated. The residue was purified by chromatography with hexane/EtOAc (6:1) to afford a syrup (25 mg). $^1$H NMR (CDCl$_3$) δ (rotamers) 8.10 and 8.03 (s, 1H), 6.43 (s, 1H), 4.85 (d, J=3.9 Hz) and 4.52 (d, J=3.9 Hz) (1H), 4.44 (s) and 4.28 (s) (1H), 3.89 (s, 3H), 3.15 (d, J=8.4 Hz) and 2.99 (d, J=8.7 Hz) (1H), 2.68-2.52 (m, 2H), 2.50-2.34 (m, 2H), 2.06-1.46 (m, 6H); $^{13}$C NMR (CDCl$_3$) δ (rotamers) 162.62 and 162.53, 150.28 and 150.18, 146.95 and 146.78, 125.10 and 124.94, 118.18 and 117.99, 114.35 and 114.15, 108.84 and 108.80, 65.42 and 65.39, 62.90 and 62.87, 62.55, 60.70, 53.26, 43.91, 43.77, 41.45, 41.34, 29.94, 29.59, 28.56, 28.13, 27.05, 26.28, 25.72, 25.66; $^{19}$F NMR (CDCl$_3$) δ (rotamers) 5.44 (s) and 5.33 (s). MS m/z (%): 326 (M$^+$, 19), 187 (100), 165 (16), 162 (20). Anal. Calcd for (C$_{16}$H$_{17}$F$_3$N$_2$O$_2$) C, 58.89; H, 5.25; N, 8.58. Found: C, 59.14; H, 5.15; N, 8.38.

To a stirred solution of above product (25 mg) in DMF (0.4 mL) at 0° C. under N$_2$ was added POCl$_3$ (50 µL) dropwise. After stirring for 1 h the reaction mixture was heated to 95° C. for 10 h, then cooled to 0° C. Saturated aq. NaOAc was added cautiously and the mixture was diluted with EtOAc (20 mL). The organic layer was washed with saturated aq. NaHCO$_3$ and brine, dried (Na$_2$SO$_4$), and concentrated. The residue was purified by chromatography with hexane/EtOAc (6:1) to afford N-trifluoroacetyl fused epibatidine analogue A (16 mg, 65%). $^1$H NMR (CDCl$_3$) δ (rotamers) 8.33 and 8.26 (s, 1H), 7.05 (s, 1H), 4.86 (d, J=4.2 Hz) and 4.55 (d, J=4.2 Hz) (1H), 4.46 (d, J=3.9 Hz) and 4.31 (s) (1H), 3.19 (d, J=8.7 Hz) and 3.02 (d, J=8.7 Hz) (1H), 2.74-2.56 (m, 1H), 2.53-2.40 (m, 2H), 2.10-1.52 (m, 6H); $^{13}$C NMR (CDCl$_3$) δ (rotamers) 150.83 and 150.58, 149.93 and 149.86, 149.13, 131.19, 123.26 and 123.16, 117.91, 114.09, 65.16 and 65.14, 62.88, 62.47, 60.69, 43.59, 43.65, 41.53, 41.26, 29.96, 29.76, 28.63, 28.30, 26.74, 26.04, 25.38, 25.32; 19F NMR (CDCl$_3$) δ (rotamers) 5.37 (s) and 5.27 (s).

N-Trifluoroacetyl fused epibatidine analogue B: $^1$H NMR (CDCl$_3$) δ (rotamers) 7.59 (d, J=8.1 Hz) and 7.51 (d, J=8.1 Hz) (1H), 7.19 (d, 1H, J=8.1 Hz), 4.86 (d, J=4.5 Hz) and 4.57 (d, J=4.5 Hz) (1H), 4.45 (d, J=3.9 Hz) and 4.32 (m) (1H), 3.14 (d, J=8.7 Hz) and 2.99 (d, J=9.0 Hz) (1H), 2.95-2.76 (m, 1H), 2.71-2.56 (m, 1H), 2.51-2.38 (m, 1H), 2.14-1.52 (m, 6H); $^{13}$C NMR (CDCl$_3$) δ (rotamers) 159.47 and 159.34, 148.51 and 148.42, 139.07 and 139.00, 129.74 and 129.67, 122.45 and 122.25, 118.12 and 117.98, 114.29 and 114.15, 64.60 and 64.57, 62.82 and 62.78, 61.79, 60.58, 46.10, 43.95, 43.58, 41.67, 30.20, 29.96, 29.86, 29.55, 28.38, 28.22, 25.94; $^{19}$F NMR (CDCl$_3$) δ (rotamers) 5.5 (s) and 5.4 (s).

N-Trifluoroacetyl spiro epibatidine analogue A: White solid, mp. 117-118° C. $^1$H NMR (CDCl$_3$) δ (rotamers) 8.16 and 8.14 (s, 1H), 7.24 (s, 1H), 4.88 (t, J=4.5 Hz) and 4.65 (s) (1H), 4.50 (d, J=4.2 Hz) and 4.19 (m) (1H), 3.05-2.79 (m, 2H), 2.43-2.36 (m, 1H), 2.16-1.62 (m, 7H); $^{13}$C NMR (CDCl$_3$) δ (rotamers) 158.35 and 158.07, 150.38 and 150.32, 144.98 and 144.75, 139.37 and 139.30, 120.79 and 120.75, 118.37, 114.54, 62.62 and 62.58, 60.88, 58.18 and 58.14, 56.00, 55.58, 54.40, 45.46, 43.32, 42.34, 42.25, 30.10, 29.88, 28.22, 25.10, 23.10; $^{19}$F NMR (CDCl$_3$) δ (rotamers) 5.77 (s) and 4.88 (s). MS m/z (%): 332 ([M+2]$^+$, 9), 330 (M$^+$, 27), 233 (16), 191 (37), 166 (100), 165 (67), 164 (42). Anal. Calcd for (C$_{15}$H$_{14}$ClF$_3$N$_2$O) C, 54.47; H, 4.27; N, 8.47. Found: C, 54.30; H, 4.29; N, 8.33.

N-Trifluoroacetyl spiro epibatidine analogue B: $^1$H NMR (CDCl$_3$) δ (rotamers) 7.40 (d, J=7.8 Hz) and 7.38 (d, J=7.8 Hz) (1H), 7.19 (d, 1H, J=7.8 Hz), 4.87 (t, J=4.8 Hz) and 4.64 (m) (1H), 4.52 (d, J=3.6 Hz) and 4.22 (m) (1H), 3.19-2.99 (m, 1H), 2.97-2.87 (m, 1H), 2.45-2.36 (m, 1H), 2.13-1.82 (m, 4H), 1.77-1.60 (m, 3H); $^{19}$F NMR (CDCl$_3$) δ (rotamers) 5.8 (s) and 4.9 (s).

General procedure for removal of the N-trifluoroacetyl group: To a stirred solution of N-trifluoroacetyl fused epibatidine analogue A (14 mg, 42 µmol) in MeOH (1 mL) was added 0.5 mL of NaOMe (30% solution in MeOH). The reaction mixture was stirred at room temperature for 12 h. After that it was neutralized to pH 8.0 with 1 M HCl and diluted with EtOAc (20 mL). The organic layer was washed with saturated aq. NaHCO$_3$ and brine, dried (Na$_2$SO$_4$), and concentrated. The residue was purified by chromatography with CH$_2$Cl$_2$/CH$_3$OH (2:1) to afford fused epibatidine analogue A (8.5 mg, 85%). $^1$H NMR (CDCl$_3$) δ 8.28 (s, 1H), 7.03 (s, 1H), 3.76 (d, 1H, J=4.5 Hz), 3.41 (d, 1H, J=3.9 Hz), 2.81 (d, 1H, J=8.7 Hz), 2.79 (ddd, 1H, J=15.9, 7.5, 3.9 Hz), 2.42 (ddd, 1H, J=15.9, 9.0, 3.9 Hz), 2.20 (td, 1H, J=8.1. 6.6 Hz), 1.93-1.81 (m, 1H), 1.79-1.44 (m, 6H); $^{13}$C NMR (CDCl$_3$) δ 151.78, 149.64, 148.10, 134.00, 122.91, 64.66, 62.26, 43.42, 42.70, 30.48, 30.13, 27.62, 26.33. MS m/z (%): 236 ([M+2]$^+$, 4), 234 (M$^+$, 12), 168 (34), 167 (21), 166 (100), 128 (14). Anal. Calcd for (C$_{13}$H$_{15}$ClN$_2$. 1/4H$_2$O) C, 65.27; H, 6.53; N, 11.71. Found: C, 65.39; H, 6.33; 11.36.

Fused epibatidine analogue B: Yield, 87%. $^1$H NMR (CDCl$_3$) δ 7.54 (d, 1H, J=8.1 Hz), 7.16 (d, 1H, J=8.1 Hz), 3.71 (d, 1H, J=3.9 Hz), 3.42 (d, 1H, J=3.9 Hz), 2.95 (ddd, 1H, J=16.2, 6.9, 3.9 Hz), 2.80 (d, 1H, J=8.7 Hz), 2.61 (ddd, 1H, J=16.2, 9.6, 4.2 Hz), 2.20 (td, 1H, J=8.7, 6.3 Hz), 2.00 (dtd, 1H, J=13.2, 6.6, 4.2 Hz), 1.78-1.47 (m, 6H); $^{13}$C NMR (CDCl$_3$) δ 160.26, 147.49, 138.91, 132.51, 121.97, 64.18, 62.15, 45.68, 43.04, 30.86, 30.10, 30.00, 26.91. MS m/z (%): 236 ([M+2]$^+$, 6), 234 (M$^+$, 17), 168 (34), 167 (25), 166 (100), 128 (15). Anal. Calcd for (C$_{13}$H$_{15}$ClN$_2$. 1/5H$_2$O) C, 65.51; H, 6.51; N, 11.75. Found: C, 65.63; H, 6.30; N, 11.41.

Spiro epibatidine analogue A: $^1$H NMR (CDCl$_3$) δ 8.08 (s, 1H), 7.17 (s, 1H), 3.77 (t, 1H, J=4.2 Hz), 3.34 (d, 1H, J=4.5 Hz), 2.90 (ddd, 1H, J=16.8, 11.7, 7.2 Hz), 2.78 (dd, 1H, J=16.8, 8.7 Hz), 2.72 (s, 1H), 2.41 (dd, 1H, J=12.9, 7.2 Hz), 1.94-1.70 (m, 4H), 1.64-1.37 (m, 3H); $^{13}$C NMR (CDCl$_3$) δ 157.88, 149.21, 144.83, 141.99, 120.22, 62.88, 57.19, 46.56, 43.36, 30.22, 29.68, 25.02. MS m/z (%): 236 ([M+2]$^+$, 2), 234 (M$^+$, 6), 168 (33), 167 (12), 166 (100), 128 (8). Anal. Calcd for (C$_{13}$H$_{15}$ClN$_2$. 1/5H$_2$O) C, 65.51; H, 6.51; N, 11.75. Found: C, 65.58; H, 6.44; N, 11.12.

Spiro epibatidine analogue B: $^1$H NMR (CDCl$_3$) δ 7.33 (d, 1H, J=8.1 Hz), 7.13 (d, 1H, J=8.1 Hz), 3.74 (t, 1H, J=4.5 Hz), 3.35 (d, 1H, J=3.9 Hz), 3.04 (ddd, 1H, J=17.1, 11.7, 7.5 Hz), 2.87 (dd, 1H, J=17.1, 8.7 Hz), 2.39 (dd, 1H, J=12.9, 7.5 Hz), 1.95-1.70 (m, 5H), 1.54-1.29 (m, 3H); $^{13}$C NMR (CDCl$_3$) δ 166.68, 149.55, 139.19, 134.08, 121.10, 63.08, 57.20, 47.30, 41.63, 32.24, 29.77, 24.93. MS m/z (%): 236 ([M+2]$^+$, 3), 234 (M$^+$, 9), 168 (33), 167 (14), 166 (100), 128 (16). Anal. Calcd for (C$_{13}$H$_{15}$ClN$_2$. 1/4H$_2$O) C, 65.27; H, 6.53; N, 11.71. Found: C, 65.57; H, 6.29; 10.84.

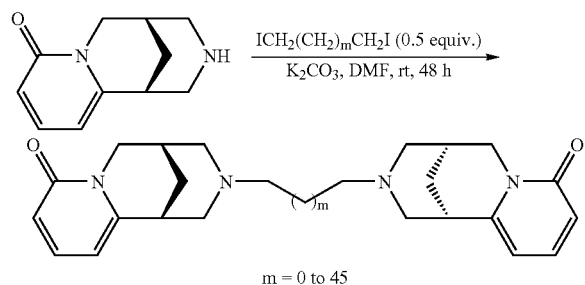

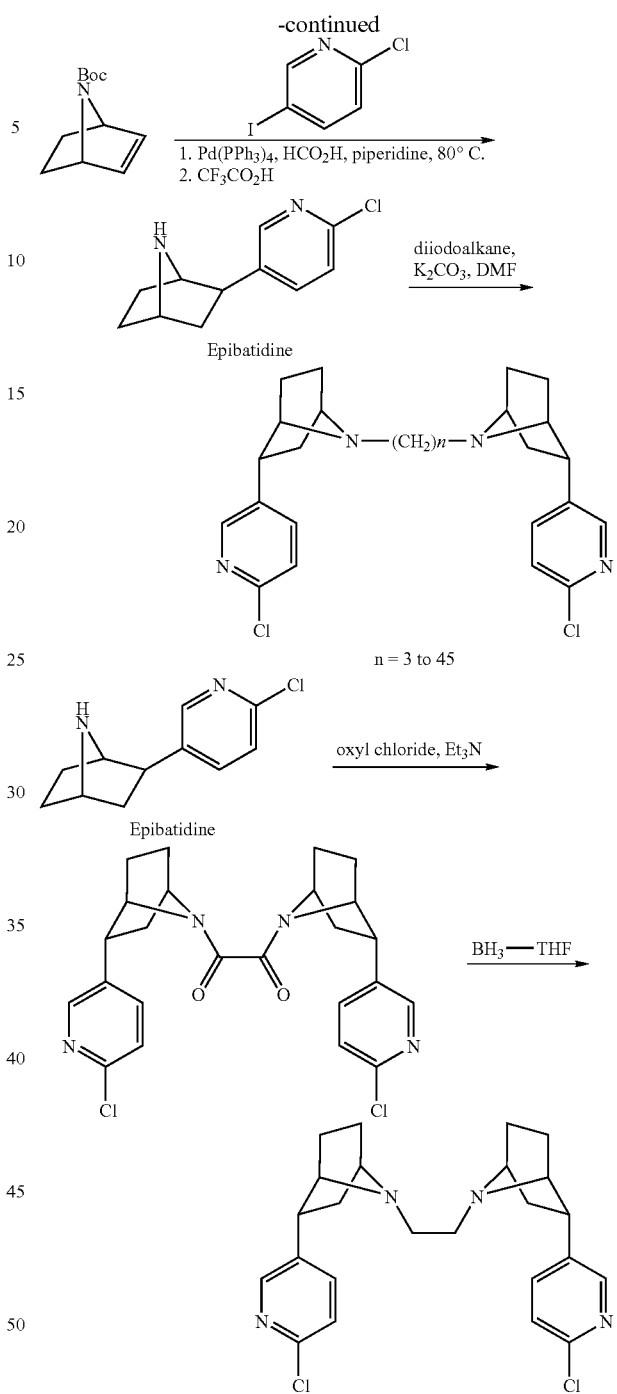

2-exo-(2-Chloro-5-pyridyl)-7-azabicyclo[2.2.1]heptane (Epibatidine): To a stirred mixture of 7-azabicyclo[2.2.1]hept-2-ene (515 mg, 2.63 mmol), 2-chloro-5-iodopyridine (1.90 g, 7.9 mmol), Pd(PPh$_3$)$_4$ (456 mg, 0.4 mmol) in DMF (5 mL) at room temperature under argon was added piperidine (0.91 mL, 9.2 mmol) and formic acid (0.3 mL, 7.9 mmol). The reaction mixture was stirred at 75° C. for 48 h. The solvent was removed in vacuo and the residue was dissolved in EtOAc (150 mL), washed with brine, dried over Na$_2$SO$_4$, and concentrated. The resulting residue was purified by chromatography with hexane-EtOAc (4:1) to give a syrup (770 mg, 95%). $^1$H NMR (CDCl$_3$) δ 8.25 (d, 1H, J=2.1 Hz), 7.64 (dd, 1H, J=8.4, 2.1 Hz), 7.25 (d, 1H, J=8.4 Hz), 4.38 (br s, 1H), 4.16 (br s, 1H), 2.87 (dd, 1H, J=9.0, 4.8 Hz), 2.00 (dd, 1H, J=12.6, 9.0 Hz), 1.95-1.75 (m, 3H), 1.65-1.50 (m, 2H), 1.44 (s, 9H).

To a solution of the above product (770 mg, 2.5 mmol) in CH$_2$Cl$_2$ (5 mL) was added dropwise with stirring under N$_2$ trifluoroacetic acid (2 mL). The reaction mixture was stirred at room temperature for 3 h and then rendered basic with saturated aq. K$_2$CO$_3$. The mixture was diluted with CH$_2$Cl$_2$ (50 mL) and the organic phase was washed with brine, dried over Na$_2$SO$_4$, and concentrated. The residue was purified by chromatography with CH$_2$Cl$_2$/MeOH (5:1) to give a solid. $^1$H NMR (CDCl$_3$) δ 8.28 (d, 1H, J=2.4 Hz), 7.77 (dd, 1H, J=8.4, 2.4 Hz), 7.23 (d, 1H, J=8.4 Hz), 3.80 (m, 1H), 3.56 (s, 1H), 2.77 (dd, 1H, J=9.0, 5.1 Hz), 1.97-1.78 (m, 2H), 1.68-1.46 (m, 5H); $^{13}$C NMR (CDCl$_3$) δ 148.90, 148.76, 141.16, 137.65, 123.89, 62.72, 56.36, 44.48, 40.33, 31.35, 30.14.

Ethane-1,3-N,N'-bisepibatidine: To a stirred solution of epibatidine (100 mg, 0.5 mmol) in CH$_2$Cl$_2$ (5 mL) and Et$_3$N (0.1 mL) at 0° C. was added dropwise oxyl chloride (0.25 mmol). The reaction mixture was stirred at room temperature overnight. The mixture was diluted with CH$_2$Cl$_2$ (50 mL) and the organic phase was washed with brine, dried over Na$_2$SO$_4$, and concentrated. The residue was purified by chromatography to give a solid (200 mg, 85%).

To a solution of the above product (100 mg, 0.21 mmol) in THF (5 mL) was added borane (1.0 M solution in THF, 1 mL). The reaction mixture was stirred at room temperature for 24 h and quenched with water. The mixture was diluted with CH$_2$Cl$_2$ (50 mL) and the organic phase was washed with brine, dried over Na$_2$SO$_4$, and concentrated. The residue was purified by chromatography with CH$_2$Cl$_2$/MeOH (2:1) to give a solid. $^1$H NMR (CDCl$_3$) δ 8.36 (m, 1H), 7.89-7.80 (m, 1H), 7.18-7.12 (m, 1H), 3.42 (m, 1H), 3.21 (m, 1H), 2.63 (dd, 1H, J=9.0, 5.1 Hz), 2.59-2.40 (m, 3H), 1.95-1.78 (m, 3H), 1.72-1.58 (m, 1H); 1.50-1.36 (m, 2H); $^{13}$C NMR (CDCl$_3$) δ 148.97, 148.76, 141.85, 138.17, 123.63, 65.95, 60.00, 47.59, 45.18, 41.30, 26.87, 26.13.

General procedure for the preparation of the dimers: A mixture of epibatidine or cytisine (50 μmol), diiodide (25 μmol), K$_2$CO$_3$ (5 mg), and DMF (0.3 mL) was stirred at room temperature for 48 h. The solvent was removed in vacuo, and the residue was filtered and purified by PLC.

Propane-1,3-N,N'-biscytisine: $^1$H NMR (CDCl$_3$) δ 7.26 (dd, 2H, J=9.0, 6.9 Hz), 6.42 (dd, 2H, J=9.0, 1.5 Hz), 5.90 (dd, 2H, J=6.9, 1.5 Hz), 4.00 (d, 2H, J=15.3 Hz), 3.82 (dd, 2H, J=15.3, 6.6 Hz), 2.87-2.72 (m, 4H), 2.55-2.48 (m, 2H), 2.42-2.33 (m, 2H), 2.17-2.10 (m, 4H), 1.96-1.67 (m, 8H), 1.27-1.17 (m, 2H); $^{13}$C NMR (CDCl$_3$) δ 163.50, 151.94, 138.39, 116.27, 104.40, 60.33, 59.97, 53.56, 50.17, 35.59, 27.98, 25.86, 23.73.

Hexane-1,3-N,N'-biscytisine: $^1$H NMR (CDCl$_3$) δ 7.23 (dd, 2H, J=9.0, 6.9 Hz), 6.38 (d, 2H, J=9.0 Hz), 5.96 (d, 2H, J=6.9 Hz), 4.02 (d, 2H, J=15.3 Hz), 3.86 (dd, 211, J=15.3, 6.6 Hz), 2.92-2.81 (m, 6H), 2.40 (m, 2H), 2.25-2.04 (m, 8H), 1.89-1.73 (m, 4H), 1.14 (m, 4H), 0.91 (m, 4H); $^{13}$C NMR (CDCl$_3$) δ 163.56, 151.86, 138.52, 116.34, 104.37, 60.24, 60.22, 57.28, 50.09, 35.57, 28.06, 26.47, 26.36, 26.03.

Octane-1,3-N,N'-biscytisine: $^1$H NMR (CDCl$_3$) δ 7.23 (dd, 2H, J=9.0, 6.9 Hz), 6.39 (dd, 2H, J=9.0, 1.5 Hz), 5.96 (dd, 2H, J=6.9, 1.5 Hz), 4.02 (d, 2H, J=15.3 Hz), 3.87 (dd, 2H, J=15.3, 6.6 Hz), 2.96-2.82 (m, 6H), 2.40 (m, 2H), 2.28-2.13 (m, 8H), 1.92-1.73 (m, 4H), 1.30-0.90 (m, 12H).

Propane-1,3-N,N'-bisepibatidine: $^1$H NMR (CDCl$_3$) δ 8.35 and 8.34 (d, 2H, J=2.7 Hz), 7.88 and 7.84 (dd, 2H, J=8.1, 2.7 Hz), 7.19 and 7.15 (d, 2H, J=8.1 Hz), 3.42 and 3.39 (t, 2H, J=4.2 Hz), 3.18 and 3.15 (d, 2H, J=3.9 Hz), 2.65 and 2.62 (dd, 2H, J=5.1, 3.0 Hz), 2.51-2.33 (m, 4H), 1.92-1.35 (m, 14H); $^{13}$C NMR (CDCl$_3$) δ 149.01 and 148.99, 148.75 and 148.73, 141.97 and 141.89, 138.21 and 138.16, 123.57 and 123.53, 65.75 and 65.74, 59.33 and 59.26, 45.24 and 45.22 and 45.20, 41.26, 29.56 and 29.47, 26.79 and 26.77, 26.00 and 25.99.

Hexane-1,3-N,N'-bisepibatidine: $^1$H NMR (CDCl$_3$) δ 8.35 (d, 2H, J=1.8 Hz), 7.90 (dt, 2H, J=8.4, 2.7 Hz), 7.20 (d, 2H, J=8.4 Hz), 3.40 (m, 2H), 3.18 (t, 2H, J=3.6 Hz), 2.62 (dd, 2H, J=9.0, 4.5 Hz), 2.42-2.24 (m, 4H), 1.92-1.78 (m, 6H), 1.65 (m, 2H), 1.52-1.30 (m, 12H); $^{13}$C NMR (CDCl$_3$) δ 148.98, 148.69, 142.11, 138.26, 123.62, 65.53 and 65.48, 59.35, 47.18 and 47.14, 45.19, 41.44, 29.66 and 29.64, 27.58 and 27.55, 26.77, 26.04.

Decane-1,3-N,N'-bisepibatidine: $^1$H NMR (CDCl$_3$) δ 8.33 (d, 2H, J=2.7 Hz), 7.93 (dd, 2H, J=8.4, 2.7 Hz), 7.20 (d, 2H, J=8.4 Hz), 3.40 (t, 2H, J=3.9 Hz), 3.18 (d, 2H, J=3.0 Hz), 2.62 (dd, 2H, J=9.0, 4.8 Hz), 2.42-2.24 (m, 4H), 1.92-1.78 (m, 6H), 1.62 (m, 2H), 1.52-1.20 (m, 20H); $^{13}$C NMR (CDCl$_3$) δ 148.94, 148.69, 142.13, 138.26, 123.66, 65.47, 59.35, 47.22, 45.14, 41.46, 29.64, 29.56, 27.66, 26.76, 26.03.

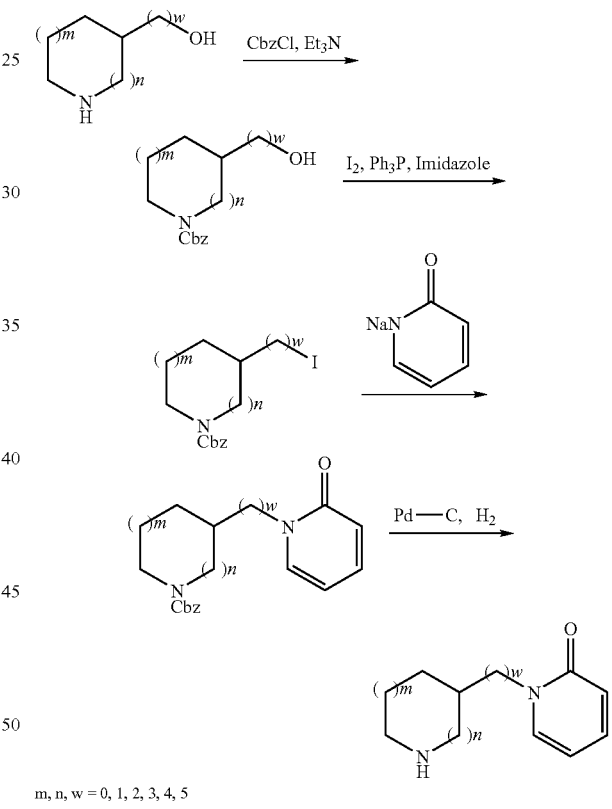

m, n, w = 0, 1, 2, 3, 4, 5

3-Hydroxymethylpiperidine-1-carboxylic acid benzyl ester: To a stirred solution of 3-hydroxymethylpiperidine (1 g, 8.7 mmol) in CH$_2$Cl$_2$ (50 mL) and Et$_3$N (1.12 mml) at 0° C. was added dropwise CbzCl (1.24 mL, 8.7 mmol). The reaction mixture was stirred at room temperature overnight. The mixture was washed with brine, dried over Na$_2$SO$_4$, and concentrated. The residue was purified by chromatography with hexane-EtOAc (2:1) to give a colorless oil (2 g, 94%). $^1$H NMR (CDCl$_3$) δ 7.35 (m, 5H), 5.12 (m, 2H), 4.20-3.60 (m, 2H), 3.47 (m, 2H), 3.20-2.20 (m, 3H), 1.82-1.10 (m, 5H); $^{13}$C NMR (CDCl$_3$) δ 155.55, 136.73, 128.38, 127.85, 127.69, 66.96, 64.31, 46.74, 44.71, 38.01, 26.77, 24.05.

3-Iodomethylpiperidine-1-carboxylic acid benzyl ester: To a stirred solution of PPh$_3$ (3.5 g) in dry CH$_2$Cl$_2$ (60 mL) was added 12 (3.34 g) under N$_2$. After stirred for 15 min, imidazole (1.03 g) was added in one portion, followed by addition of 3-hydroxymethylpiperidine-1-carboxylic acid benzyl ester (1.5 g, 6.02 mmol) in CH$_2$Cl$_2$ (5 mL). The reaction mixture was stirred at room temperature for 4 h, washed with 5% aqueous NaHSO$_3$ and brine, dried, and concentrated. The residue was purified by chromatography with hexane-EtOAc (4:1) to give a viscous oil (2.1 g, 97%). $^1$H NMR (CDCl$_3$) δ 7.35 (m, 5H), 5.13 (s, 2H), 4.15 (br s, 1H), 3.96 (dt, 1H, J=13.2, 3.9 Hz), 3.07 (d, 2H, J=6.3 Hz), 2.85 (m, 1H), 2.66 (br s, 1H), 1.94 (m, 1H), 1.74-1.38 (m, 3H), 1.33-1.17 (m, 1H); $^{13}$C NMR (CDCl$_3$) δ 155.10, 136.71, 128.40, 127.89, 127.75, 67.02, 49.71, 44.31, 37.90, 31.21, 24.18, 9.52.

3-(2-Oxo-2H-pyridin-1-ylmethyl)piperidine-1-carboxylic acid benzyl ester: To a stirred solution of 2-hydroxypyridine (200 mg, 2 mmol) in DMF (5 mL) was added NaH (60% mixture in mineral oil, 100 mg, 2.5 mmol). The mixture was stirred at 80° C. under N$_2$ for 2 h, and then 3-iodomethylpiperidine-1-carboxylic acid benzyl ester (720 mg, 2 mmol) was added. The mixture was stirred at 80° C. for 10 h, cooled to room temperature, quenched with water, and extracted with EtOAc. The combined organic layers were washed with brine, dried, and concentrated. The residue was purified by chromatography with CH$_2$Cl$_2$-EtOAc-MeOH (10:10:1) to give a viscous oil (475 mg, 73%). $^1$H NMR (CDCl$_3$) δ 7.30 (m, 7H), 6.55 (d, 1H, J=9.0 Hz), 6.12 (m, 1H), 5.11 (s, 2H), 4.10-3.50 (m, 4H), 3.09 (t, 1H, J=10.2 Hz), 2.92 (dd, 1H, J=13.2, 9.0 Hz), 2.10 (m, 1H), 1.85-1.20 (m, 4H).

1-Piperidin-3-ylmethyl-1H-pyridin-2-one: A mixture of 3-(2-oxo-2H-pyridin-1-ylmethyl)piperidine-1-carboxylic acid benzyl ester (100 mg) and 5% Pd—C (20 mg) in EtOH (15 mL) was stirred under H$_2$ (1 atm). The reaction was traced by TLC. The catalyst was filtered and the filtration was concentrated and purified by chromatography with CH$_2$Cl$_2$-MeOH—NH$_3$.H$_2$O (10:1:0.1) to give a syrup (50 mg, 85%). $^1$H NMR (CDCl$_3$) δ 7.31 (m, 1H), 7.21 (dd, 1H, J=6.9, 2.1 Hz), 6.56 (d, 1H, J=9.0 Hz), 6.14 (td, 1H, J=6.6, 1.5 Hz), 3.90 (dd, 1H, J=13.0, 8.1 Hz) 3.76 (dd, 1H, J=13.0, 6.7 Hz), 2.98 (m, 2H), 2.62 (t, 1H, J=9.8 Hz), 2.44 (t, 1H, J=11.2 Hz), 2.10-1.10 (m, 6H).

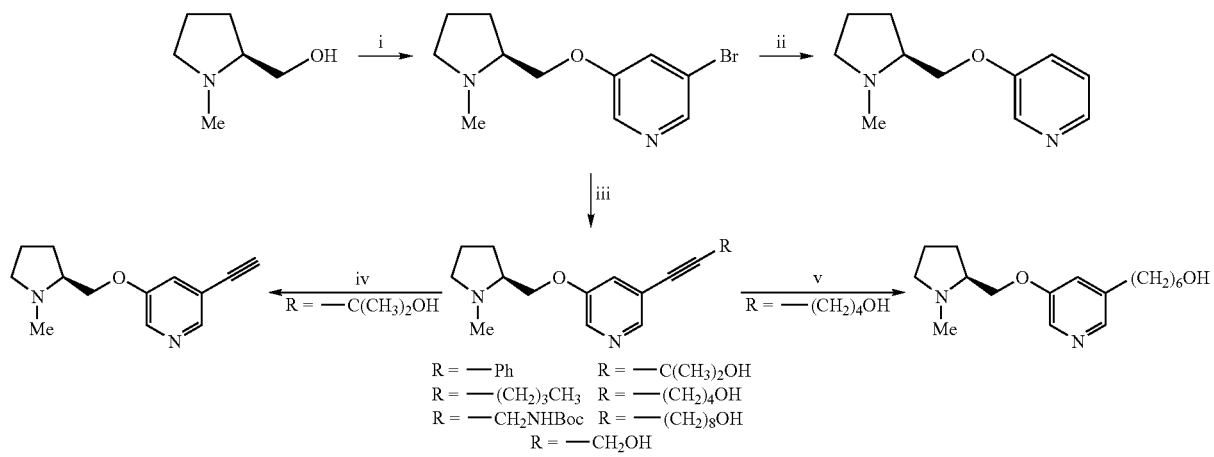

Reagents: (i) NaH, DMF, then 3,5-dibromopyridine, room temperature, 70%; (ii) 10% Pd—C, EtOH, H$_2$ (1 atm), 99%; (iii) Alkyne, 10% Pd—C (cat.), CuI (cat.), K$_2$CO$_3$, DME, H$_2$O, reflux, 72 h, 55-95%; (iv) NaH (cat.), toluene, 120° C., 1 h, 99%; (v) 10% Pd—C, EtOAc, H$_2$ (1 atm), 99%.

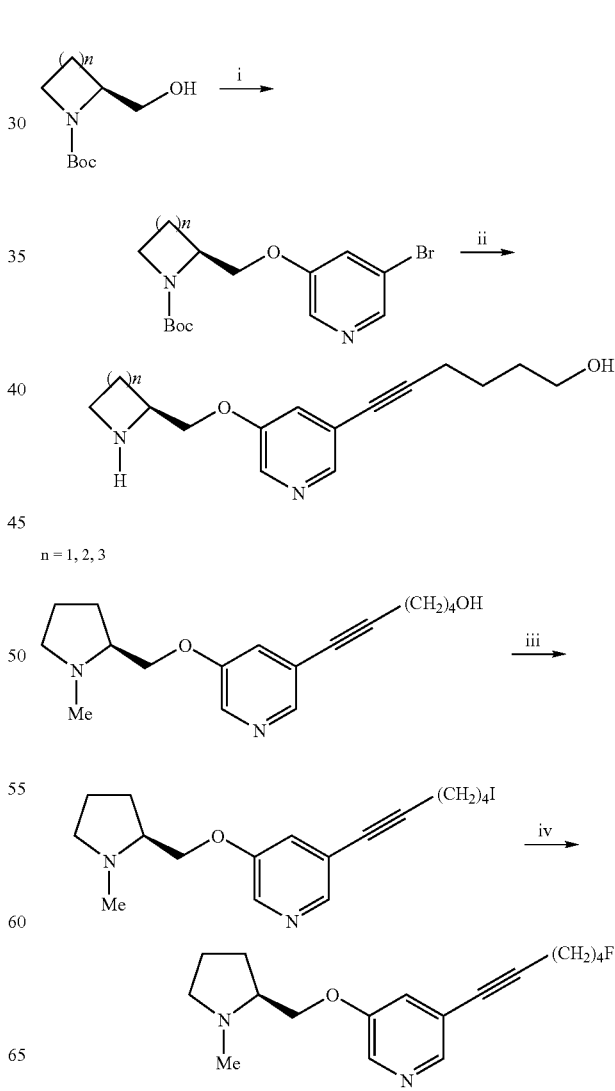

n = 1, 2, 3

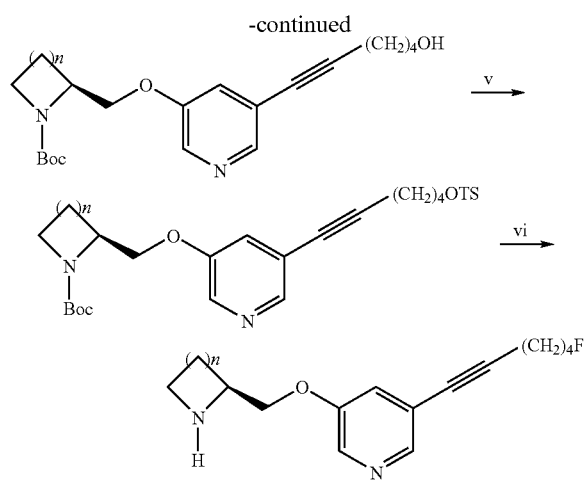

n = 1, 2, 3
Reagents: (i) 3-Brom-5-hydroxypyridine, PPh₃, DEAD, THF, room temperature.
(ii) a) 5-Hexyn-1-ol, 10% Pd—C (cat.), CuI (cat.), K₂CO₃, DME, H₂O, reflux, 72 h;
b) CF₃CO₂H, CH₂Cl₂. (iii) I₂, PPh₃, imidazole, CH₂Cl₂. (iv) AgF, acetonitrile, room temperature, 10 h. (v) p-TsCl, Et₃N, DMAP (cat.), CH₂Cl₂;
(vi) a) Tetrabutylammonium fluoride (1M in THF), room temperature, 10-15 h;
b) CF₃CO₂H, CH₂Cl₂.

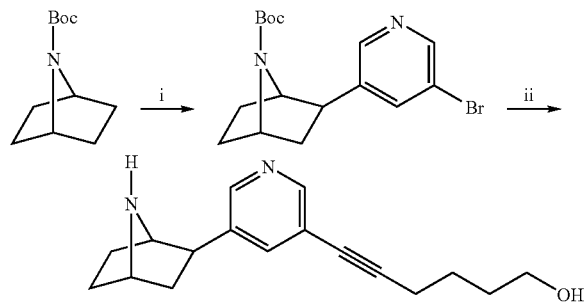

Reagents: (i) 3,5-Dibromopyridine, Pd(PPh₃)₄ (cat.), piperidine, HCO₂H, DMF, 80° C., 72 h. (ii) a) 6-[(tert-Butyldimethylsilyl)oxy]-1-hexyne, Pd(PPh₃)₂Cl₂, CuI, Bu₄NI, Et₃N, DMF, reflux, 48 h; b) CF₃CO₂H, CH₂Cl₂.

5-Bromo-3-(1-methyl-2(S)-pyrrolidinylmethoxy)pyridine: To a stirred solution of (S)-1-methyl-2-pyrrolidinylmethanol (2.3 g, 20 mmol) in anhydrous DMF (100 mL) was added in small portions NaH (60% in mineral oil, 880 mg, 22 mmol). The mixture was stirred at room temperature for 2 h, then 3,5-dibromopyridine (5.2 g, 22 mmol) was added. The reaction mixture was stirred at room temperature for 48 h, poured into ice-cold water (200 mL), and extracted with EtOAc (100 in L×3). The organic layers were combined, washed with brine, dried over anhydrous Na2SO4, filtered and concentrated. The residue was purified by chromatography with C H₂Cl₂-MeOH (5:1) to give a brown oil (3.8 g, 70%). [α]$_D$–42.4 (c 1.8, CHCl₃). ¹H NMR (CDCl₃) δ 8.28 (d, 1H, J=2.1 Hz), 8.25 (d, 1H, J=2.7 Hz), 7.38 (t, 1H, J=2.4 Hz), 4.00 (dd, 1H, J=9.3, 5.4 Hz), 3.93 (dd, 1H, J=9.3, 5.4 Hz), 3.16-3.08 (m, 1H), 2.72-2.63 (m, 1H), 2.48 (s, 3H), 2.32 (td, 1H, J=9.3, 7.2 Hz), 2.10-1.97 (m, 1H), 1.92-1.66 (m, 3H); ¹³C NMR (CDCl₃) δ 155.29, 142.72, 136.27, 123.77, 120.15, 71.36, 63.95, 57.66, 41.69, 28.52, 23.10.

3-(1-Methyl-2(S)-pyrrolidinylmethoxy)pyridine: A mixture of 5-bromo-3-(1-methyl-2(S)-pyrrolidinylmethoxy)pyridine (100 mg, 0.37 mmol), 10% Pd—C (15 mg), and EtOH (5 mL) was stirred under H₂ (1 atm) at room temperature for 8 h. The reaction mixture was filtered through Celite and washed with MeOH. The filtrate was concentrated and the residue was treated with EtOAc (30 mL) and saturated aqueous Na₂CO₃ solution (5 mL). The organic layer was separated, washed with brine, dried over anhydrous Na₂SO₄, filtered and concentrated. The residue was purified by chromatography with CH₂Cl₂-MeOH (5:1) to give an oil (70 mg, 99%). [α]$_D$–68.8 (c 2.4, CHCl₃). ¹H NMR (CDCl₃) δ 8.31 (t, 1H, J=1.5 Hz), 8.20 (t, 1H, J=3.0 Hz), 7.20-7.17 (m, 2H), 4.00 (dd, 1H, J=9.3, 5.4 Hz), 3.91 (dd, 1H, J=9.3, 5.4 Hz), 3.15-3.07 (m, 1H), 2.70-2.61 (m, 1H), 2.47 (s, 3H), 2.30 (td, 1H, J=9.3, 7.2 Hz), 2.09-1.96 (m, 1H), 1.92-1.66 (m, 3H); ¹³C NMR (CDCl₃) δ 155.09, 142.01, 137.99, 123.68, 120.91, 70.94, 64.09, 57.66, 41.63, 28.51, 22.96.

General procedure for the Pd—C catalyzed Sonogashira reaction in aqueous system. 5-(3-Hydroxy-1-propargyl)-3-(1-methyl-2(S)-pyrrolidinylmethoxy)pyridine: To a stirred solution of 5-bromo-3-(1-methyl-2(S)-pyrrolidinylmethoxy)pyridine (270 mg, 1.0 mmol), K₂CO₃ (345 mg, 2.5 mmol), PPh₃ (30 mg, 0.11 mmol) in DME (2 mL) and H₂O (2 mL) was added 10% Pd/C (30 mg) and CuI (30 mg, 0.16 mmol). The mixture was stirred at room temperature for 30 min under argon, and then propargyl alcohol (145 μL, 2.5 mmol) was added. The reaction mixture was refluxed for 72 h. After cooled, the mixture was filtered through Celite and washed with EtOAc. The filtrate was concentrated in vacuo. The residue was purified by chromatography with CH₂Cl₂-MeOH (5:1) to give an oil (230 mg, 93%). [α]$_D$–40 (c 1.82, CHCl₃). ¹H NMR (CDCl₃) δ 8.30 (d, 1H, J=1.5 Hz), 8.23 (d, 1H, J=2.7 Hz), 7.21 (dd, 1H, J=2.7, 1.5 Hz), 4.70 (br s, 1H), 4.46 (s, 2H), 4.01 (dd, 1H, J=9.3, 5.4 Hz), 3.93 (dd, 1H, J=9.3, 5.4 Hz), 3.17-3.10 (m, 1H), 2.74-2.65 (m, 1H), 2.49 (s, 3H), 2.33 (td, 1H, J=9.3, 7.2 Hz), 2.11-1.98 (m, 1H), 1.94-1.65 (m, 3H); ¹³C NMR (CDCl₃) δ 154.34, 144.26, 137.49, 123.03, 120.07, 91.76, 81.32, 71.04, 64.14, 57.71, 50.81, 41.78, 28.51, 22.99. Anal. Calcd for C₁₄H₁₈N₂O₂.0.1H₂O: C, 67.77; H, 7.39; N, 11.29. Found: C, 67.56; H, 7.22; N, 11.22.

5-(2-Phenyl-1-ethynyl)-3-(1-methyl-2(S)-pyrrolidinylmethoxy)pyridine: Yield, 74%; [α]$_D$–15.4 (c 0.44, CHCl₃). ¹H NMR (CDCl₃) δ 8.37 (d, 1H, J=1.5 Hz), 8.28 (d, 1H, J=2.7 Hz), 7.58-7.51 (m, 2H), 7.40-7.34 (m, 3H), 7.33 (dd, 1H, J=2.7, 1.5 Hz), 4.05 (dd, 1H, J=9.3, 5.4 Hz), 3.97 (dd, 1H, J=9.3, 5.4 Hz), 3.17-3.11 (m, 1H), 2.76-2.66 (m, 1H), 2.50 (s, 3H), 2.34 (td, 1H, J=9.3, 7.5 Hz), 2.12-1.99 (m, 1H), 1.95-1.68 (m, 3H); ¹³C NMR (CDCl₃) δ 154.50, 144.59, 137.72, 131.69, 128.80, 128.44, 122.94, 122.48, 120.54, 92.35, 85.84, 71.14, 64.15, 57.73, 41.71, 28.52, 23.04.

5-(1-Hexynyl)-3-(1-methyl-2(S)-pyrrolidinylmethoxy)pyridine: Yield, 55%; [α]$_D$–51.5 (c 1.0, CHCl₃). ¹H NMR (CDCl₃) δ 8.22 (d, 1H, J=1.5 Hz), 8.20 (d, 1H, J=3.0 Hz), 7.19 (dd, 1H, J=3.0, 1.5 Hz), 3.98 (dd, 1H, J=9.3, 5.4 Hz), 3.91 (dd, 1H, J=9.3, 5.4 Hz), 3.15-3.08 (m, 1H), 2.70-2.61 (m, 1H), 2.47 (s, 3H), 2.42 (t, 2H, J=6.9 Hz), 2.31 (td, 1H, J=9.3, 7.5 Hz), 2.09-1.96 (m, 1H), 1.92-1.41 (m, 7H), 0.96 (t, 3H, J=7.2 Hz); ¹³C NMR (CDCl₃) δ 154.46, 144.63, 136.93, 123.09, 121.24, 93.80, 77.21, 71.14, 64.05, 57.72, 41.69, 30.57, 28.53, 23.03, 21.97, 19.09, 13.59. Purified by HPLC. Waters μBondapak™ C18 column (7.8×300 mm), 10% CH₃CN in water containing 0.05% CF₃CO₂H to 40% CH₃CN in water containing 0.05% CF₃CO₂H; flow rate 2.8 mL/min; t=19 min.

5-(3-tert-Butoxycarbonylamino-1-propynyl)-3-(1-methyl-2(S)-pyrrolidinylmethoxy)pyridine: Yield, 75%; [α]$_D$–39.4 (c 1.70, CHCl₃). ¹H NMR (CDCl₃) δ 8.24 (s, 2H), 7.21 (dd, 1H, J=2.7, 1.8 Hz), 5.13 (br s, 1H), 4.16 (d, 2H, J=5.4 Hz), 3.98 (dd, 1H, J=9.3, 5.4 Hz), 3.91 (dd, 1H, J=9.3, 5.4 Hz), 3.15-3.08 (m, 1H), 2.71-2.61 (m, 1H), 2.47 (s, 3H), 2.31 (td, 1H, J=9.3, 7.5 Hz), 2.10-1.96 (m, 1H), 1.93-1.65 (m, 3H), 1.47 (s, 9H); ¹³C NMR (CDCl₃) δ 155.29, 154.40, 144.53, 137.74, 123.09, 119.90, 88.76, 80.03, 79.53, 71.16, 63.97, 57.66, 41.65, 31.02, 28.45, 28.30, 22.97.

5-(3-Hydroxy-3-methyl-1-butynyl)-3-(1-methyl-2(S)pyrrolidinylmethoxy)pyridine: Yield, 95%; $[\alpha]_D$ –41.3 (c 1.60, CHCl$_3$). $^1$H NMR (CDCl$_3$) δ 8.30 (d, 1H, J=1.5 Hz), 8.22 (d, 1H, J=3.0 Hz), 7.20 (dd, 1H, J=3.0, 1.5 Hz), 4.00 (dd, 1H, J=9.3, 5.4 Hz), 3.95 (br s, 1H), 3.92 (dd, 1H, J=9.3, 5.4 Hz), 3.16-3.09 (m, 1H), 2.72-2.62 (m, 1H), 2.48 (s, 3H), 2.32 (td, 1H, J=9.3, 7.5 Hz), 2.10-1.97 (m, 1H), 1.93-1.65 (m, 3H), 1.61 (s, 6H); $^{13}$C NMR (CDCl$_3$) δ 154.48, 144.33, 137.48, 123.10, 120.18, 97.71, 78.34, 71.17, 64.96, 64.07, 57.69, 41.73, 31.35, 28.48, 22.94. Anal. Calcd for C$_{16}$H$_{22}$N$_2$O$_2$.0.1H$_2$O: C, 69.59; H, 8.10; N, 10.14. Found: C, 69.38; H, 7.75; N, 10.13.

5-(6-Hydroxy-1-hexynyl)-3-(1-methyl-2(S)-pyrrolidinylmethoxy)pyridine: Yield, 91%; $[\alpha]_D$ –35.5 (c 0.81, CHCl$_3$). $^1$H NMR (CDCl$_3$) δ 8.19 (d, 1H, J=1.5 Hz), 8.18 (d, 1H, J=152.7 Hz), 7.18 (dd, 1H, J=2.7, 1.5 Hz), 3.97 (dd, 1H, J=9.3, 5.4 Hz), 3.90 (dd, 1H, J=9.3, 5.4 Hz), 3.68 (t, 2H, J=6.3 Hz), 3.13-3.06 (m, 1H), 2.69-2.61 (m, 1H), 2.60 (br s, 1H), 2.46 (s, 3H), 2.44 (t, 2H, J=6.6 Hz), 2.29 (td, 1H, J=9.3, 7.5 Hz), 2.08-1.95 (m, 1H), 1.91-1.62 (m, 7H); $^{13}$C NMR (CDCl$_3$) δ 154.41, 144.43, 136.84, 123.10, 121.11, 93.40, 77.42, 71.04, 64.01, 61.97, 57.64, 41.65, 31.81, 28.43, 24.80, 22.91, 19.15.

5-(10-Hydroxy-1-decynyl)-3-(1-methyl-2(S)-pyrrolidinylmethoxy)pyridine: Yield, 84%; $[\alpha]_D$ –25.1 (c 0.74, CHCl$_3$). $^1$H NMR (CDCl$_3$) δ 8.22 (d, 1H, J=1.5 Hz), 8.20 (d, 1H, J=3.0 Hz), 7.19 (dd, 1H, J=3.0, 1.5 Hz), 4.03 (dd, 1H, J=9.3, 5.4 Hz), 3.92 (dd, 1H, J=9.3, 5.4 Hz), 3.63 (t, 2H, J=6.6 Hz), 3.17-3.11 (m, 1H), 2.75-2.65 (m, 1H), 2.49 (s, 3H), 2.42 (t, 2H, J=6.9 Hz), 2.34 (td, 1H, J=9.3, 7.5 Hz), 2.20 (br s, 1H), 2.11-1.98 (m, 1H), 1.94-1.30 (m, 15H); $^{13}$C NMR (CDCl$_3$) δ 154.40, 144.59, 137.02, 123.03, 121.25, 93.87, 77.31, 70.88, 64.22, 62.82, 57.64, 41.64, 32.72, 29.22, 28.96, 28.63, 28.53, 28.33, 25.67, 22.96, 19.35.

5-(1-Ethynyl)-3-(1-methyl-2(S)-pyrrolidinylmethoxy)pyridine: To a stirred solution of 5-(3-hydroxy-3-methyl-1-butynyl)-3-(1-methyl-2(S) -pyrrolidinylmethoxy)pyridine (70 mg, 0.25 mmol) in toluene (3 mL) was added NaH (60% in mineral oil, 2 mg, 0.05 mmol). The reaction mixture was refluxed for 1 h, and then some toluene was distilled. After cooled, the mixture was treated with ice-cold water, and extracted with EtOAc (15 mL×3). The combined organic layers were washed with brine, dried over anhydrous Na$_2$SO$_4$, filtered and concentrated. The residue was purified by chromatography with CH$_2$Cl$_2$-MeOH (5:1) to give a light yellow oil (55 mg, 99%), $[\alpha]_D$ –59 (c 1.4, CHCl$_3$). $^1$H NMR (CDCl$_3$) δ 8.32 (d, 1H, J=1.5 Hz), 8.29 (d, 1H, J=2.7 Hz), 7.28 (dd, 1H, J=2.7, 1.5 Hz), 4.01 (dd, 1H, J=9.3, 5.4 Hz), 3.93 (dd, 1H, J=9.3, 5.4 Hz), 3.20 (s, 1H), 3.16-3.09 (m, 1H), 2.73-2.63 (m, 1H), 2.48 (s, 3H), 2.32 (td, 1H, J=9.3, 7.2 Hz), 2.10-1.97 (m, 1H), 1.94-1.67 (m, 3H); $^{13}$C NMR (CDCl$_3$) δ 154.38, 145.01, 138.27, 123.50, 119.26, 80.27, 71.12, 64.03, 57.67, 41.65, 28.47, 23.01.

5-(6-Hydroxy-1-hexanyl)-3-(1-methyl-2(S)-pyrrolidinylmethoxy)pyridine: A mixture of 5-(6-hydroxy-1-hexynyl)-3-(1-methyl-2(S)-pyrrolidinylmethoxy)pyridine (50 mg, 0.17 mmol), 10% Pd—C (10 mg), and EtOAc (5 mL) was stirred under H$_2$ (1 atm) at room temperature for 3 h. The reaction mixture was filtered through Celite and washed with MeOH. The filtrate was concentrated to provide an oil (50 mg, 99%), $[\alpha]_D$ –31 (c 1.6, CHCl$_3$). $^1$H NMR (CDCl$_3$) δ 8.12 (d, 1H, J=2.4 Hz), 8.03 (d, 1H, J=1.5 Hz), 7.03 (t, 1H, J=2.1 Hz), 4.02 (dd, 1H, J=9.3, 5.4 Hz), 3.92 (dd, 1H, J=9.3, 5.4 Hz), 3.62 (t, 2H, J=6.6 Hz), 3.16-3.09 (m, 1H), 2.72-2.63 (m, 1H), 2.58 (t, 2H, J=7.5 Hz), 2.48 (s, 3H), 2.50 (br s, 1H), 2.31 (td, 1H, J=9.3, 7.5 Hz), 2.10-1.97 (m, 1H), 1.93-1.28 (m, 11H); $^{13}$C NMR (CDCl$_3$) δ 155.02, 142.17, 138.54, 134.89, 121.29, 70.93, 64.13, 62.48, 57.67, 41.67, 32.64, 32.58, 30.86, 28.79, 28.48, 25.48, 22.94.

5-Bromo-3-(1-tert-butoxycarbonyl-2(S)-azetidinylmethoxy)pyridine: To a stirred solution of 1-tert-butoxycarbonyl-2(S)-azetidine (800 mg, 4.3 mmol) and 3-bromo-5-hydroxypyridine (800 mg, 4.6 mmol), and PPh$_3$ (1.69 g, 6.45 mmol) in THF (50 mL) was slowly added DEAD (1.02 mL, 6.45 mmol). The reaction mixture was stirred at room temperature for 48 h, and concentrated in vacuo. The residue was purified by chromatography with hexane-EtOAc (4:1) to give a light yellow oil (1.25 g, 85%). $^1$H NMR (CDCl$_3$) δ 8.29 (d, 1H, J=2.1 Hz), 8.28 (d, 1H, J=2.7 Hz), 7.43 (t, 1H, J=2.4 Hz), 4.51 (m, 1H), 4.34 (m, 1H), 4.13 (dd, 1H, J=10.2, 3.0 Hz), 3.89 (t, 2H, J=7.5 Hz), 2.42-2.22 (m, 2H), 1.43 (s, 9H); $^{13}$C NMR (CDCl$_3$) δ 156.05, 155.35, 143.07, 136.58, 123.96, 120.25, 79.75, 68.90, 59.84, 47.02, 28.31, 18.88.

5-Bromo-3-(1-tert-butoxycarbonyl-2(S)-pyrrolidinylmethoxy)pyridine: To a stirred solution of 1-tert-butoxycarbonyl-2(S)-pyrrolidine (2 g, 10 mmol) and 3-bromo-5-hydroxypyridine (1.57 g, 9.0 mmol), and PPh$_3$ (3.4 g, 13 mmol) in THF (100 mL) was slowly added DEAD (2.05 mL, 13 mmol). The reaction mixture was stirred at room temperature for 20 b, and concentrated in vacuo. The residue was purified by chromatography with hexane-EtOAc (5:1) to give a syrup (2.6 g, 81%), $[\alpha]_D$=–52.7 (c 1.1, CHCl$_3$). $^1$H NMR (CDCl$_3$) δ 8.27 (s, 1H), 8.25 (d, 1H, J=2.4 Hz), 7.41 (m, 1H), 4.20-4.38 (m, 3H), 3.50-3.20 (m, 2H), 2.10-1.80 (m, 4H), 1.47 (s, 9H); $^{13}$C NMR (CDCl$_3$) δ 155.37, 154.70 and 154.56, 143.12 and 142.87, 136.74 and 136.39, 123.86, 120.35, 80.01 and 79.64, 69.00 and 68.71, 55.87 and 55.58, 46.96 and 46.61, 28.50, 28.04, 23.85 and 22.84.

5-(6-Hydroxy-1-hexynyl)-3-(1-tert-butoxycarbonyl-2(S)-azetidinylmethoxy)pyridine: To a stirred solution of 5-bromo-3-(1-tert-butoxycarbonyl-2(S)-azetidinylmethoxy)pyridine (720 mg, 2.1 mmol), K$_2$CO$_3$ (725 mg, 5.25 mmol), PPh$_3$ (50 mg) in DME (5 mL) and H$_2$O (5 mL) was added 10% Pd/C (50 mg) and CuI (50 mg). The mixture was stirred at room temperature for 30 min under argon, then 5-hexyn-1-ol (0.8 mL) was added. The reaction mixture was refluxed for 72 h. After cooled, the mixture was filtered through Celite and washed with EtOAc. The filtrate was concentrated in vacuo. The residue was purified by chromatography with hexane-EtOAc (1:2) and then EtOAc to give an oil (630 mg, 83%), $[\alpha]_D$–37.1 (c 1.9, CHCl$_3$). $^1$H NMR (CDCl$_3$) δ 8.22 (d, 2H, J=2.1 Hz), 7.24 (t, 1H, J=2.1 Hz), 4.50 (m, 1H), 4.32 (m, 1M), 4.11 (dd, 1H, J=10.2, 3.0 Hz), 3.88 (t, 2H, J=7.5 Hz), 3.75-3.65 (m, 2H), 2.47 (t, 2H, J=6.9 Hz), 2.41-2.20 (m, 2H), 1.95 (s, 1H), 1.80-1.64 (m, 4H), 1.42 (s, 9H); $^{13}$C NMR (CDCl$_3$) δ 156.13, 154.40, 144.75, 137.13, 123.26, 121.18, 93.48, 79.76, 77.45, 68.68, 62.20, 60.00, 47.06, 31.82, 28.36, 24.80, 19.18, 19.01.

5-(6-Hydroxy-1-hexynyl)-3-(1-tert-butoxycarbonyl-2(S)-pyrrolidinylmethoxy)pyridine: To a stirred solution of 5-bromo-3-(1-tert-butoxycarbonyl-2(S)-pyrrolidinylmethoxy)pyridine (800 mg, 2.24 mmol), K$_2$CO$_3$ (745 mg, 5.40 mmol), PPh$_3$ (55 mg) in DME (4 mL) and H$_2$O (4 mL) was added 10% Pd/C (55 mg) and CuI (55 mg). The mixture was stirred at room temperature for 30 ml under argon, then 5-hexyn-1-ol (1.0 mL) was added. The reaction mixture was refluxed for 72 h. After cooled, the mixture was filtered through Celite and washed with EtOAc. The filtrate was concentrated in vacuo. The residue was purified by chromatography with hexane-EtOAc (1:1) to give an oil (800 mg, 95%), $[\alpha]_D$=–35.5 (c 2.2, CHCl$_3$). $^1$H NMR (CDCl$_3$) δ 8.19 (m, 2H), 7.23 (m, 1H), 4.14 (m, 2H), 4.05-3.75 (m, 1H), 3.75-3.69 (m, 2H), 3.50-3.25 (m, 2H), 2.47 (t, 2H, J=6.6 Hz), 2.10-1.64 (m, 9H), 1.47 (s, 9H); $^{13}$C NMR (CDCl$_3$) δ 154.70, 154.36, 144.76 and 144.49, 137.29 and 137.00, 123.04, 121.15, 93.32, 79.96 and 79.56, 68.69 and 68.33, 62.28, 55.94 and 55.64, 46.97 46.59, 31.82, 28.51, 28.00, 24.79, 23.84, 22.83, 19.20.

5-(6-Hydroxy-1-hexynyl)-3-(2(S)-azetidinylmethoxy)pyridine: HPLC: Waters μBondapak™ C$_{18}$ column (7.8×300 mm), 10% CH$_3$CN in water containing 0.05% CF$_3$CO$_2$H to 40% CH$_3$CN in water containing 0.05% CF$_3$CO$_2$H; flow rate 2.8 mL/min; t=18.1 min. [α]$_D$ −56.6 (c 1.0, CHCl$_3$). $^1$H NMR (CDCl$_3$) δ 8.26 (br s, 2H), 7.23 (s, 1H), 4.84 (m, 1H), 4.59 (dd, 1H, J=10.2, 3.6 Hz), 4.48-4.30 (m, 2H), 4.13 (dd, 1H, J=10.2, 2.4 Hz), 3.72 (t, 2H, J=6.3 Hz), 2.75-2.35 (m, 4H), 1.85-1.65 (m, 6H); $^{13}$C NMR (CDCl$_3$) δ 156.94, 145.19, 136.98, 123.33, 121.54, 93.80, 77.33, 66.25, 62.29, 60.81, 50.41, 31.82, 24.76, 19.35, 19.20.

5-(6-Hydroxy-1-hexynyl)-3-(2(S)-pyrrolidinylmethoxy)pyridine: To a stirred solution of 5-(6-hydroxy-1-hexynyl)-3-(1-tert-butoxycarbonyl-2(S)-pyrrolidinylmethoxy)pyridine (25 mg) in dry CH$_2$Cl$_2$ (1.0 mL) was added CF$_3$CO$_2$H (2.0 mL). The mixture was stirred at room temperature for 2 h. Saturated aq. K$_2$CO$_3$ was added, and the mixture was extracted with CH$_2$Cl$_2$ (30 mL×3). The organic layers were combined, washed with brine, dried over Na$_2$SO$_4$, and concentrated. The residue was purified by chromatography with CH$_2$Cl$_2$-MeOH (10:1 to 3:1) and then CH$_2$Cl$_2$-MeOH-Et$_3$N (3:1:0.1) to give a light yellow oil (85%), [α]$_D$ +6.4 (c 2.1, CHCl$_3$). $^1$H NMR (CDCl$_3$) δ 8.21 (d, 1H, J=1.8 Hz), 8.19 (d, 1H, J=2.7 Hz), 7.19 (dd, 1H, J=2.7, 1.8 Hz), 3.98 (dd, 1H, J=9.3, 5.1 Hz), 3.92 (dd, 1H, J=9.0, 6.9 Hz), 3.71 (t, 2H, J=6.3 Hz), 3.57 (m, 1H), 3.11-2.96 (m, 2H), 2.61 (br s, 2H), 2.47 (t, 2H, J=6.9 Hz), 2.05-1.53 (m, 8H); $^{13}$C NMR (CDCl$_3$) δ 154.28, 144.68, 136.96, 123.20, 121.17, 93.47, 77.50, 71.09, 62.21, 57.11, 46.38, 31.84, 27.76, 25.12, 24.80, 19.20. HPLC. Waters μBondapak™ C$_{18}$ column (7.8×300 mm), 10% CH$_3$CN in water containing 0.05% CF$_3$CO$_2$H to 40% CH$_3$CN in water containing 0.05% CF$_3$CO$_2$H; flow rate 2.8 mL/min; t=18.5 min.

7-tert-Butoxycarbonyl-2-exo-(5-bromo-3-pyridyl)-7-azabicyclo[2.2.1]heptane: To a stirred mixture of 7-tert-butoxycarbonyl-7-azabicyclo[2.2.1]hept-2-ene (100 mg, 0.5 mmol), 3,5-dibromopyridine (1.0 g, 4.2 mmol), Pd(PPh$_3$)$_4$ (50 mg, 44 μmol) in DMF (2 mL) under argon was added piperidine (150 μL, 1.5 mmol) and formic acid (48 μL, 1.25 mmol). The reaction mixture was stirred at 80° C. for 72 h. The solvent was removed in vacuo and the residue was dissolved in EtOAc (100 mL), washed with brine, dried over Na$_2$SO$_4$, and concentrated. The resulting residue was purified by chromatography with n-hexane-EtOAc (5:1) to give a brown solid (110 mg, 61%). $^1$H NMR (CDCl$_3$) δ $^1$H NMR (CDCl$_3$) δ 8.51 (d, 1H, J=2.1 Hz), 8.40 (d, 1H, J=1.8 Hz), 7.81 (t, 1H, J=2.1 Hz), 4.40 (br s, 1H), 4.20 (s, 1H), 2.87 (dd, 1H, J=8.7, 5.1 Hz), 2.00 (dd, 1H, J=12.3, 9.0 Hz), 1.94-1.73 (m, 3H), 1.65-1.47 (m, 2H), 1.45 (s, 9H); $^{13}$C NMR (CDCl$_3$) δ 154.90, 148.76, 147.15, 142.84, 136.88, 120.87, 79.97, 61.69, 55.81, 45.27, 40.19, 29.69, 28.75, 28.28.

7-tert-Butoxycarbonyl-2-exo-(5-(6-tert-butyl(dimethyl)silyloxy-1-hexynyl)-3-pyridyl)-7-azabicyclo[2.2.1]heptane: To a stirred mixture of 7-tert-butoxycarbonyl-2-exo-(5-bromo-3-pyridyl)-7-azabicyclo[2.2.1]heptane (63 mg, 0.18 mmol), 6-[(tert-butyldimethylsilyl)oxy]-1-hexyne (250 mg, 1.18 mmol), Bu$_4$NI (60 mg), DMF (1.5 mL), and Et$_3$N (1.5 mL) were added Pd(PPh$_3$)$_2$Cl$_2$ (20 mg, 28 μmol) and CuI (5 mg, 26 μmol). The resulting reaction mixture was refluxed under argon for 48 h and then cooled to room temperature. The solvent was removed in vacuo, and the residue was pass through a short column of silica gel. The crude product was further purified by chromatography with hexane/EtOAc (5:1) to afford a syrup (80 mg, 93%). $^1$H NMR (CDCl$_3$) δ 8.45 (d, 1H, J=2.1 Hz), 8.36 (d, 1H, J=2.1 Hz), 7.63 (t, 1H, J=2.1 Hz), 4.39 (br s, 1H), 4.19 (s, 1H), 3.70-3.63 (m, 2H), 2.85 (dd, 1H, J=8.7, 5.1 Hz), 2.50-2.40 (m, 2H), 1.98 (dd, 1H, J=12.3, 9.0 Hz), 1.95-1.49 (m, 9H), 1.44 (s, 9H), 0.90 (s, 9H), 0.06 (s, 6H); $^{13}$C NMR (CDCl$_3$) δ 150.17, 147.32, 140.23, 136.76, 120.79, 93.56, 79.80, 77.65, 62.57, 61.68, 55.56, 45.47, 39.93, 31.93, 29.92, 28.78, 28.28, 25.93, 25.02, 19.21, 18.32, −5.32.

2-exo-(5-(6-Hydroxy-1-hexynyl)-3-pyridyl)-7-azabicyclo[2.2.1]heptane: To a stirred solution of 7-tert-butoxycarbonyl-2-exo-(5-(6-tert-butyl(dimethyl)silyloxy-1-hexynyl)-3-pyridyl)-7-azabicyclo[2.2.1]heptane (80 mg, 0.17 mmol) in dichloromethane (2 mL) was added trifluoroacetic acid (0.4 mL). The reaction mixture was stirred at room temperature for 8 h, treated with saturated aq. K$_2$CO$_3$ solution, and diluted with CH$_2$Cl$_2$. The organic phase was separated, washed with brine, dried over Na$_2$SO$_4$, and concentrated. The residue was purified by chromatography with CH$_2$Cl$_2$-MeOH (4:1) to give a syrup (40 mg, 90%). $^1$H NMR (CDCl$_3$) δ 8.43 (d, 1H, J=2.1 Hz), 8.38 (d, 1H, J=2.1 Hz), 7.72 (t, 1H, J=2.1 Hz), 3.81 (m, 1H), 3.71 (t, 2H, J=6.0 Hz), 3.61 (d, 1H, J=2.7 Hz), 2.79 (dd, 1H, J=9.0, 5.1 Hz), 2.47 (t, 2H, J=6.9 Hz), 2.15 (br s, 2H), 1.92 (dd, 1H, J=12.3, 9.0 Hz), 1.82-1.42 (m, 9H); $^{13}$C NMR (CDCl$_3$) δ 149.97, 147.41, 139.65, 136.93, 120.82, 93.57, 77.73, 62.65, 62.08, 56.96, 44.51, 39.10, 31.81, 30.43, 28.68, 24.76, 19.20.

5-(6-Iodo-1-hexanyl)-3-(1-methyl-2(S)-pyrrolidinylmethoxy)pyridine: To a stirred solution of PPh$_3$ (300 mg, 1.14 mmol) in dry CH$_2$Cl$_2$ (7 mL) was added I$_2$ (295 mg, 1.16 mmol) in one time. After 15 min, imidazole (90 mg, 1.32 mmol) was added. The mixture was stirred at room temperature for 20 min, and then 5-(6-hydroxy-1-hexanyl)-3-(1-methyl-2(S)-pyrrolidinylmethoxy)pyridine (150 mg, 0.52 mmol) in CH$_2$Cl$_2$ (1 mL) was added in dropwise. After stirred at room temperature for additional 3 h, the reaction mixture was quenched by addition of brine and diluted with CH$_2$Cl$_2$ (50 mL). The organic phase was separated, washed with aqueous NaHCO$_3$ and brine, dried over Na$_2$SO$_4$, and concentrated. The residue was purified by chromatography with EtOAc-Et$_3$N (1:0 to 25:1) to give an oil (190 mg, 92%). $^1$H NMR (CDCl$_3$) δ 8.23 (s, 2H), 7.19 (s, 1H), 3.99 (dd, 1H, J=9.3, 5.4 Hz), 3.92 (dd, 1H, J=9.3, 5.4 Hz), 3.25 (t, 2H, J=6.8 Hz), 3.14-3.08 (m, 1H), 2.69-2.61 (m, 1H), 2.48 (s, 3H), 2.46 (t, 2H, J=6.6 Hz), 2.35-2.26 (m, 1H), 2.10-1.95 (m, 1H), 1.90-1.65 (m, 5H); $^{13}$C NMR (CDCl$_3$) δ 154.41, 144.55, 137.10, 123.04, 120.82, 92.51, 77.83, 71.15, 63.97, 57.65, 41.65, 32.33, 29.09, 28.48, 22.99, 18.35, 5.97.

5-(6-Fluoro-1-hexanyl)-3-(1-methyl-2(S)-pyrrolidinylmethoxy)pyridine: A mixture of 5-(6-iodo-1-hexanyl)-3-(1-methyl-2(S)-pyrrolidinylmethoxy)pyridine (120 mg, 0.30 mmol), AgF (100 mg, 0.79 mmol), and CH$_3$CN (5 mL) was stirred at dark for 10 h. After that, the mixture was pass through a short silica gel column and washed with EtOAc-Et$_3$N (1:0 to 25:1) give an oil (50 mg, 57%), [α]$_D$ −32.4 (c 0.31, CHCl$_3$). $^1$H NMR (CDCl$_3$) δ 8.22 (s, 2H), 7.19 (m, 1H), 4.52 (dt, 2H, J=47.3, 5.8 Hz), 3.98 (dd, 1H, J=9.3, 5.4 Hz), 3.91 (dd, 1H, J=9.3, 5.4 Hz), 3.14-3.08 (m, 1H), 2.70-2.61 (m, 1H), 2.49 (t, 2H, J=6.9 Hz), 2.47 (s, 3H), 2.31 (td, 1H, J=9.3, 7.5 Hz), 2.10-1.65 (m, 8H); $^{13}$C NMR (CDCl$_3$) δ 154.47, 144.61, 137.12, 123.10, 120.95, 92.77, 83.54 (d, J=164.8 Hz), 77.79, 71.21, 64.04, 57.71, 41.70, 29.52 (d, J=19.9 Hz), 28.55, 24.33 (d, J=4.8 Hz), 23.04, 19.04.

5-(6-Tosyloxy-1-hexynyl)-3-(1-tert-butoxycarbonyl-2(S)-azetidinylmethoxy)pyridine: To a stirred solution of 5-(6- hydroxy-1-hexynyl)-3-(1-tert-butoxycarbonyl-2(S)-azetidinylmethoxy)pyridine (150 mg, 0.42 mmol) in dry $CH_2Cl_2$ (5 mL) at 0° C. was added DMAP (5 mg), $Et_3N$ (80 µL), and p-TsCl (100 mg, 0.51 mmol). The reaction mixture was stirred at room temperature overnight, and diluted with $CH_2Cl_2$ (50 mL). The organic phase was washed with aqueous $NaHCO_3$, brine, dried over $Na_2SO_4$, and concentrated. The residue was purified by chromatography with hexane-EtOAc (2:1 to 1:1) to give a viscous oil (175 mg, 82%), $[\alpha]_{546}$-36.2 (c 1.8, $CHCl_3$). $^1H$ NMR ($CDCl_3$) δ 8.24 (d, 1H, J=2.7 Hz), 8.20 (d, 1H, J=1.5 Hz), 7.80 (d, 2H, J=8.1 Hz), 7.35 (d, 2H, J=8.1 Hz), 7.22 (dd, 1H, J=2.7, 1.5 Hz), 4.51 (m, 1H), 4.32 (m, 1H), 4.12 (dd, 1H, J=7.2, 3.0 Hz), 4.10 (t, 2H, J=6.3 Hz), 3.89 (t, 1H, J=7.5 Hz), 2.45 (s, 3H), 2.41 (t, 2H, J=7.2 Hz), 2.19-2.39 (m, 2H), 1.90-1.79 (m, 2H), 1.71-1.61 (m, 2H), 1.42 (s, 9H); $^{13}C$ NMR ($CDCl_3$) δ 156.12, 154.39, 144.77, 137.31, 132.96, 129.83, 127.83, 123.19, 120.90, 92.47, 79.72, 77.86, 69.86, 68.68, 59.99, 47.00, 28.37, 27.93, 24.29, 21.60, 19.00, 18.73.

5-(6-Tosyloxy-1-hexynyl)-3-(1-tert-butoxycarbonyl-2(S)-pyrrolidinylmethoxy)pyridine: To a stirred solution of 5-(6-hydroxy-1-hexynyl)-3-(1-tert-butoxycarbonyl-2(S)-pyrrolidinylmethoxy)pyridine (900 mg, 2.4 mmol) in dry $CH_2Cl_2$ (20 mL) at 0° C. was added DMAP (50 mg), $Et_3N$ (500 µL), and p-TsCl (600 mg, 3.1 mmol). The reaction mixture was stirred at room temperature overnight, and diluted with $CH_2Cl_2$ (150 mL). The organic phase was washed with aqueous $NaHCO_3$, brine, dried over $Na_2SO_4$, and concentrated. The residue was purified by chromatography with hexane-EtOAc (2:1) to give a syrup (950 mg, 75%). $^1H$ NMR ($CDCl_3$) δ 8.21 (d, 1H, J=2.7 Hz), 8.18 (br s, 1H), 7.80 (d, 2H, J=8.4 Hz), 7.35 (d, 2H, J=8.4 Hz), 7.21 (br s, 1H), 4.13 (m, 2H), 4.09 (t, 2H, J=6.3 Hz), 4.05-3.75 (m, 1H), 3.50-3.25 (m, 2H), 2.44 (s, 3H), 2.41 (t, 2H, J=6.9 Hz), 2.10-1.79 (m, 6H), 1.71-1.60 (m, 2H), 1.47 (s, 9H); $^{13}C$ NMR ($CDCl_3$) δ 154.32, 144.74 and 144.45, 137.38 and 137.09, 132.93, 129.80, 128.40, 127.80, 125.88, 122.96, 120.83, 92.30, 79.89 and 79.46, 77.92, 69.84, 68.66 and 68.34, 55.92 and 55.58, 46.91 and 46.54, 28.45, 27.89, 24.26, 23.81, 22.79, 21.56, 18.69.

5-(6-Fluoro-1-hexynyl)-3-(1-tert-butoxycarbonyl-2(S)-azetidinylmethoxy)pyridine:

A mixture of 5-(6-tosyloxy-1-hexynyl)-3-(1-tert-butoxycarbonyl-2(S)-azetidinylmethoxy)pyridine (35 mg, 68 µmol) in 1 mL of 1.0 M solution of TBAF in THF was stirred at room temperature for 10 h. The reaction mixture concentrated. The residue was purified by chromatography with hexane-EtOAc (3:1) to give a viscous oil (25 mg, 100%), $[\alpha]_D$-40.6 (c 1.4, $CHCl_3$). $^1H$ NMR ($CDCl_3$) δ 8.24 (s, 2H), 7.24 (m, 1H), 4.52 (dt, 2H, J=47.3, 6.0 Hz), 4.56-4.47 (m, 1H), 4.38-4.26 (m, 1H), 4.12 (dd, 1H, J=10.2, 2.7 Hz), 3.89 (t, 2H, J=7.8 Hz), 2.50 (t, 2H, J=6.9 Hz), 2.42-2.21 (m, 2H), 2.04-1.69 (m, 4H), 1.42 (s, 9H); $^{13}C$ NMR ($CDCl_3$) δ 156.13, 154.40, 144.85, 137.26, 123.22, 121.05, 92.94, 83.54 (d, J=164.7 Hz), 79.74, 77.69, 68.69, 60.00, 53.62, 47.09, 29.53 (d, J=20.2 Hz), 28.38, 24.31 (d, J=5.0 Hz), 19.03; $^{19}F$ NMR ($CDCl_3$, $CFCl_3$) δ 135.4 (tt, J=47.3, 24.4 Hz).

5-(6-Fluoro-1-hexynyl)-3-(1-tert-butoxycarbonyl-2(S)-pyrrolidinylmethoxy)pyridine A mixture of 5-(6-tosyloxy-1-hexynyl)-3-(1-tert-butoxycarbonyl-2(S)-pyrrolidinylmethoxy)pyridine (195 mg, 0.37 mmol) and in 2 mL of 1.0 M solution of TBAF in THF was stirred at room temperature for 15 h. The reaction mixture concentrated. The residue was purified by chromatography with hexane-EtOAc (3:1) to give a viscous oil (135 mg, 97%), $[\alpha]_D$=-58 (c 0.44, $CHCl_3$). $^1H$ NMR ($CDCl_3$) δ 8.21 (m, 2H), 7.23 (br s, 1H), 4.52 (dt, 2H, J=47.3, 6.0 Hz), 4.14 (br s, 2H), 4.05-3.75 (m, 1H), 3.50-3.25 (m, 2H), 2.49 (t, 2H, J=6.9 Hz), 2.08-1.70 (m, 8H), 1.48 (s, 9H); $^{13}C$ NMR ($CDCl_3$) δ 154.37, 144.82 and 144.57, 137.38 and 137.08, 123.03, 121.03, 83.56 (d, J=165.2 Hz), 79.53, 68.65 and 68.41, 55.99 and 55.62, 46.97 and 46.60, 29.67 and 29.41, 28.51, 28.03, 24.32 (d, J=4.5 Hz), 23.87, 22.82, 19.04; $^{19}F$ NMR ($CDCl_3$, $CFCl_3$) δ 131.0 (tt, J=47.3, 24.4 Hz).

5-(6-Fluoro-1-hexynyl)-3-(2(S)-azetidinylmethoxy)pyridine: To a stirred solution of 5-(6-fluoro-1-hexynyl)-3-(1-tert-butoxycarbonyl-2(S)-azetidinylmethoxy)pyridine (300 mg, 0.83 mmol) in dry $CH_2Cl_2$ (2.0 mL) at 0° C. was added $CF_3CO_2H$ (2.0 mL). The mixture was stirred at room temperature for 2 h, treated with saturated aq. $K_2CO_3$ solution, and extracted with $CH_2Cl_2$ (50 mL×3). The organic layers were combined, washed with brine, dried over $Na_2SO_4$, and concentrated. The residue was purified by chromatography with $CH_2Cl_2$-MeOH-$Et_3N$ (3:1:0 to 3:1:0.1) to give a yellow oil (160 mg, 74%). $^1H$ NMR ($CDCl_3$) δ 8.22 (s, 2H), 7.21 (s, 1H), 4.51 (dt, 2H, J=47.2, 5.9 Hz), 4.32 (m, 1H), 4.10-4.01 (m, 2H), 3.76-3.50 (m, 3H), 2.49 (t, 2H, J=6.7 Hz), 2.48-2.20 (m, 2H), 2.00-1.70 (m, 4H); $^{13}C$ NMR ($CDCl_3$) δ 154.30, 144.83, 137.11, 123.24, 121.08, 92.96, 83.57 (d, J=164.4 Hz), 77.74, 72.10, 57.09, 44.07, 29.55 (d, J=19.7 Hz), 24.33 (d, J=4.7 Hz), 23.54, 19.06; $^{19}F$ NMR ($CDCl_3$) δ 135.4 (tt, J=47.3, 24.4 Hz). HPLC: Waters µBondapak™ $C_{18}$ column (7.8×300 mm), 10% $CH_3CN$ in water containing 0.05% $CF_3CO_2H$ to 40% $CH_3CN$ in water containing 0.05% $CF_3CO_2H$; flow rate 2.8 mL/min; t=22.5 min.

5-(6-Fluoro-1-hexynyl)-3-(2(S)-pyrrolidinylmethoxy)pyridine: To a stirred solution of 5-(6-fluoro-1-hexynyl)-3-(1-tert-butoxycarbonyl-2(S)-pyrrolidinylmethoxy)pyridine (110 mg, 0.29 mmol) in dry $CH_2Cl_2$ (2.0 mL) at 0° C. was added $CF_3CO_2H$ (1.0 mL). The mixture was stirred at room temperature for 1 h, treated with saturated aq. $K_2CO_3$ solution, and diluted with $CH_2Cl_2$. The organic phase was separated, washed with brine, dried over $Na_2SO_4$, and concentrated. The residue was purified by chromatography with $CH_2Cl_2$-MeOH (10:1 to 3:1) to give a yellow oil (75 mg, 93%), $[\alpha]_D$=-6.3 (c 0.95, $CHCl_3$). $^1H$ NMR ($CDCl_3$) δ 8.21 (s, 2H), 7.19 (s, 1H), 4.52 (dt, 2H, J=47.3, 5.8 Hz), 3.98-3.85 (m, 2H), 3.57-2.52 (m, 1H), 3.10-2.95 (m, 2H), 2.49 (t, 2H, J=6.8 Hz), 2.44 (br s, 1H), 2.10-1.50 (m, 8H); $^{13}C$ NMR ($CDCl_3$) δ 154.37, 144.70, 137.14, 123.08, 121.02, 92.84, 83.55 (d, J=164.8 Hz), 77.80, 71.61, 57.03, 46.55, 29.53 (d, J=19.4 Hz), 27.88, 25.24, 24.35, 24.33 (d, J=4.9 Hz), 19.04; 19F NMR ($CDCl_3$) δ 135.4 (tt, J=47.3, 24.4 Hz). HPLC: Waters µBondapak™ $C_{18}$ column (7.8×300 mm), 10% $CH_3CN$ in water containing 0.05% $CF_3CO_2H$ to 40% $CH_3CN$ in water containing 0.05% $CF_3CO_2H$; flow rate 2.8 mL/min; t=14.8 n.

INCORPORATION BY REFERENCE

All of the U.S. patents and U.S. patent application publications cited herein are hereby incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

We claim:

1. A compound of formula III:

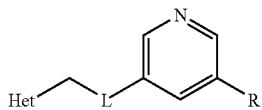

wherein, independently for each occurrence,

L is O;

Het is a 2-azetidinyl group; and

R is a substituted $C_2$-$C_{10}$ alkynyl, wherein the substituent is selected from the group consisting of hydroxy and halide.

2. The compound of claim 1, wherein R is an hydroxy substituted alkynyl group.

3. The compound of claim 1, wherein R is —C≡C—$(CH_2)_4$—OH.

4. The compound of claim 1, wherein the compound is a single stereoisomer.

5. A pharmaceutical composition, comprising a compound of claim 1; and a pharmaceutically acceptable excipient.

6. A method of modulating a nicotine ACh receptor in a mammal, comprising administering to the mammal a compound of claim 1.

7. The method of claim 6, wherein the mammal is a primate, equine, canine, or feline.

8. The method of claim 6, wherein the mammal is a human.

9. A method of treating a mammal suffering from Alzheimer's disease, Parkinson's disease, dyskinesias, Tourette's syndrome, schizophrenia, attention deficit disorder, anxiety, pain, depression, obsessive compulsive disorder, chemical substance abuse, alcoholism, memory deficit, pseudodementia, Ganser's syndrome, migraine pain, bulimia, obesity, premenstrual syndrome or late luteal phase syndrome, tobacco abuse, post-traumatic syndrome, social phobia, chronic fatigue syndrome, premature ejaculation, erectile difficulty, anorexia nervosa, disorders of sleep, autism, mutism or trichtillomania, comprising administering a compound of claim 1.

10. The method of claim 9, wherein the mammal is a primate, equine, canine, or feline.

11. The method of claim 9, wherein the mammal is a human.

12. The compound of claim 1, wherein R is a fluorine substituted alkynyl group.

13. The compound of claim 1, wherein R is —C≡C—$(CH_2)_4$—F.

* * * * *

UNITED STATES PATENT AND TRADEMARK OFFICE
CERTIFICATE OF CORRECTION

PATENT NO. : 8,030,300 B2
APPLICATION NO. : 10/558607
DATED : October 4, 2011
INVENTOR(S) : Alan P. Kozikowski et al.

It is certified that error appears in the above-identified patent and that said Letters Patent is hereby corrected as shown below:

In the Specification

At Column 1, Line number 15-18:
"Work described herein was funded, in whole or in part, by the National Institutes of Health (R01 Grant Number DA017980). The United States government has certain rights in the invention."

Should read:
--This invention was made with government support under grant number R01 DA017980 awarded by the National Institutes of Health. The government has certain rights in the invention.--

Signed and Sealed this
Seventeenth Day of October, 2023

Katherine Kelly Vidal
*Director of the United States Patent and Trademark Office*